(12) United States Patent
Gruss

(10) Patent No.: US 9,296,749 B2
(45) Date of Patent: Mar. 29, 2016

(54) CRYSTALLINE CIS-(E)-4-(3-FLUOROPHENYL)-2',3',4',9'-TETRAHYDRO-N,N-DIMETHYL-2'-(1-OXO-3-PHENYL-2-PROPENYL)-SPIRO[CYCLOHEXANE-1,1'[1H]

(71) Applicant: Gruenenthal GmbH, Aachen (DE)

(72) Inventor: Michael Gruss, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 14/212,088

(22) Filed: Mar. 14, 2014

(65) Prior Publication Data

US 2014/0288307 A1    Sep. 25, 2014

Related U.S. Application Data

(60) Provisional application No. 61/790,733, filed on Mar. 15, 2013.

(30) Foreign Application Priority Data

Mar. 15, 2013    (EP) .................................... 13001331

(51) Int. Cl.
    *C07D 471/10*    (2006.01)
(52) U.S. Cl.
    CPC ........... *C07D 471/10* (2013.01); *C07B 2200/13* (2013.01)
(58) Field of Classification Search
    CPC .................................................... C07D 471/10
    USPC .......................................................... 546/18
    See application file for complete search history.

(56) References Cited

U.S. PATENT DOCUMENTS

| 7,332,519 B2 | 2/2008 | Hinze et al. |
| 7,951,948 B2 | 5/2011 | Hinze et al. |
| 7,960,404 B2 | 6/2011 | Schunk et al. |
| 8,034,936 B2 | 10/2011 | Friderichs et al. |
| 2012/0029006 A1 | 2/2012 | Linz et al. |

FOREIGN PATENT DOCUMENTS

| WO | WO 2004/043967 A1 | 5/2004 |
| WO | WO 2005/066183 A1 | 7/2005 |
| WO | WO 2006/108565 A1 | 11/2006 |
| WO | WO 2008/101660 A1 | 8/2008 |
| WO | WO 2012/013343 A1 | 2/2012 |

OTHER PUBLICATIONS

R. Hilfiker, "Polymorphism in the Pharmaceutical Industry", 2006 Wiley VCH, pp. 235-242 (ten (10) pages).

*Primary Examiner* — Rita Desai
(74) *Attorney, Agent, or Firm* — Crowell & Moring LLP

(57) ABSTRACT

The present invention relates to crystalline forms of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine, pharmaceutical compositions and medicaments comprising these modifications, the use of these modifications as well as to a process for making the crystalline forms.

44 Claims, 20 Drawing Sheets

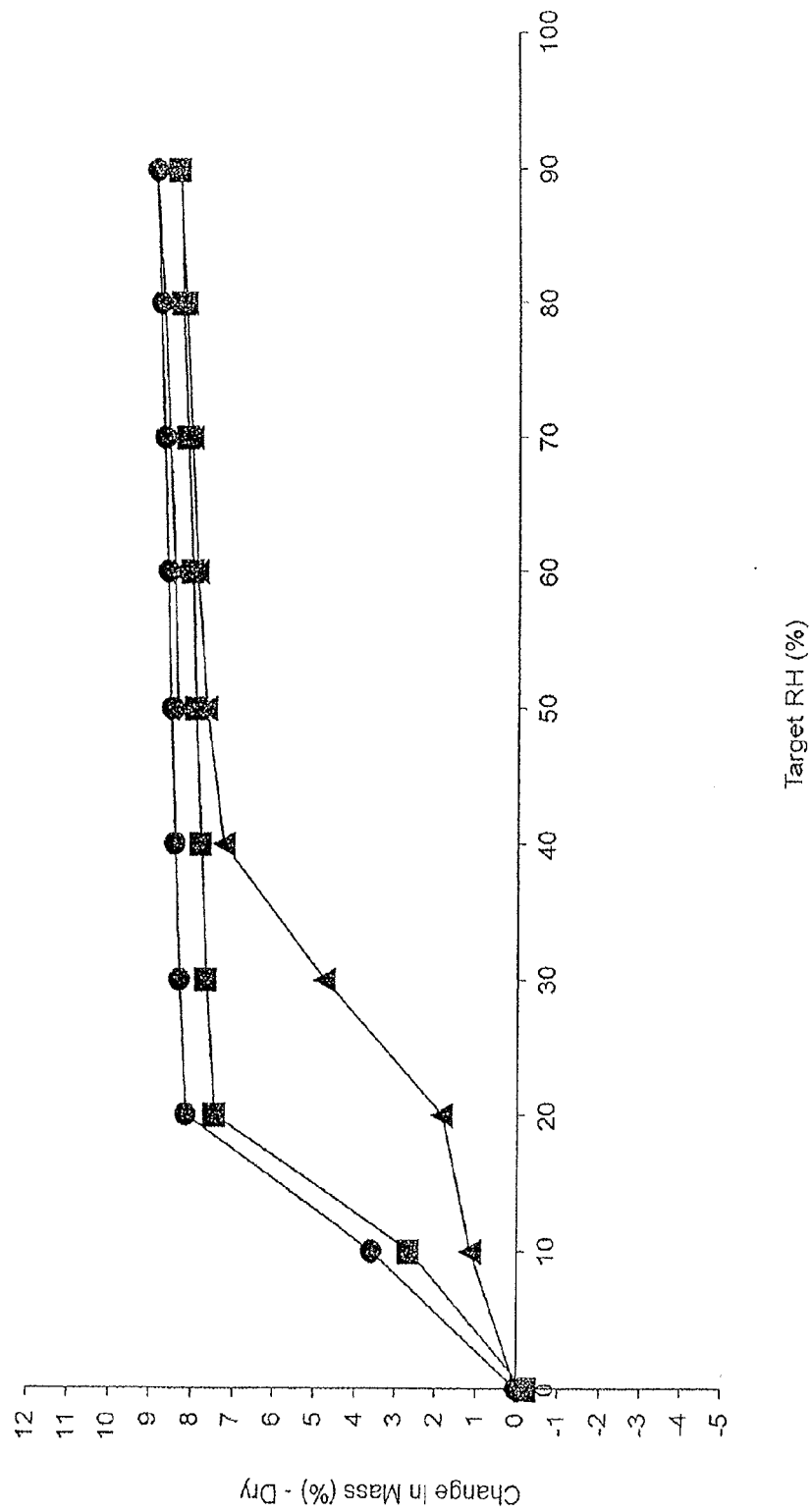

CRYSTALLINE CIS-(E)-4-(3-FLUOROPHENYL)-2',3',4',9'-TETRAHYDRO-N,N-DIMETHYL-2'-(1-OXO-3-PHENYL-2-PROPENYL)-SPIRO[CYCLOHEXANE-1,1'[1H]

FIELD OF THE INVENTION

The invention relates to crystalline forms of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine, pharmaceutical compositions and medicaments comprising one or more of these crystalline forms, the use of these crystalline forms as well as to processes for producing these crystalline forms.

BACKGROUND OF THE INVENTION

Pharmaceutically active drugs can exist in different solid forms. For example, a drug may exist in different crystalline forms which have different physical, physic-chemical and chemical properties.

Different physical or physic-chemical properties can cause different crystalline forms of the same drug to have largely different processing and storage performance. Such physical or physico-chemical properties include, for example, thermodynamic stability, crystal morphology [form, shape, structure, particle size, particle size distribution, color, degree of crystallinity, ripple behavior, flowability, density, bulk density, powder density, apparent density, vibrated density, depletability, emptyability, hardness, deformability, grindability, compressability, compactability, brittleness, elasticity, caloric properties [particularly melting point], solubility [particularly equilibrium solubility, pH dependence of solubility], dissolution [particularly dissolution rate, intrinsic dissolution rate], reconstitutability, hygroscopicity, tackiness, adhesiveness, tendency to electrostatic charging, and the like.

In addition, different chemical properties can cause different crystalline forms of the same drug to have largely different performance properties. For example, a crystalline form having a low hygroscopicity (relative to other crystalline forms) can have superior chemical stability and longer shelf-life stability (cf. R. Hilfiker, Polymorphism, 2006 Wiley VCH, pp 235-242 and 251-252).

In medicine, the treatment of pain is of great importance and although a significant number of drugs are known for and established in the treatment of pain, there remains, for instance with regard to drug-related side-effects, a demand for improved pain medication, especially for the treatment of strong/severe and/or chronic and/or neuropathic pain. Consequently, a great deal of effort is still being invested by pharmaceutical companies into the development of new, improved analgesics.

One particular drug that is of great interest especially for the use in treating pain, especially chronic and/or neuropathic pain is cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine, which is described in WO2012013343-A1. The chemical structure of this drug is depicted below as the compound of formula (I):

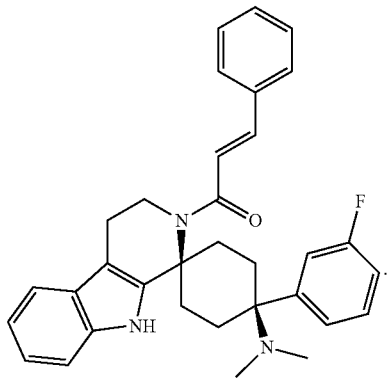

(I)

The solid forms of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine that are known so far are not satisfactory in every respect and consequently there is a demand for advantageous solid forms, especially crystalline forms. Especially, there is a demand for solid forms of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine that have advantageous properties for the use of this compound in pharmaceutical compositions and for use in methods of preparing such pharmaceutical compositions.

This object has been achieved by the present invention. It has surprisingly been found that different crystalline forms of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine can be prepared which have advantageous properties, especially for the use in pharmaceutical compositions. These inventive crystalline forms are described herein.

BRIEF DESCRIPTION OF THE DRAWINGS

FIGS. 1a, 1b, 1c, 1d, 1e, 1f, 1g, 1h, 1i, 1j, 1k and 1l show the PXRD patterns of crystalline forms A, B, C, D, E, F, G, H, I, J, K, L and Q.

DETAILED DESCRIPTION

Figure 1A:
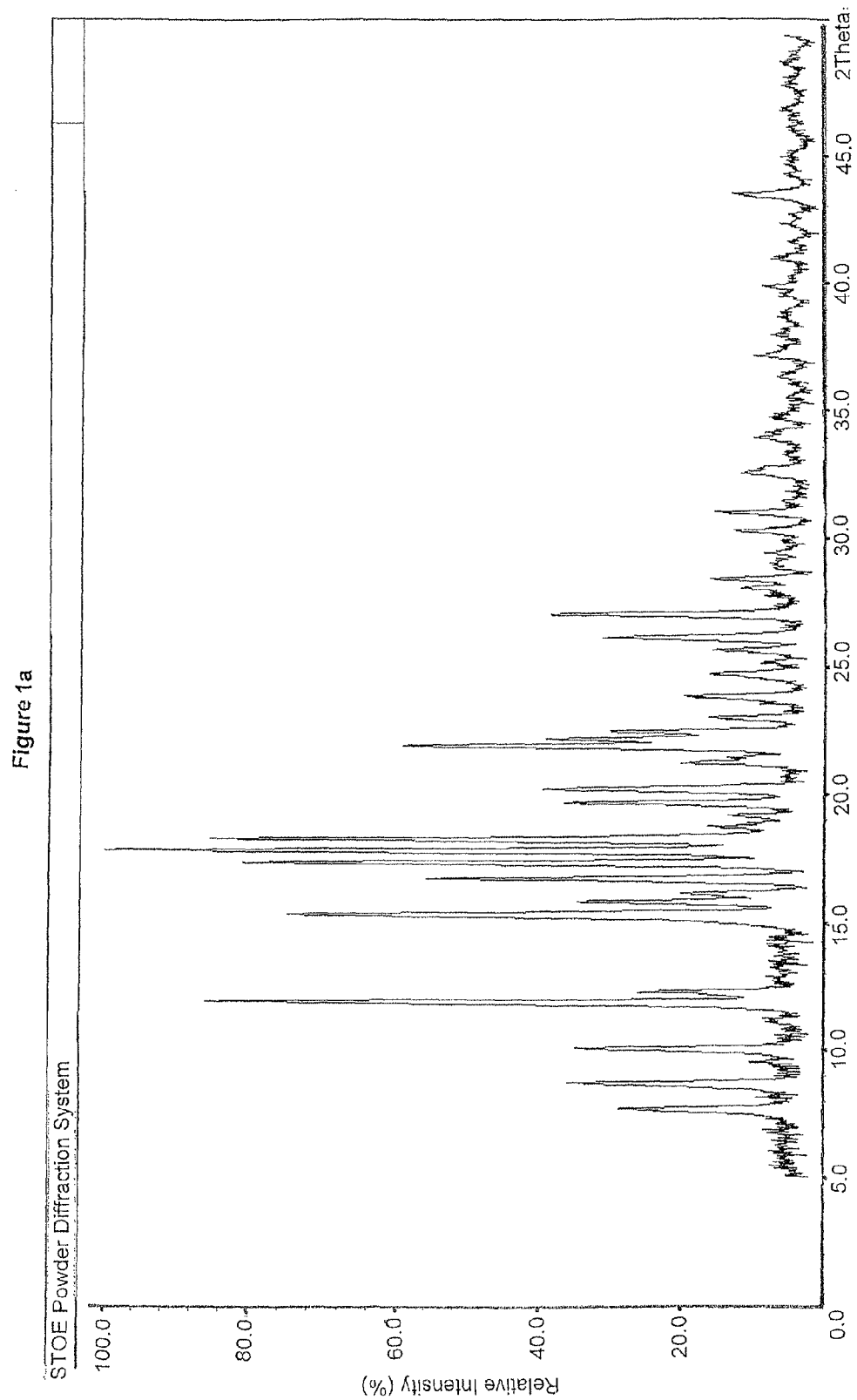
Figure 1B:
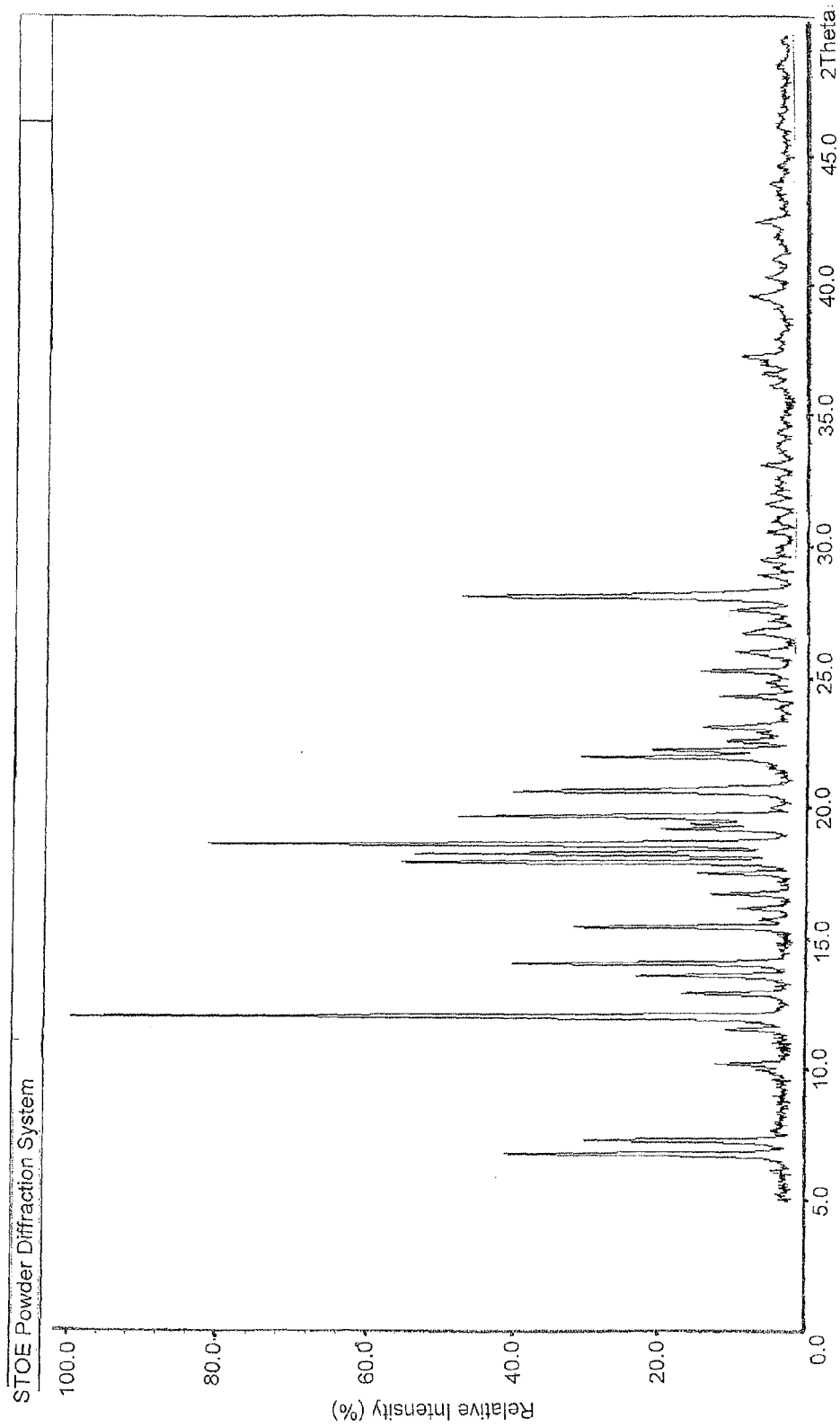
Figure 1C:
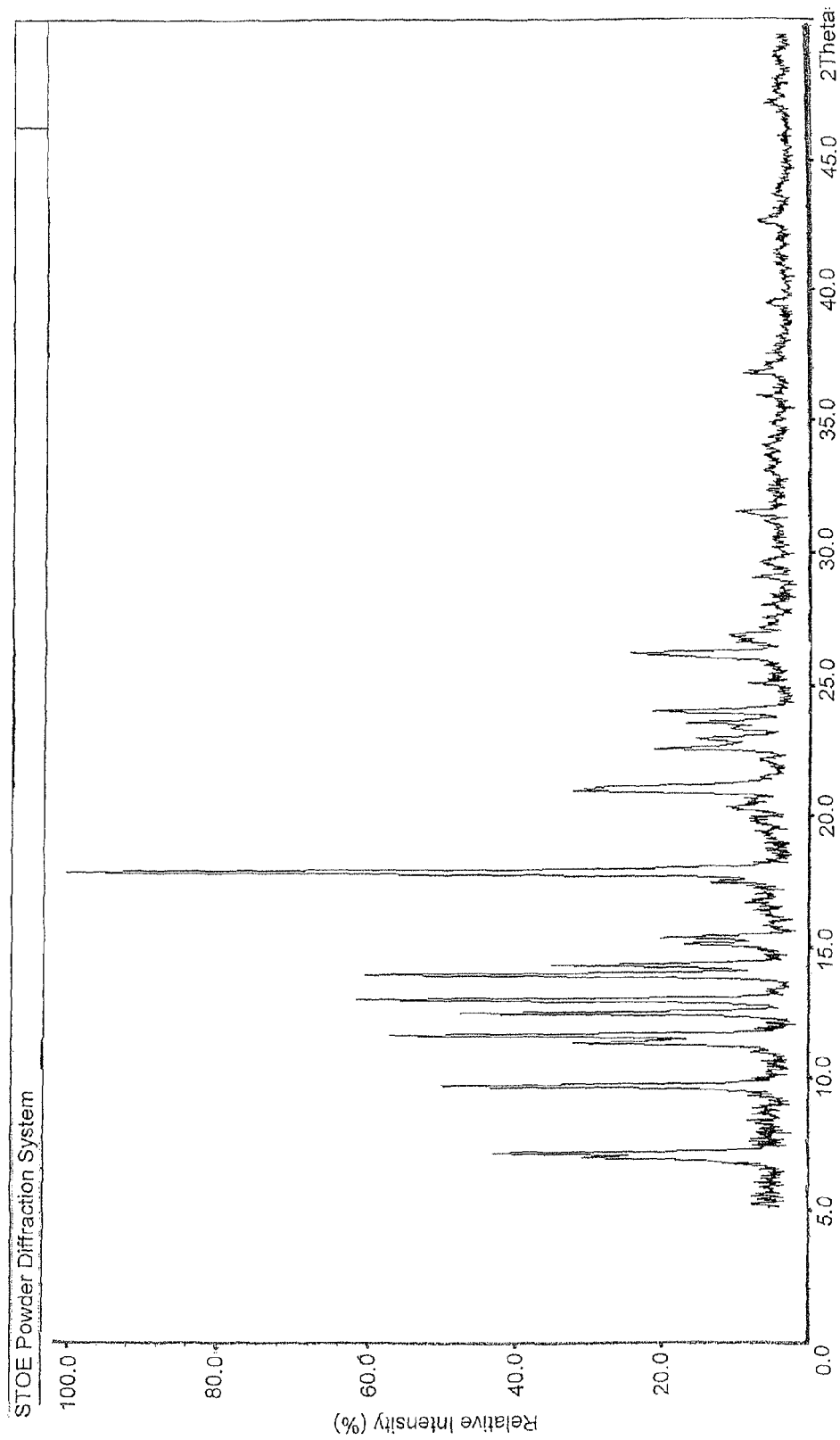
Figure 1D:
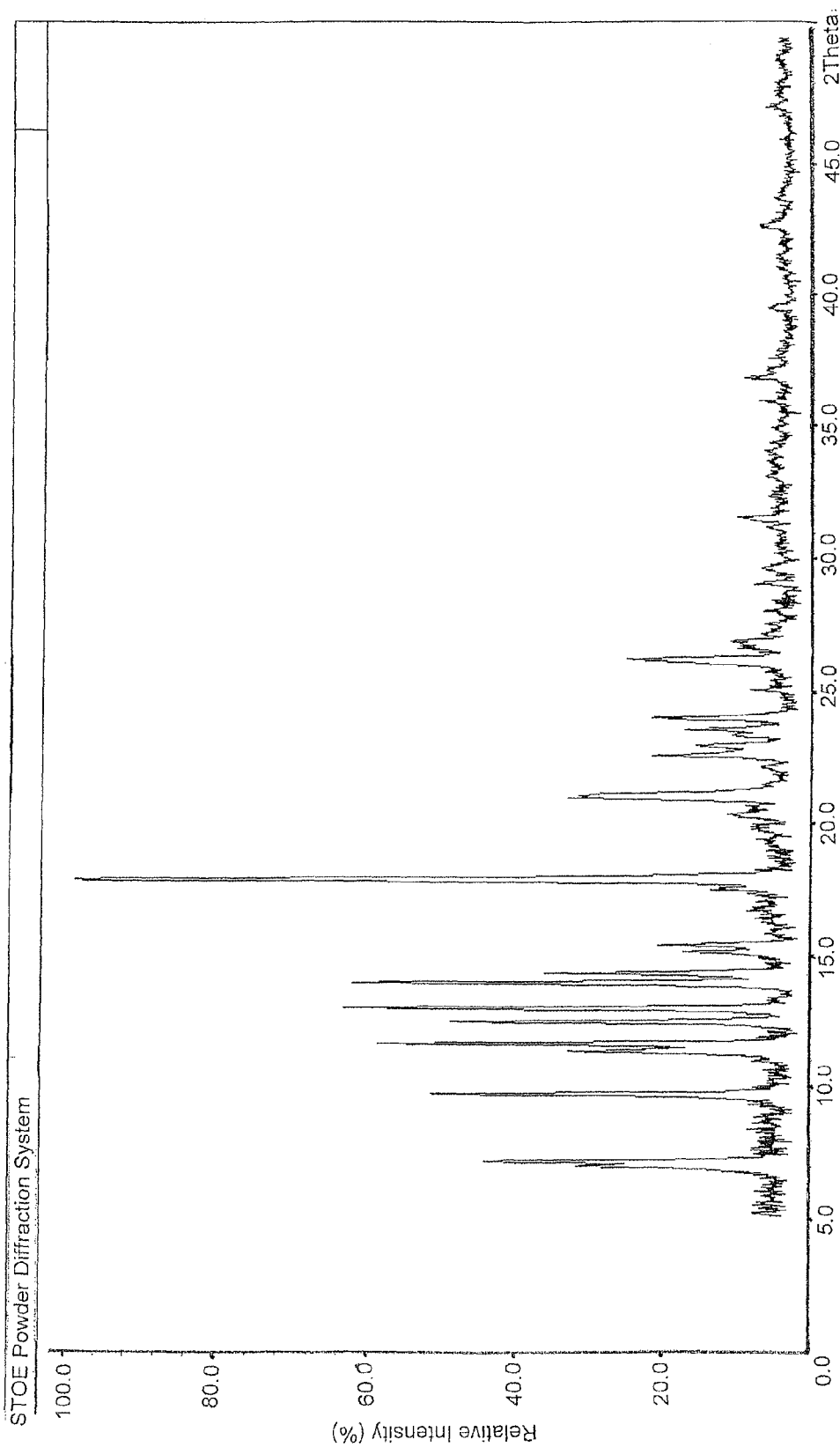
Figure 1E:
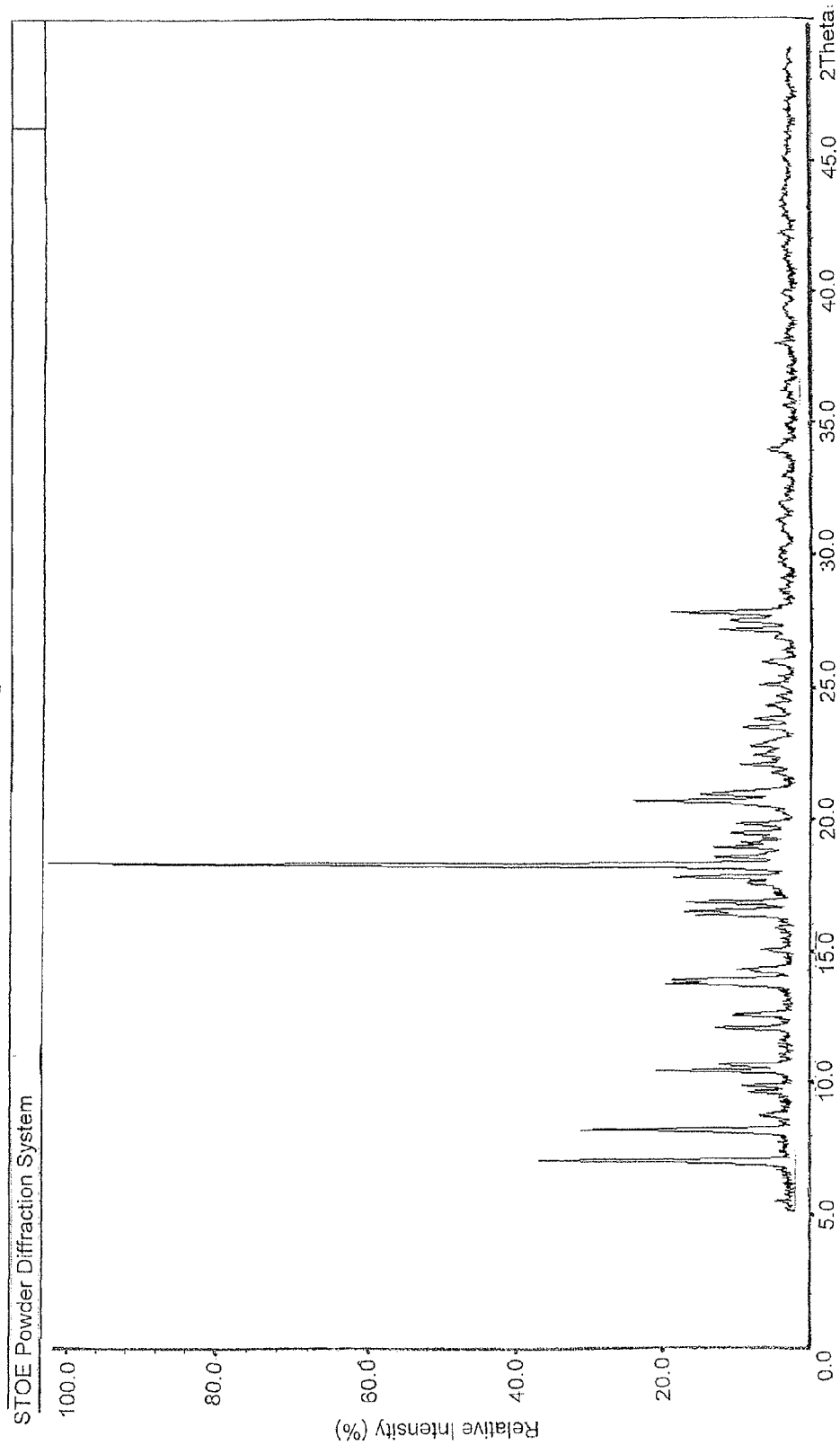
Figure 1F:
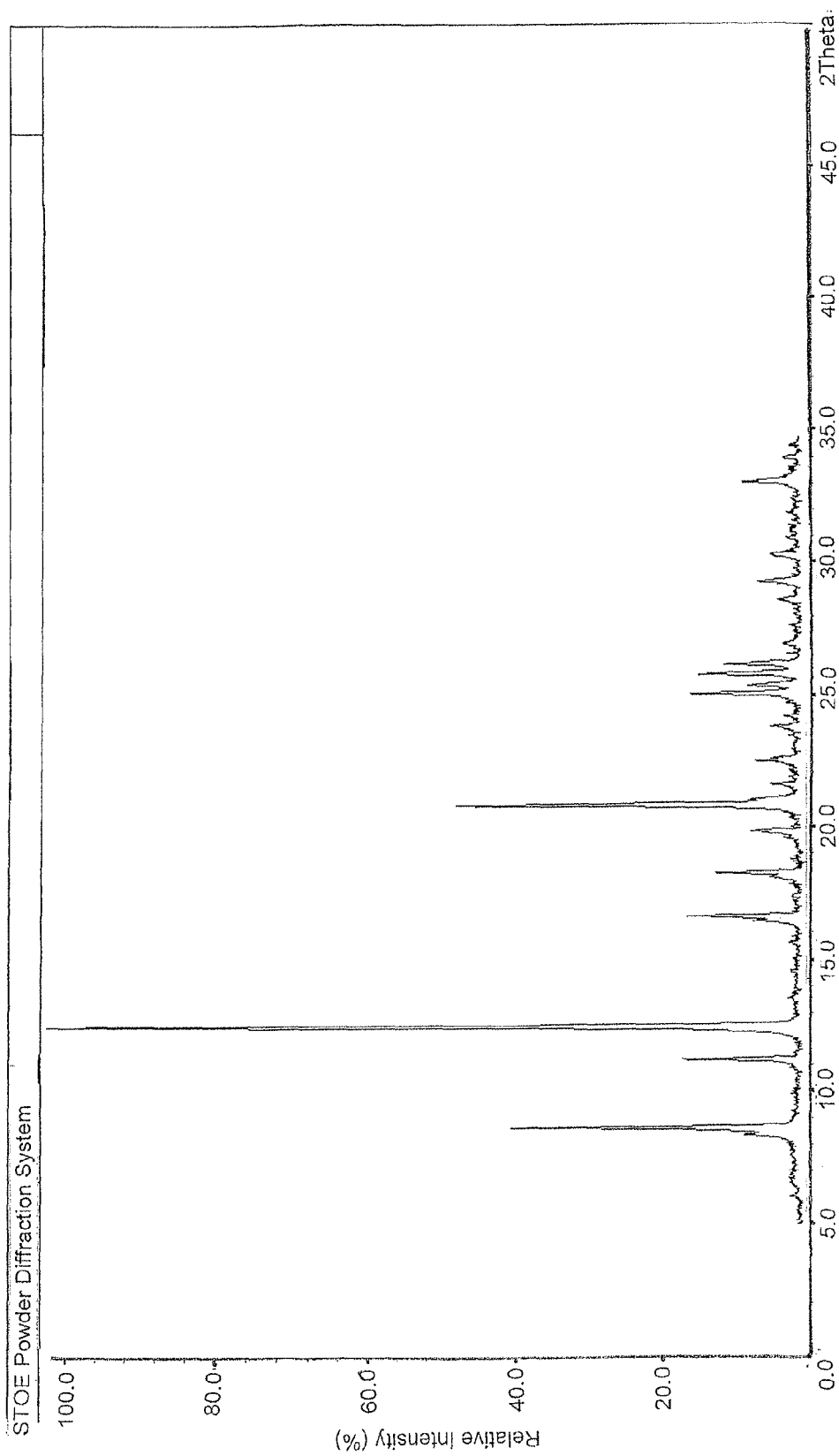
Figure 1G:
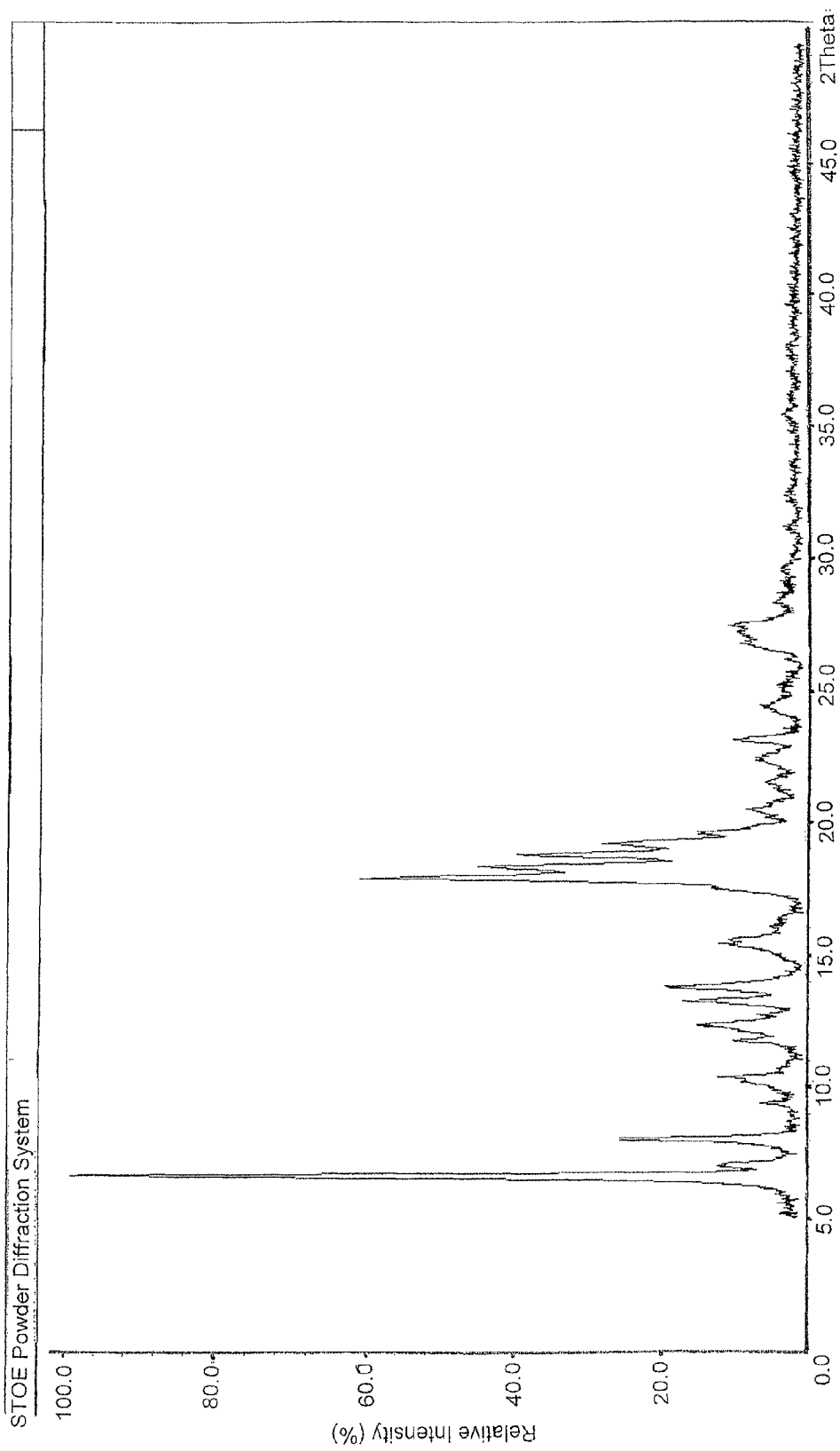
Figure 1H:
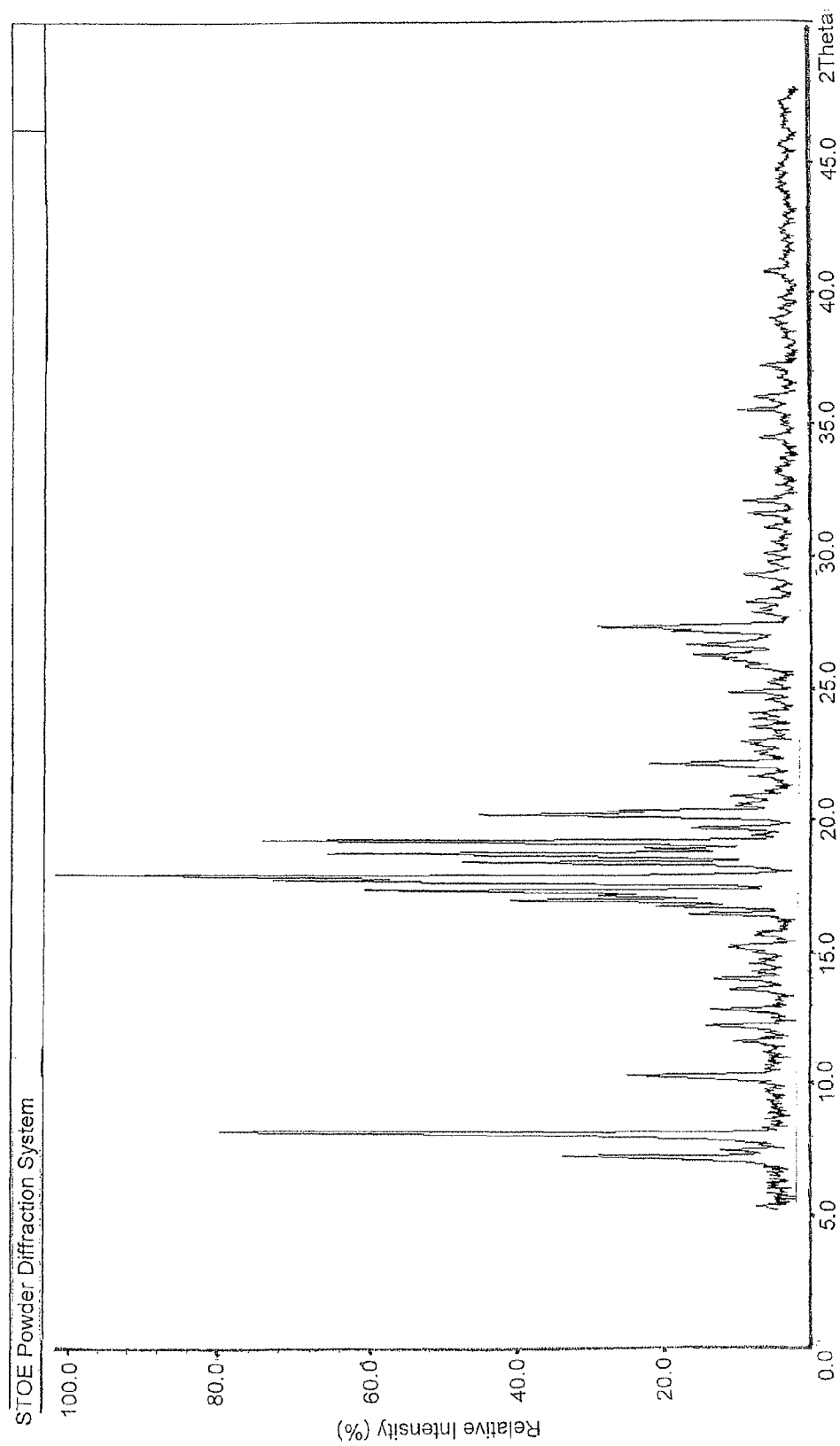
Figure 1I:
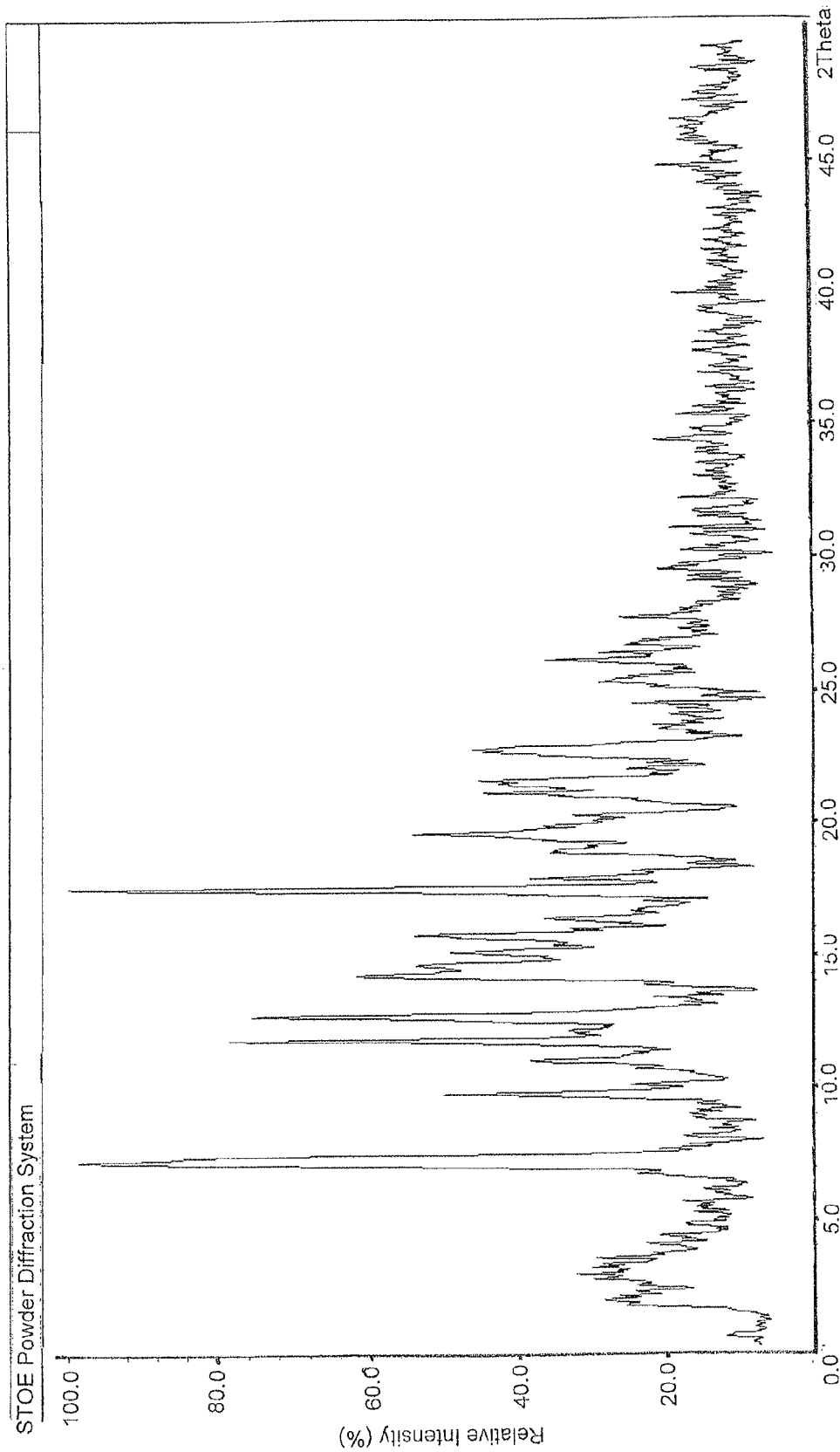
Figure 1J:
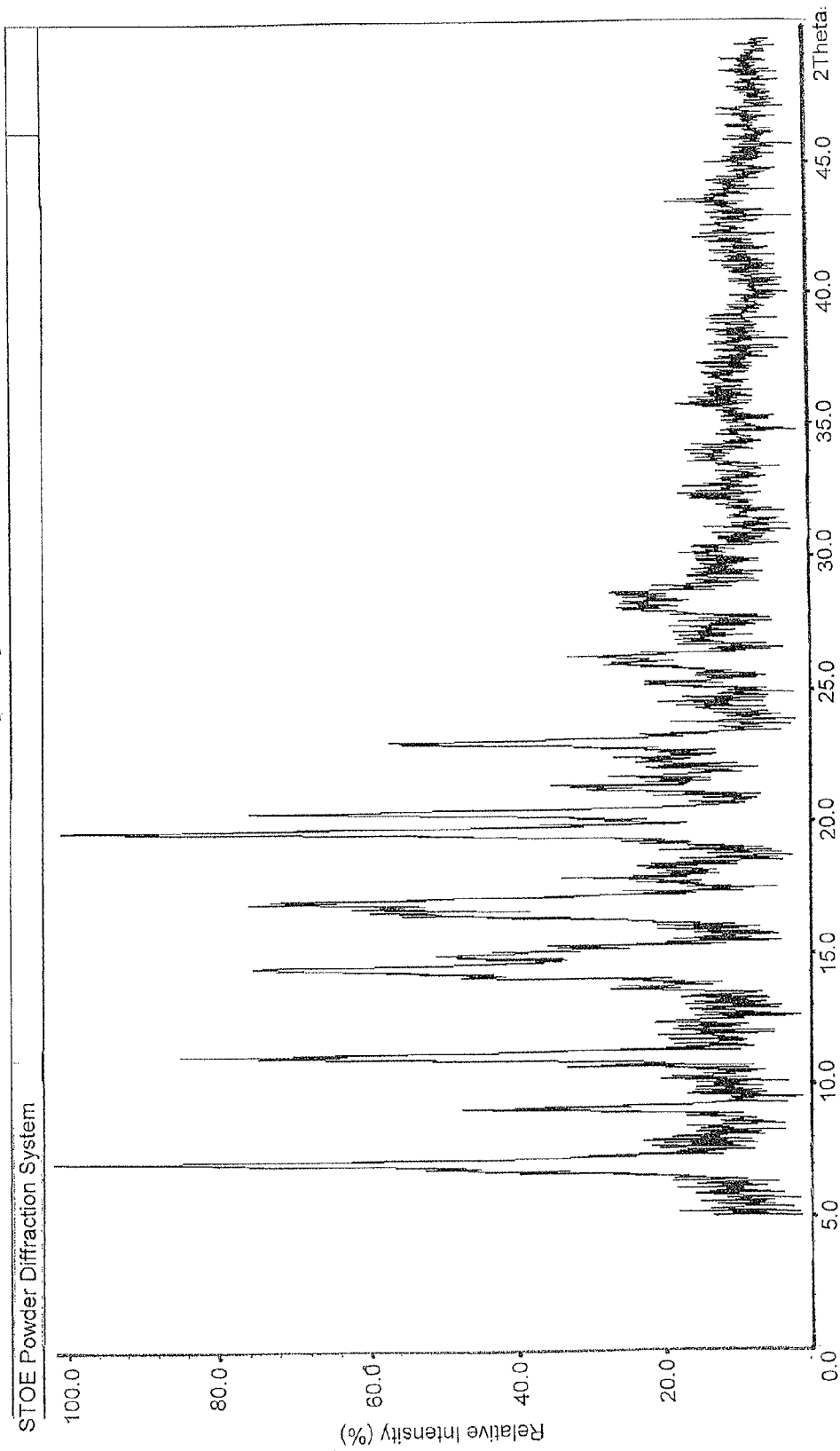
Figure 1K:
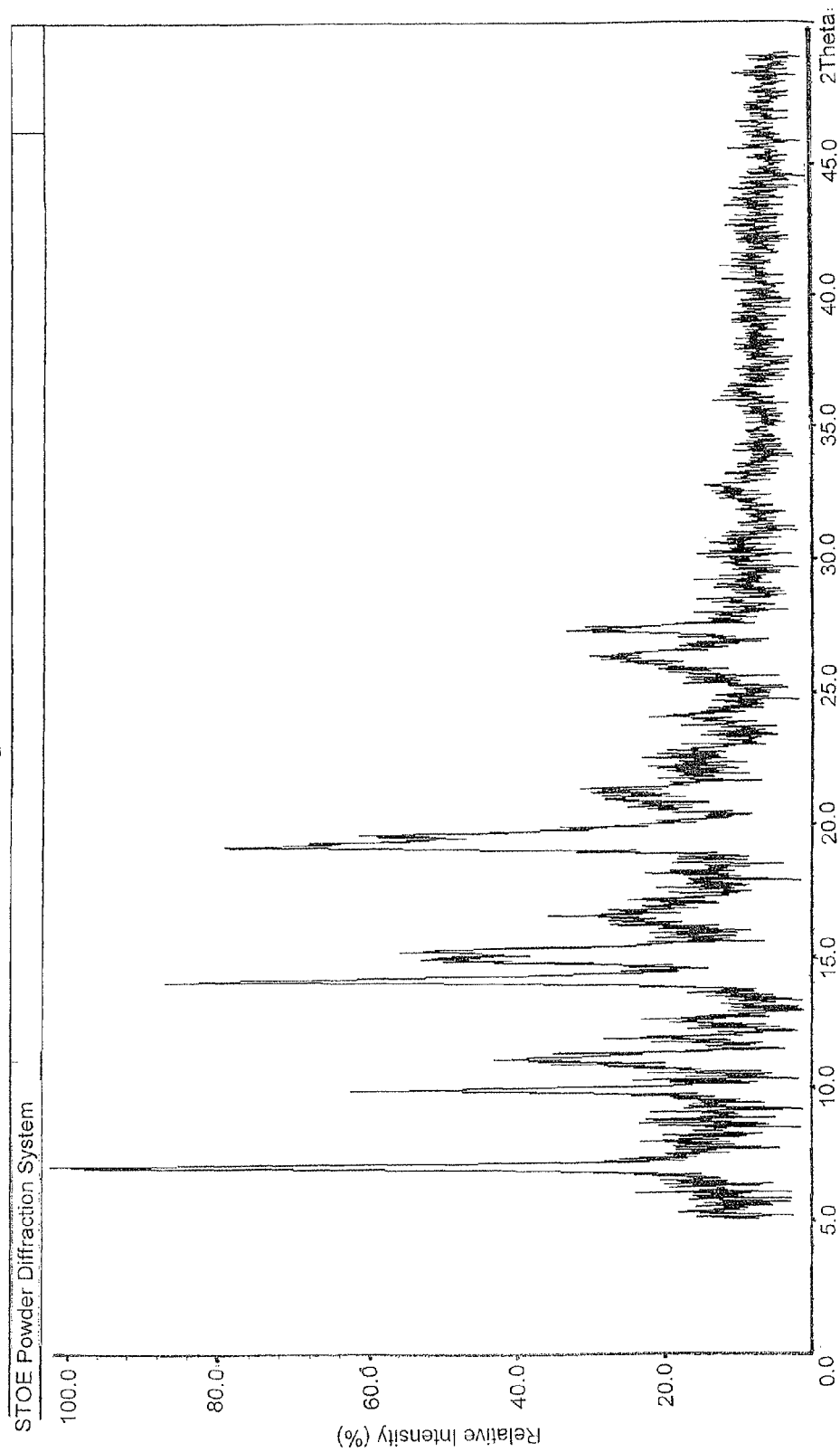
Figure 1I:
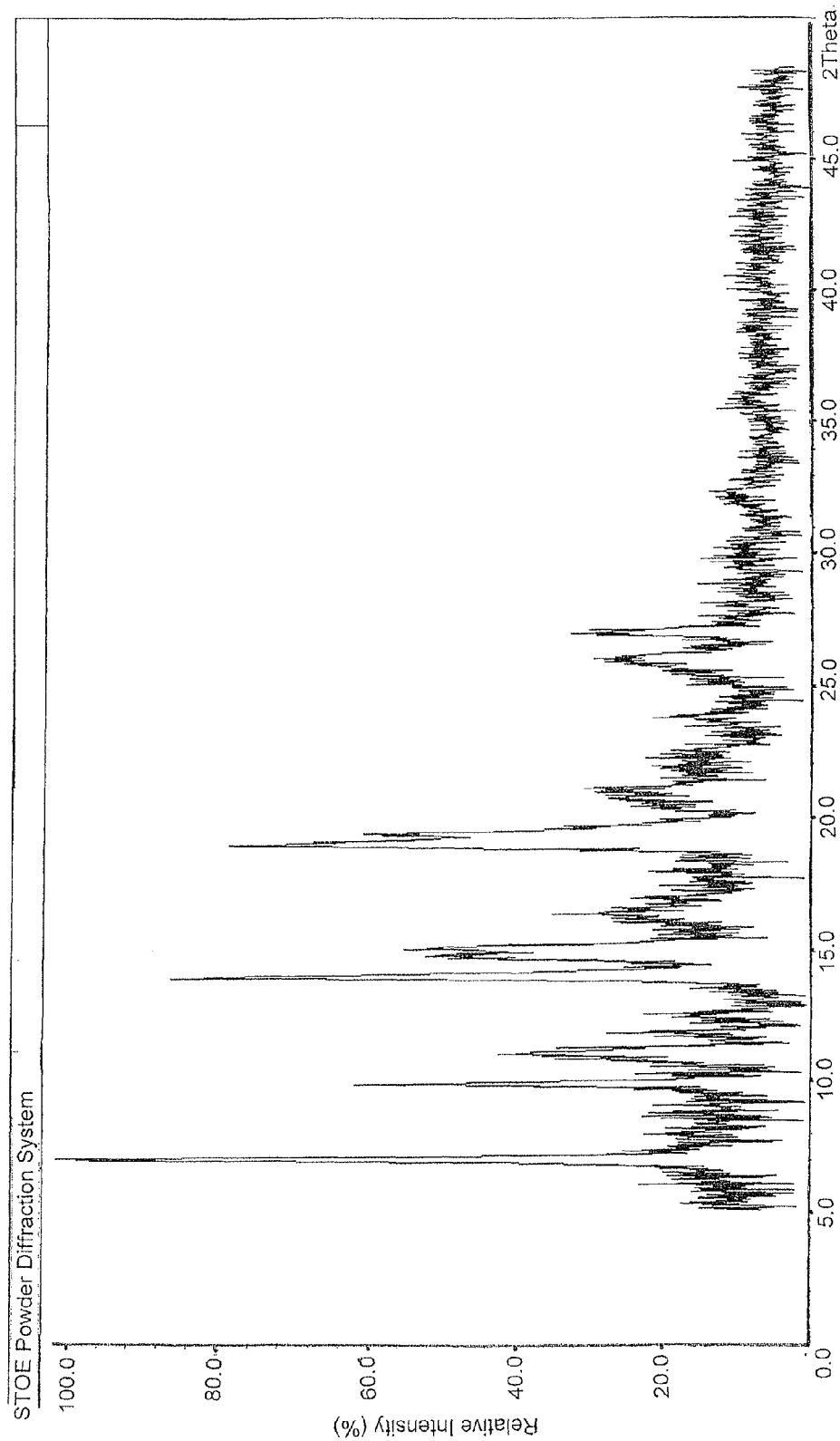

The compound according to general formula (I) depicted above can be systematically be referred to as cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine, or as cis-(E)-2',3',4',9'-tetrahydro-N,N-dimethyl-4-(3-fluorophenyl)-2'-(2-phenylvinyl)carbonyl-spiro[cyclohexane-1,1'(1'H)-pyrido[3,4-b]indole]-4-amine or as (E)-1-((1s,4s)-4-(dimethylamino)-4-(3-fluorophenyl)-3',4'-dihydrospiro[cyclohexane-1,1'-pyrido[3,4-b]indol]-2'(9'H)-yl)-3-phenylprop-2-en-1-one, respectively.

The compound according to general formula (I) may be present as the free base. The definition of the free base of the compound according to general formula (I) as used herein includes solvates, co-crystals and crystalline forms. For the purpose of the specification, "free base" preferably means that the compound according to general formula (I) is not present in form of a co-crystal or salt, particularly not in form of an acid-addition salt. The most basic functional group of the compound according to general formula (I) is its N,N-dimethylamino moiety, which thus according to the invention is preferably neither protonated nor quaternized. In other words, the free electron pair of the nitrogen atom of the N,N-dimethylamino moiety is present as a Lewis base. Methods to determine whether a chemical substance is present as the free base or as a salt are known to the skilled artisan such as $^{14}N$ or $^{15}N$ solid state NMR, x-ray diffraction, x-ray powder diffraction, IR, Raman, XPS. $^1$H-NMR recorded in solution may also be used to consider the presence of protonation.

Unless explicitly stated otherwise, all 2Θ values refer to a X-ray powder diffractogram measured using CuKα radiation having a wavelength of 1.54060 Å. The terms 2Θ values and degrees 2Θ are used synonymously.

Unless explicitly stated otherwise, all values in ppm refer to ppm by weight, i.e. ppmw.

In a first aspect, the present invention relates to a crystalline form of cis-(E)-2',3',4',9'-Tetrahydro-N,N-dimethyl-4-(3-fluorophenyl)-2'-(2-phenylvinyl)carbonyl-spiro[cyclohexane-1,1'(1'H)-pyrido[3,4-b]indole]-4-amine.

In a preferred embodiment of the invention, the crystalline form according to the invention has at least one X-ray powder diffraction peak (CuKα radiation) in the range of 6.5±0.2 to 8.9±0.2 (2Θ) and/or 17.2±0.2 to 18.3±0.2 (2Θ) and/or in the range of 19.7±0.2 to 20.9±0.2 (2Θ).

Preferably, said X-ray powder diffraction peak exhibits a relative intensity of at least 10%, preferably of at least 20%, more preferably of at least 30%.

In further preferred embodiments the crystalline form according to the invention is an ansolvate or a solvate.

In some preferred embodiments the crystalline form according to the invention is an ansolvate. In other preferred embodiments the crystalline form according to the invention is a solvate, preferably selected from the group of hydrates, solvates of lower alcohols, such as methanol, ethanol, 1-propanol or 2-propanol or solvates of toluene or a solvate of solvate mixtures. Preferably, the solvate is selected from the group consisting of monosolvate, hemi-solvate, disolvate, trisolvate, and mixtures thereof. In another preferred embodiment the solvate is a variable or non-stoichiometric solvate.

In a preferred embodiment, the crystalline form is a hydrate, preferably selected from the group consisting of monohydrate, hemi-hydrate, dihydrate, trihydrate, and mixtures thereof. In some preferred embodiments, the crystalline form is a trihydrate. In another preferred embodiment the hydrate is a variable or non-stoichiometric hydrate. In another preferred embodiment the alcohol solvate is a variable or non-stoichiometric alcohol solvate.

In another preferred embodiment, the crystalline form is an alcohol solvate, preferably selected from the group consisting of methanol, ethanol or propanolate (1-propanol or 2-propanol) solvates, and the mixtures thereof, the 1-methanol solvate being particularly preferred.

In a further preferred embodiment of the invention, the crystalline form is one which has A: one or more X-ray powder diffraction peaks (CuKα radiation) selected from the group consisting of 8.7±0.2 (2Θ), 11.9±0.2 (2Θ), 18.3±0.2 (2Θ), and 27.1±0.2 (2Θ) and/or one or more Raman peaks selected from the group consisting of at 1606±2 cm$^{-1}$, 1175±2 cm$^{-1}$, 1568±2 cm$^{-1}$, 1574±2 cm$^{-1}$ and 1650±2 cm$^{-1}$; or B: one or more X-ray powder diffraction peaks (CuKα radiation) selected from the group consisting of at 6.8±0.2 (2Θ), 12.1±0.2 (2Θ), 18.7±0.2 (2Θ), and 28.3±0.2 (2Θ); and/or one or more Raman peaks selected from the group consisting of at 1643±2 cm$^{-1}$ and 1578±2 cm$^{-1}$; or C: one or more X-ray powder diffraction peaks (CuKα radiation) selected from the group consisting of 9.7±0.2 (2Θ), 11.6±0.2 (2Θ), 14.0±0.2 (2Θ), and 17.9±0.2 (2Θ); or D: one or more X-ray powder diffraction peaks (CuKα radiation) selected from the group consisting of 8.7±0.2 (2Θ), 11.6±0.2 (2Θ), 16.6±0.2 (2Θ), and 21.2±0.2 (2Θ); and/or one or more Raman peaks selected from the group consisting of 1612±2 cm$^{-1}$ and 1199 cm$^{-1}$±2 cm$^{-1}$; or E: one or more X-ray powder diffraction peaks (CuKα radiation) selected from the group consisting of 6.9±0.2 (2Θ), 8.1±0.2 (2Θ), 18.3±0.2 (2Θ) and 20.8±0.2 (2Θ); or F: one or more X-ray powder diffraction peaks (CuKα radiation) selected from the group consisting of 8.7±0.2 (2Θ), 12.5±0.2 (2Θ), 20.9±0.2 (2Θ); or G: one or more X-ray powder diffraction peaks (CuKα radiation) selected from the group consisting of 6.6±0.2 (2Θ), 8.0±0.2 (2Θ), 18.0±0.2 (2Θ), and 18.9±0.2 (2Θ);

H: one or more X-ray powder diffraction peaks (CuKα radiation) selected from the group consisting of 7.1±0.2 (2Θ), 8.0±0.2 (2Θ), 18.2±0.2 (2Θ), and 28.3±0.2 (2Θ); or I: one or more X-ray powder diffraction peaks (CuKα radiation) selected from the group consisting of 7.1±0.2 (2Θ), 11.8±0.2 (2Θ), 17.6±0.2 (2Θ) and 19.6±0.2 (2Θ); or J: one or more X-ray powder diffraction peaks (CuKα radiation) selected from the group consisting of 7.1±0.2 (2Θ), 11.1±0.2 (2Θ), 14.5±0.2 (2Θ), and 19.7±0.2 (2Θ); or K: one or more X-ray powder diffraction peaks (CuKα radiation) selected from the group consisting of 7.1±0.2 (2Θ), 10.0±0.2 (2Θ), 14.3±0.2 (2Θ), and 19.5±0.2 (2Θ); or L: one or more X-ray powder diffraction peaks (CuKα radiation) selected from the group consisting of 8.1±0.2 (2Θ), 12.0±0.2 (2Θ), 17.1±0.2 (2Θ), and 20.1±0.2 (2Θ); or Q: one or more X-ray powder diffraction peaks (CuKα radiation) selected from the group consisting of 8.2±0.2 (2Θ), 8.6±0.2 (2Θ), 17.2±0.2 (2Θ), and 24.4±0.2 (2Θ).

In a preferred embodiment of the invention, the crystalline form A exhibits in DSC analysis an endothermal event with an onset temperature in the range of 227° C. to 247° C., preferably 240° C. to 245° C. and/or a peak temperature in the range of 235° C. to 255° C., preferably 245° C. to 250° C.

In another preferred embodiment of the invention, crystalline form A has X-ray powder diffraction peaks (CuKα radiation) of 8.7±0.2 (2Θ), 11.9±0.2 (2Θ), 18.3±0.2 (2Θ), and optionally 27.1±0.2 (2Θ).

In a further preferred embodiment of the invention the crystalline form has X-ray powder diffraction peaks (CuKα radiation) at 7.7±0.2 (2Θ) and/or 17.4±0.2 (2Θ) and/or 18.3±0.2 (2Θ) and at least one additional X-ray peak selected from 10.0±0.2 (2Θ), 15.3±0.2 (2Θ), 15.8±0.2 (2Θ), 21.9±0.2 (2Θ), 22.2±0.2 (2Θ) and 27.1±0.2 (2Θ).

In still further preferred embodiments, the crystalline form has X-ray powder diffraction peaks (CuKα radiation) at 8.7±0.2 (2Θ) and 17.4±0.2 (2Θ) and at least one additional peak selected from the group of 10.0±0.2 (2Θ), 16.7±0.2 (2Θ), 26.2±0.2 (2Θ), and 27.1±0.2 (2Θ).

In another preferred embodiment of the invention crystalline form B exhibits in DSC analysis an endothermal event with a peak temperature in the range of 80° C. to 110° C. and/or an exothermal event with a peak temperature in the range of 204° C. to 231° C.

In a further preferred embodiment of the invention crystalline form B has X-ray powder diffraction peaks (CuKα radiation) at 6.8±0.2 (2Θ), 12.1±0.2 (2Θ), 28.3±0.2 (2Θ), and optionally at 18.7±0.2 (2Θ).

It has been surprisingly found that some crystalline forms of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine disclosed herein have surprisingly higher stability than other forms, as is demonstrated in the examples. For instance, crystalline form A achieves significantly and surprisingly higher stability, e.g. physical and/or chemical stability than other crystalline forms.

The stability is important. By using the most stable modification in a medicament it may specifically be ensured that, during storage, no crystalline conversion or polymorphic conversion of the active ingredient in the pharmaceutical formulation takes place. This is advantageous, because otherwise the properties of the medicament could change as a consequence of a conversion of a less stable modification into a more stable modification. In relation to the pharmacological properties of an administration form, this could lead for example to the solubility of the active ingredient changing, accompanied by a change in the release characteristics and thus also a change in the bioavailability. Lastly, this could result in inadequate storage stability of the medicament.

It has been surprisingly found that crystalline form A combines this important property for the use in the formulation of dosage forms with the favorable property that it exists as an ansolvate. This is important because ansolvates represent the crystalline form of a compound which has the lowest weight per mol for that compound, thereby reducing the mass of compound required to achieve a certain dosage in a dosage form, such as a tablet, compared to crystalline forms which bind or cooperate residual solvent.

Suprisingly, it has also been found that of the four crystalline ansolvate forms (A, D, E and H) found, that crystalline form A is the only form of these which shows no tendency to transform into another crystalline form when heated up to its melting point, which lies in the range of about 243-250° C. The relatively high melting point is an additional advantage of crystalline form A. It has furthermore been surprisingly found that crystalline form A exhibits a higher physical and/or chemical stability compared to crystalline ansolvate forms D and E during storage at selected storage conditions, i.e. elevated temperatures and/or high relative humidity. Additionally, crystalline form A was surprisingly found to be chemical more stable during storage at selected storage conditions in mixture with selected pharmaceutical excipients. Details of the properties of crystalline form A and of the other forms according the invention will be discussed in greater detail in the examples below A further aspect of the invention relates to a process for obtaining a crystalline form of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine, comprising the steps of (a-1) suspending cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine in a solvent;

(b-1) separating, preferably filtering off the solid obtained in step (a-1); and (c-1) drying of the solid obtained in step (b-1).

A further aspect of the present invention relates to a crystalline form A.

Preferably, the crystalline form A according to the invention has one or more X-ray powder diffraction peaks selected from the group consisting of about 8.7±0.2 (2Θ), about 11.9±0.2 (2Θ), about 18.3±0.2 (2Θ), and about 27.1±0.2 (2Θ). In a further embodiment the group of X-ray powder diffraction peaks further comprises a peak at about 27.1±0.2 (2Θ).

In some preferred embodiments, the crystalline form has an X-ray powder diffraction peak of about 17.8±0.2 (2Θ). In some preferred embodiments the crystalline form comprises X-ray powder diffraction peaks of about 17.8±0.2 (2Θ), about 11.9±0.2 (2Θ) and/or about 27.1±0.2 (2Θ).

In some preferred embodiments, crystalline form A comprises X-ray powder diffraction peaks of about 18.3±0.2 (2Θ), about 11.9±0.2 (2Θ) and about 27.1±0.2 (2Θ). In further preferred embodiments, crystalline form A may further comprise X-ray powder diffraction peaks of about 17.4±0.2 (2Θ), about 15.3±0.2 (2Θ), 21.9±0.2 (2Θ) and about 16.7±0.2 (2Θ).

In some preferred embodiments, crystalline form A comprises X-ray powder diffraction peaks of about 11.9±0.2 (2Θ), about 17.8±0.2 (2Θ), about 17.4±0.2 (2Θ) and about 18.3±0.2 (2Θ). Optionally, X-ray powder diffraction peaks of about 15.3±0.2 (2Θ), about 21.9±0.2 (2Θ), about 16.7±0.2 (2Θ) and about 27.1±0.2 (2Θ) are comprised.

In another preferred embodiment the crystalline form A according to the invention has one or more X-ray powder diffraction peaks selected from the group consisting of about 8.7±0.2 (2Θ), about 11.9±0.2 (2Θ), about 18.3±0.2 (2Θ), and about 27.1±0.2 (2Θ) and optionally one or more peaks selected from about 15.3±0.2 (2Θ), about 21.9±0.2 (2Θ), about 16.7±0.2 (2Θ) and about 27.1±0.2 (2Θ).

In further preferred embodiments, crystalline form A comprises X-ray powder diffraction peaks of about 11.9±0.2 (2Θ), about 15.3±0.2 (2Θ), about 17.4±0.2 (2Θ), about 17.8±0.2 (2Θ) and about 18.3±0.2 (2Θ). Optionally, an additional X-ray powder diffraction peak of about 27.1±0.2 (2Θ) may be comprised. Also optionally, additional X-ray powder diffraction peaks of about 21.9±0.2 (2Θ), about 16.7±0.2 (2Θ), about 20.3±0.2 (2Θ), and about 19.7±0.2 (2Θ) may be comprised, either in addition to the peak of about 27.1±02 (2Θ) or alternatively.

In further preferred embodiments, crystalline form A comprises X-ray powder diffraction peaks of about 8.7±0.2 (2Θ), about 10.0±0.2 (2Θ), about 11.9±0.2 (2Θ), about 15.3±0.2 (2Θ), about 15.8±0.2 (2Θ), about 16.7±0.2 (2Θ), about 17.4±0.2 (2Θ), about 17.8±0.2 (2Θ), about 18.3±0.2 (2Θ), about 19.7±0.2 (2Θ), about 20.3±0.2 (2Θ), about 21.9±0.2 (2Θ), about 22.2±0.2 (2Θ), and about 27.1±0.2 (2Θ). Optionally, crystalline form A may further comprise one or more X-ray peaks selected from the group consisting of about 7.7±0.2 (2Θ), about 12.3±0.2 (2Θ), about 22.5±0.2 (2Θ) and about 26.2±0.2 (2Θ). In further preferred embodiments, crystalline form A additionally comprises all of the aforementioned optional X-ray peaks.

Although in the X-ray diffractogram of crystalline form A of (E)-2',3',4',9'-Tetrahydro-N,N-dimethyl-4-(3-fluorophenyl)-2'-(2-phenylvinyl)carbonyl-spiro[cyclohexane-1,1' (1'H)-pyrido[3,4-b]indole]-4-amine measured using CuKα radiation having a wavelength of 1.54060 Å the five peaks with the highest relative intensity were found to be about 11.9±0.2 (2Θ), about 15.3±0.2 (2Θ), about 17.4±0.2 (2Θ), about 17.8±0.2 (2Θ) and about 18.3±0.2 (2Θ), in order to discriminate between form A and crystalline forms D, E and H it might be more advantageous to alternatively or additionally look at unique peaks in the X-ray diffractogram, i.e. peaks of sufficient relative intensity at 2Θ-values where forms D, E and H do not show lines with significant intensity. Such characteristic X-ray peaks are besides those of about 15.3±0.2 (2Θ), about 17.4±0.2 (2Θ) and about 18.3±0.2 (2Θ) X-ray peaks of about 7.7±0.2 (2Θ), about 10.0±0.2 (2Θ), about 15.8±0.2 (2Θ), about 21.9±0.2 (2Θ), about 22.2±0.2 (2Θ) and about 27.1±0.2 (2Θ).

Consequently, in some preferred embodiments of the invention crystalline form A comprises at least one X-ray peak selected from the group consisting of about 15.3±0.2 (2Θ), about 17.4±0.2 (2Θ) and about 18.3±0.2 (2Θ) and at least one additional X-ray peak selected from about 7.7±0.2 (2Θ), about 10.0±0.2 (2Θ), about 15.8±0.2 (2Θ), about 21.9±0.2 (2Θ), about 22.2±0.2 (2Θ) and about 27.1±0.2 (2Θ).

Similarly, the X-ray peaks about 16.7±0.2 (2Θ), about 17.4±0.2 (2Θ), about 20.3±0.2 (2Θ), about 22.5±0.2 (2Θ), and about 27.1±0.2 (2Θ) might be more advantageously used to discriminate between crystalline form A and crystalline forms B, C, F and G. Consequently, in some embodiments of the invention crystalline form A comprises at least one X-ray peak at about 17.4±0.2 (2Θ) in combination with at least one X-ray peak selected from about 16.7±0.2 (2Θ), about 20.3±0.2 (2Θ), about 22.5±0.2 (2Θ), and about 27.1±0.2 (2Θ).

Similarly, the X-ray powder diffraction peaks of about 7.7±0.2 (2Θ), about 18.3±0.2 (2Θ), about 21.9±0.2 (2Θ), about 22.2±0.2 (2Θ), about 22.5±0.2 (2Θ), about 26.2±0.2 (2Θ), and about 27.1±0.2 (2Θ) might be more advantageously used to discriminate form A from forms F, I, J, K and L.

Consequently, in some preferred embodiments crystalline form A comprises X-ray powder diffraction peaks of about 18.3±0.2 (2Θ) and about 21.7±0.2 (2Θ) and at least one additional peak selected from the group consisting of about 7.7±0.2 (2Θ), about 21.9±0.2 (2Θ), about 22.2±0.2 (2Θ), about 22.5±0.2 (2Θ), and about 26.2±0.2 (2Θ).

To discriminate between crystalline form A and crystalline B it might be more advantageous to use the X-ray powder diffraction peaks of about 8.7±0.2 (2Θ), about 10.0±0.2 (2Θ), about 16.7±0.2 (2Θ), about 17.4±0.2 (2Θ), about 26.2±0.2 (2Θ), and about 27.1±0.2 (2Θ).

Consequently, in some preferred embodiments of the invention crystalline form A comprises an X-ray peak at about 17.4±0.2 (2Θ) and at least one additional peak selected from the group of about 8.7±0.2 (2Θ), about 10.0±0.2 (2Θ), about 16.7±0.2 (2Θ), about 26.2±0.2 (2Θ), and about 27.1±0.2 (2Θ).

To discriminate between crystalline form A and crystalline form C the X-ray peaks of about 7.7±0.2 (2Θ), about 8.7±0.2 (2Θ), about 15.3±0.2 (2Θ), about 15.8±0.2 (2Θ), about 16.7±0.2 (2Θ), about 17.4±0.2 (2Θ), about 19.7±0.2 (2Θ), about 20.3±0.2 (2Θ), about 21.9±0.2 (2Θ), about 22.2±0.2 (2Θ), about 22.5±0.2 (2Θ) and about 27.1±0.2 (2Θ) might be more advantageously used. Consequently, in a preferred embodiment of the invention, form A comprises the X-ray peak at about 17.4±0.2 (2Θ) and at least one additional peak selected from the group consisting of about 15.3±0.2 (2Θ), about 16.7±0.2 (2Θ), about 20.3±0.2 (2Θ) and about 27.1±0.2 (2Θ). Optionally, one or more X-ray peaks selected from the group consisting of about 7.7±0.2 (2Θ), about 8.7±0.2 (2Θ), about 15.3±0.2 (2Θ), about 19.7±0.2 (2Θ), about 22.2±0.2 (2Θ), and about 22.5±0.2 (2Θ).

To discriminate between crystalline form A and crystalline form D the X-ray peaks of about 7.7±0.2 (2Θ), about 10.0±0.2 (2Θ), about 12.3±0.2 (2Θ), about 15.3±0.2 (2Θ), about 17.8±0.2 (2Θ), about 18.3±0.2 (2Θ), and about 21.9±0.2 (2Θ) might be more advantageously used. Consequently, in a preferred embodiment of the invention, form A comprises at least one of the X-ray peaks selected from at about 15.3±0.2 (2Θ), about 17.4±0.2 (2Θ), about 17.8±0.2 (2Θ) and about 18.3±0.2 (2Θ) and at least one additional X-ray peak selected from the group consisting of about 7.7±0.2 (2Θ), about 10.0±0.2 (2Θ), about 12.3±0.2 (2Θ), and about 21.9±0.2 (2Θ).

In order to discriminate between crystalline form A and crystalline form E it might be more advantageous not to rely on the X-ray peak of about 18.3±0.2 (2Θ), because both polymorphic form A and E show an X-ray peak of high intensity in this area. Consequently, in a preferred embodiment of the invention, form A comprises at least one X-ray peak selected about 11.9±0.2 (2Θ), about 15.3±0.2 (2Θ), about 17.4±0.2 (2Θ), and about 17.8±0.2 (2Θ), and at least one X-ray peak selected from the group consisting of about 7.7±0.2 (2Θ), about 8.7±0.2 (2Θ), about 10.0±0.2 (2Θ), about 11.9±0.2 (2Θ), about 12.3±0.2 (2Θ), about 15.3±0.2 (2Θ), about 15.8±0.2 (2Θ), about 16.7±0.2 (2Θ), about 17.4±0.2 (2Θ), about 19.7±0.2 (2Θ), about 20.3±0.2 (2Θ), about 21.9±0.2 (2Θ), about 22.2±0.2 (2Θ), about 22.5±0.2 (2Θ), about 26.2±0.2 (2Θ) and about 27.1±0.2 (2Θ).

To discriminate between crystalline form A and crystalline form F, the X-ray peaks of about 7.7±0.2 (2Θ), about 10.0±0.2 (2Θ), about 11.9±0.2 (2Θ), about 15.3±0.2 (2Θ), about 15.8±0.2 (2Θ), about 17.4±0.2 (2Θ), about 17.8±0.2 (2Θ), about 19.7±0.2 (2Θ), about 20.3±0.2 (2Θ), about 21.9±0.2 (2Θ), about 22.2±0.2 (2Θ), about 22.5±0.2 (2Θ) and about 27.1±0.2 (2Θ) might be more advantageously used. Consequently, in a preferred embodiment of the invention, form A comprises at least one X-ray peak selected from about 11.9±0.2 (2Θ), about 15.8±0.2 (2Θ), and about 17.8±0.2 (2Θ) and at least one additional peak selected from the group consisting of about 7.7±0.2 (2Θ), about 10.0±0.2 (2Θ), about 15.3±0.2 (2Θ), about 17.4±0.2 (2Θ), about 19.7±0.2 (2Θ), about 20.3±0.2 (2Θ), about 21.9±0.2 (2Θ), about 22.2±0.2 (2Θ), about 22.5±0.2 (2Θ) and about 27.1±0.2 (2Θ).

To discriminate between crystalline form A and crystalline form G, the X-ray peaks of about 7.7±0.2 (2Θ), about 16.7±0.2 (2Θ), about 20.3±0.2 (2Θ), about 21.9±0.2 (2Θ), about 22.2±0.2 (2Θ), about 22.5±0.2 (2Θ), about 26.2±0.2 (2Θ) and about 27.1±0.2 (2Θ) might be more advantageously used. Consequently, in a preferred embodiment of the invention, form A comprises at least one or more X-ray powder diffraction peaks selected from the group consisting of about 11.9±0.2 (2Θ), about 15.3±0.2 (2Θ), about 17.4±0.2 (2Θ), about 17.8±0.2 (2Θ) and about 18.3±0.2 and at least one additional peak selected from the group consisting of about 7.7±0.2 (2Θ), about 16.7±0.2 (2Θ), about 20.3±0.2 (2Θ), about 21.9±0.2 (2Θ), about 22.2±0.2 (2Θ), about 22.5±0.2 (2Θ), about 26.2±0.2 (2Θ) and about 27.1±0.2 (2Θ).

To discriminate between crystalline form A and crystalline form H, the X-ray peaks of about 7.7±0.2 (2Θ), about 8.7±0.2 (2Θ), about 11.9±0.2 (2Θ), about 12.3±0.2 (2Θ), about 15.3±0.2 (2Θ), about 15.8±0.2 (2Θ), about 16.7±0.2 (2Θ), about 21.9±0.2 (2Θ), about 22.2±0.2 (2Θ), about 26.2±0.2 (2Θ) and about 27.1±0.2 (2Θ) might be more advantageously used. Consequently, in a preferred embodiment of the invention, form A comprises at least one or more X-ray powder diffraction peaks selected from the group consisting of about 11.9±0.2 (2Θ) and about 15.3±0.2 (2Θ) and at least one additional peak selected from the group consisting of about 7.7±0.2 (2Θ), about 8.7±0.2 (2Θ), about 12.3±0.2 (2Θ), about 15.8±0.2 (2Θ), about 16.7±0.2 (2Θ), about 21.9±0.2 (2Θ), about 22.2±0.2 (2Θ), about 26.2±0.2 (2Θ) and about 27.1±0.2 (2Θ).

To discriminate between crystalline form A and crystalline form I, the X-ray peaks of about 7.7±0.2 (2Θ), about 8.7±0.2 (2Θ), about 20.3±0.2 (2Θ), about 22.2±0.2 (2Θ), and about 27.1±0.2 (2Θ) might be more advantageously used. Consequently, in a preferred embodiment of the invention, form A comprises at least one or more X-ray powder diffraction peaks selected from the group consisting of about 11.9±0.2 (2Θ), about 15.3±0.2 (2Θ), about 17.4±0.2 (2Θ), about 17.8±0.2 (2Θ) and about 18.3±0.2 (2Θ), and at least one additional peak selected from the group consisting of about 7.7±0.2 (2Θ), about 8.7±0.2 (2Θ), about 20.3±0.2 (2Θ), about 22.2±0.2 (2Θ), and about 27.1±0.2 (2Θ).

To discriminate between crystalline form A and crystalline form J, the X-ray peaks of about 7.7±0.2 (2Θ), about 8.7±0.2 (2Θ), about 10.0±0.2 (2Θ), about 11.9±0.2 (2Θ), about 15.8±0.2 (2Θ), about 21.9±0.2 (2Θ), about 22.2±0.2 (2Θ), about 22.5±0.2 (2Θ), and about 27.1±0.2 (2Θ) might be more advantageously used. Consequently, in a preferred embodiment of the invention, form A comprises at least one or more X-ray powder diffraction peaks selected from the group consisting of about 11.9±0.2 (2Θ) and 15.8±0.2 (2Θ), and at least one additional peak selected from the group consisting of 7.7±0.2 (2Θ), about 8.7±0.2 (2Θ), about 10.0±0.2 (2Θ), about 21.9±0.2 (2Θ), about 22.2±0.2 (2Θ), about 22.5±0.2 (2Θ), and about 27.1±0.2 (2Θ)

To discriminate between crystalline form A and crystalline form K, the X-ray peaks of about 7.7±0.2 (2Θ), about 8.7±0.2 (2Θ), about 11.9±0.2 (2Θ), about 12.3±0.2 (2Θ), about 17.4±0.2 (2Θ), about 17.8±0.2 (2Θ), about 18.3±0.2 (2Θ), about 21.9±0.2 (2Θ), and about 26.2±0.2 (2Θ) might be more advantageously used. Consequently, in a preferred embodiment of the invention, form A comprises at least one or more X-ray powder diffraction peaks selected from the group consisting of 11.9±0.2 (2Θ), about 17.4±0.2 (2Θ), about 17.8±0.2 (2Θ) and about 18.3±0.2 and at least one additional peak selected from the group consisting of 7.7±0.2 (2Θ), about 8.7±0.2 (2Θ), about 12.3±0.2 (2Θ), about 21.9±0.2 (2Θ), and about 26.2±0.2 (2Θ).

To discriminate between crystalline form A and crystalline form L, the X-ray peaks of about 8.7±0.2 (2Θ), about 10.0±0.2 (2Θ), about 15.3±0.2 (2Θ), about 15.8±0.2 (2Θ), about 22.5±0.2 (2Θ), and about 27.1±0.2 (2Θ) might be more advantageously used. Consequently, in a preferred embodiment of the invention, form A comprises an X-ray peak of about 15.3±0.2 and at least one additional peak selected from the group consisting of 8.7±0.2 (2Θ), about 10.0±0.2 (2Θ), about 15.8±0.2 (2Θ), about 22.5±0.2 (2Θ), and about 27.1±0.2 (2Θ).

Crystalline form A according to the invention may further be characterized that it has a Raman peak at about 1606 $cm^{-1}$ and/or at least one Raman peak selected from the group of about 1175 $cm^{-1}$, about 1568 $cm^{-1}$, about 1574 $cm^{-1}$ and about 1650 $cm^{-1}$.

Crystalline form A according to the invention may further be characterized that it has a Raman peak at about 1606 $cm^{-1}$ and/or at least one Raman peak selected from the group of about 1175 $cm^{-1}$, about 1568 $cm^{-1}$, about 1574 $cm^{-1}$ and about 1650 $cm^{-1}$ and/or at least one Raman peak selected from the group of about 98 $cm^{-1}$ and about 1001 $cm^{-1}$. Additionally, it may have at least one Raman peak selected from the group consisting of about 128 $cm^{-1}$, about 170 $cm^{-1}$, about 676 $cm^{-1}$, about 1183 $cm^{-1}$, about 1204 $cm^{-1}$, about 1268 $cm^{-1}$, about 1294 $cm^{-1}$, about 1447 $cm^{-1}$, about 1462 $cm^{-1}$, about 1584 $cm^{-1}$, about 2910 $cm^{-1}$, about 3062 $cm^{-1}$, and about 3075 $cm^{-1}$. Also additionally, crystalline form A may have at least one Raman peak selected from the group consisting of about 189 $cm^{-1}$, about 227 $cm^{-1}$, about 272 $cm^{-1}$, about 310 $cm^{-1}$, about 355 $cm^{-1}$, about 417 $cm^{-1}$, about 461 $cm^{-1}$, about 485 $cm^{-1}$, about 509 $cm^{-1}$, about 543 $cm^{-1}$, about 589 $cm^{-1}$, about 611 $cm^{-1}$, about 620 $cm^{-1}$, about 644 $cm^{-1}$, about 697 $cm^{-1}$, about 725 $cm^{-1}$, about 746 $cm^{-1}$, about 783 $cm^{-1}$, about 801 $cm^{-1}$, about 831 $cm^{-1}$, about 865 $cm^{-1}$, about 893 $cm^{-1}$, about 927 $cm^{-1}$, about 955 $cm^{-1}$, about 978 $cm^{-1}$, about 1012 $cm^{-1}$, about 1028 $cm^{-1}$, about 1048 $cm^{-1}$, about 1074 $cm^{-1}$, about 1111 $cm^{-1}$, about 1155 $cm^{-1}$, about 1244 $cm^{-1}$, about 1343 $cm^{-1}$, about 1368 $cm^{-1}$, about 1385 $cm^{-1}$, about 1407 $cm^{-1}$, about 1493 $cm^{-1}$, about 2782 $cm^{-1}$, about 2834 $cm^{-1}$, about 2878 $cm^{-1}$, about 2946 $cm^{-1}$, about 2960 $cm^{-1}$, about 2980 $cm^{-1}$, about 2999 $cm^{-1}$, about 3026 $cm^{-1}$ and about 3449 $cm^{-1}$.

In DSC analyses, crystalline form A according to the present invention preferably exhibits an endothermal event with a peak temperature of about 235-255° C. (i.e. the crystalline form has a melting endotherm at about 235-255° C.), more preferably of about 237-250° C., still more preferably of about 240-248° C. In some preferred embodiments crystalline form A exhibits an endothermal event with a peak temperature of about 242-248° C.

A further aspect of the present invention relates to a crystalline form B

Preferably, the crystalline form B according to the invention has one or more X-ray powder diffraction peaks selected from the group consisting of about 6.8±0.2 (2Θ), about 12.1±0.2 (2Θ), about 18.7±0.2 (2Θ), and about 28.3±0.2 (2Θ).

In a further embodiment the group of X-ray powder diffraction peaks further comprises a peak at about 28.3±0.2 (2Θ). In some preferred embodiments, the crystalline form has an X-ray powder diffraction peak of about 12.1±0.2 (2Θ). In some preferred embodiments the crystalline form comprises X-ray powder diffraction peaks of about 12.1±0.2 (2Θ), about 18.7±0.2 (2Θ) and/or about 28.3±0.2 (2Θ).

In some preferred embodiments, crystalline form B comprises X-ray powder diffraction peaks of about 12.1±0.2 (2Θ), about 18.0±0.2 (2Θ) and about 18.7±0.2 (2Θ), and optionally, a further peak at about 28.3±0.2 (2Θ). In further preferred embodiments, crystalline form B may further comprise X-ray powder diffraction peaks of about 6.8±0.2 (2Θ), about 18.4±0.2 (2Θ), about 19.8±0.2 (2Θ).

Although in the X-ray diffractogram of crystalline form B of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine measured using CuKα radiation having a wavelength of 1.54060 Å the five peaks with the highest relative intensity were found to be about 12.1±0.2 (2Θ), about 18.0±0.2 (2Θ) and about 18.7±0.2 (2Θ), about 18.4±0.2 (2Θ), and about 19.8±0.2 (2Θ), in order to discriminate this form over crystalline forms A, D, E and H it might be more advantageous to alternatively or additionally look at unique peaks in the X-ray diffractogram, i.e. peaks of sufficient relative intensity at 2Θ-values where forms A, D, E and H do not show lines with significant intensity. Such characteristic X-ray peaks are those of about 13.7±0.2 (2Θ) and about 14.2±0.2 (2Θ).

Consequently, in some preferred embodiments of the invention crystalline form B comprises at least one X-ray peak selected from about 13.7±0.2 (2Θ) and about 14.2±0.2 (2Θ).

Similarly, the X-ray peaks of about 12.1±0.2 (2Θ), about 15.5±0.2 (2Θ), about 19.8±0.2 (2Θ), about 22.1±0.2 (2Θ), and about 28.3±0.2 (2Θ) might be more advantageously used to discriminate crystalline form B over crystalline forms C, F and G. Consequently, in some embodiments of the invention crystalline form B comprises at least one X-ray peak selected from the peaks of about 12.1±0.2 (2Θ) and about 19.8±0.2 (2Θ) in combination with at least one X-ray peak selected from the group of peaks consisting of about 15.5±0.2 (2Θ), about 22.1±0.2 (2Θ) and about 28.3±0.2 (2Θ).

To discriminate between crystalline form B and crystalline form A the X-ray peaks of about 6.8±0.2 (2Θ), about 13.7±0.2 (2Θ), about 14.2±0.2 (2Θ), about 18.7±0.2 (2Θ), and about 28.3±0.2 (2Θ) might be more advantageously used. Consequently, in a preferred embodiment of the invention, form B comprises the X-ray peak at about 18.7±0.2 (2Θ) in combination with one or more X-ray peaks from the group consisting of about 6.8±0.2 (2Θ), about 13.7±0.2 (2Θ), about 14.2±0.2 (2Θ) and about 28.3±0.2 (2Θ).

In some preferred embodiments, crystalline form B comprises X-ray powder diffraction peaks of about 12.1±0.2 (2Θ), about 18.0±0.2 (2Θ), about 18.4±0.2 (2Θ), and about 18.7±0.2 (2Θ). Optionally, X-ray powder diffraction peaks of about 6.8±0.2 (2Θ), about 14.2±0.2 (2Θ), about 19.8±0.2 (2Θ), and about 28.3±0.2 (2Θ), are comprised.

In further preferred embodiments, the crystalline form B according to the invention comprises the X-ray powder diffraction peaks of about 6.8±0.2 (2Θ), about 12.1±0.2 (2Θ), about 18.7±0.2 (2Θ), and about 28.3±0.2 (2Θ), optionally with one or more additional peaks selected from about 14.2±0.2 (2Θ), about 18.0±0.2 (2Θ), about 18.4±0.2 (2Θ), about 19.8±0.2 (2Θ), and about 28.3±0.2 (2Θ).

In further preferred embodiments, crystalline form B comprises X-ray powder diffraction peaks of about 12.1±0.2 (2Θ), about 18.0±0.2 (2Θ), about 18.4±0.2 (2Θ), about 18.7±0.2 (2Θ), and about 19.8±0.2 (2Θ). Optionally, an additional X-ray powder diffraction peak of about 28.3±0.2 (2Θ) may be comprised. Also optionally, additional X-ray powder diffraction peaks of about 6.8±0.2 (2Θ), about 14.2±0.2 (2Θ), about 20.8±0.2 (2Θ), and about 15.6±0.2 (2Θ) may be comprised, either in addition to the peak of about 28.3±02 (2Θ) or alternatively. Optionally, in some preferred embodiments, crystalline form B comprises at least one additional X-ray powder diffraction peak selected from of about 7.4±0.2 (2Θ), about 22.1±0.2 (2Θ) and about 13.7±0.2 (2Θ). In preferred embodiments, crystalline form A comprises all of the aforementioned optional additional X-ray peaks.

Crystalline form B according to the invention may further be characterized that it has a Raman peak at about 1643 $cm^{-1}$ and/or one Raman peak at about 1578 $cm^{-1}$.

Crystalline form B according to the invention may further be characterized that it has a Raman peak at about 1643 $cm^{-1}$ and/or one Raman peak at about 1578 $cm^{-1}$ and/or one peak selected from the group of about 1601 $cm^{-1}$, about 84 $cm^{-1}$, about 109 $cm^{-1}$, about 1001 $cm^{-1}$, about 1618 $cm^{-1}$, about 1563 $cm^{-1}$, about 1643 $cm^{-1}$, and about 3063 $cm^{-1}$.

Additionally, crystalline form B may have one or more Raman peaks selected from the group consisting of about 166 $cm^{-1}$, about 220 $cm^{-1}$, about 272 $cm^{-1}$, about 619 $cm^{-1}$, about 676 $cm^{-1}$, about 781 $cm^{-1}$, about 862 $cm^{-1}$, about 888 $cm^{-1}$, about 976 $cm^{-1}$, about 1010 $cm^{-1}$, about 1029 $cm^{-1}$, about 1047 $cm^{-1}$, about 1158 $cm^{-1}$, about 1180 $cm^{-1}$, about 1203 $cm^{-1}$, about 1266 $cm^{-1}$, about 1300 $cm^{-1}$, about 1441 $cm^{-1}$, about 1449 $cm^{-1}$, about 1465 $cm^{-1}$, about 1578 $cm^{-1}$, about 2935 $cm^{-1}$, about 2967 $cm^{-1}$ and about 3001 $cm^{-1}$.

Also additionally, crystalline form B may have one or more Raman peaks selected from the group consisting of about 333 $cm^{-1}$, about 365 $cm^{-1}$, about 387 $cm^{-1}$, about 405 $cm^{-1}$, about 435 $cm^{-1}$, about 463 $cm^{-1}$, about 505 $cm^{-1}$, about 541 $cm^{-1}$, about 590 $cm^{-1}$, about 643 $cm^{-1}$, about 725 $cm^{-1}$, about 745 $cm^{-1}$, about 802 $cm^{-1}$, about 834 $cm^{-1}$, about 929 $cm^{-1}$, about 1087 $cm^{-1}$, about 1112 $cm^{-1}$, about 1326 $cm^{-1}$, about 1341 $cm^{-1}$, about 1373 $cm^{-1}$, about 1405 $cm^{-1}$, about 1861 $cm^{-1}$, about 2136 $cm^{-1}$, about 2172 $cm^{-1}$, about 2328 $cm^{-1}$, about 2489 $cm^{-1}$, about 2519 $cm^{-1}$, about 2558 $cm^{-1}$, about 2772 $cm^{-1}$, about 2794 $cm^{-1}$, about 2843 $cm^{-1}$, about 2890 $cm^{-1}$, about 3153 $cm^{-1}$, about 3197 $cm^{-1}$, about 3243 $cm^{-1}$, about 3323 $cm^{-1}$ and about 3459 $cm^{-1}$.

In DSC analyses, crystalline form B according to the present invention preferably exhibits an endothermal event with a peak temperature of about 80-110° C., preferably of about 80-95° C., and/or an endothermal event with a peak temperature of about 230 to 255, preferably of about 237-250° C., more preferably of about 240-248° C. In some preferred embodiments crystalline form B exhibits an endothermal event with a peak temperature of about 242-248° C. Additionally, crystalline form B preferably exhibits an exothermal event with a peak temperature of about 140-150° C., preferably 142 to 148° C., more preferably 143-147° C., and/or an exothermal event with a peak temperature of about 200-230° C., preferably about 205-230° C.

A further aspect of the present invention relates to a crystalline form C.

Preferably, the crystalline form C according to the invention has one or more X-ray powder diffraction peaks selected from the group consisting of about 9.7±0.2 (2Θ), about 11.6±0.2 (2Θ), about 14.0±0.2 (2Θ), and about 17.9±0.2 (2Θ).

In some preferred embodiments, the crystalline form C has an X-ray powder diffraction peak of about 17.9±0.2 (2Θ). In some preferred embodiments the crystalline form comprises X-ray powder diffraction peaks of about 17.9±0.2 (2Θ), about 14.0±0.2 (2Θ) and/or about 13.0±0.2 (2Θ).

In some preferred embodiments, crystalline form C comprises X-ray powder diffraction peaks of 17.9±0.2 (2Θ), about 14.0±0.2 (2Θ) and about 13.0±0.2 (2Θ). In further preferred embodiments, crystalline form C may further comprise X-ray powder diffraction peaks of about 7.1±0.2 (2Θ), about 9.7±0.2 (2Θ), about 11.6±0.2 (2Θ), and about 12.5±0.2 (2Θ).

To discriminate between crystalline form C and crystalline form A of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine it might be more advantageous to alternatively or additionally look at unique peaks in the X-ray diffraction diagram of C compared to the X-ray diffraction diagram of A. Such characteristic X-ray peaks are besides those of about 9.7±0.2 (2Θ), about 13.0±0.2 (2Θ), and about 14.0±0.2 (2Θ) X-ray peaks of about 7.0±0.2 (2Θ), about 7.1±0.2 (2Θ), at about 11.3±0.2 (2Θ), at about 14.3±0.2 (2Θ), at about 21±0.2 (2Θ) and at about 21.1±0.2 (2Θ).

Consequently, in some preferred embodiments of the invention crystalline form C comprises at least one X-ray peak selected from the group consisting of about 9.7±0.2 (2Θ), about 13.0±0.2 (2Θ), and about 14.0±0.2 (2Θ) and at least one additional X-ray peak selected from about 7.0±0.2 (2Θ), about 7.1±0.2 (2Θ), at about 11.3±0.2 (2Θ), at about 14.3±0.2 (2Θ), at about 21±0.2 (2Θ) and at about 21.1±0.2 (2Θ).

In some preferred embodiments, crystalline form C comprises X-ray powder diffraction peaks of about 17.9±0.2 (2Θ), about 14.0±0.2 (2Θ), about 13.0±0.2 (2Θ) and about 11.6±0.2 (2Θ). Optionally, X-ray powder diffraction peaks of about 7.1±0.2 (2Θ), of about 9.7±0.2 (2Θ), about 12.5±0.2 (2Θ) and of about 14.3±0.2 (2Θ) are further comprised.

In further preferred embodiments, the crystalline form C according to the invention comprises X-ray powder diffraction peaks at about 9.7±0.2 (2Θ), about 11.6±0.2 (2Θ), about 14.0±0.2 (2Θ), and about 17.9±0.2 (2Θ) and optionally one or more peaks selected from the group consisting of about 7.1±0.2 (2Θ), about 12.5±0.2 (2Θ), of about 13.0±0.2 (2Θ) and of about 14.3±0.2 (2Θ).

In further preferred embodiments, crystalline form C comprises X-ray powder diffraction peaks of about 17.9±0.2 (2Θ), about 14.0±0.2 (2Θ), 13.0±0.2 (2Θ), about 11.6±0.2 (2Θ) and about 9.7±0.2 (2Θ). Optionally, an additional X-ray powder diffraction peak of about 12.5±0.2 (2Θ) may be comprised. Also optionally, additional X-ray powder diffraction peaks of about 7.1±0.2 (2Θ), about 11.3±0.2 (2Θ), and about 14.3±0.2 (2Θ) may be comprised, either in addition to the peak of about 12.5±02 (2Θ) or alternatively.

In further preferred embodiments, crystalline form C comprises X-ray powder diffraction peaks of about 7.0±0.2 (2Θ), about 7.1±0.2 (2Θ), about 9.7±0.2 (2Θ), about 11.3±0.2 (2Θ), about 11.6±0.2 (2Θ), about 12.5±0.2 (2Θ), about 13.0±0.2 (2Θ), about 14.0±0.2 (2Θ), about 14.3±0.2 (2Θ), about 17.9±0.2 (2Θ), and about 21.0±0.2 (2Θ). Optionally, crystalline form C may further comprise one or more X-ray peaks selected from the group consisting of about 21.1±0.2 (2Θ) and/or about 26.3. In some preferred embodiments, crystalline form C additionally comprises all of the aforementioned optional X-ray peaks.

In DSC analyses, crystalline form C according to the present invention preferably exhibits an endothermal event with a peak temperature of about 60-150° C., preferably of about 100-150° C., more preferably of about 120-150° C., and/or an endothermal event with a peak temperature of about 230 to 255, preferably of about 237-250° C., more preferably of about 240-248° C. In some preferred embodiments crystalline form B exhibits an endothermal event with a peak temperature of about 242-248° C. Additionally, crystalline form C preferably exhibits an exothermal event with a peak temperature of about 175-220° C., preferably 175-215° C., more preferably 175-210° C.

A further aspect of the present invention relates to a crystalline form D.

Preferably, the crystalline form D according to the invention has one or more X-ray powder diffraction peaks selected from the group consisting of about 8.7±0.2 (2Θ), about 11.6±0.2 (2Θ), about 16.6±0.2 (2Θ), about and 21.2±0.2 (2Θ).

In some preferred embodiments, the crystalline form D has an X-ray powder diffraction peak of about 8.7±0.2 (2Θ). In some preferred embodiments the crystalline form comprises X-ray powder diffraction peaks of about 8.7±0.2 (2Θ), about 16.6±0.2 (2Θ) and/or about 21.2±0.2 (2Θ).

In some preferred embodiments, crystalline form D comprises X-ray powder diffraction peaks of about 8.7±0.2 (2Θ), about 16.6±0.2 (2Θ) and about 21.2±0.2 (2Θ). In further preferred embodiments, crystalline form D may further comprise X-ray powder diffraction peaks of about 17.2±0.2 (2Θ), about 11.6±0.2 (2Θ), about 20.0±0.2 (2Θ) and about 11.0±0.2 (2Θ).

To discriminate between crystalline form D and crystalline form A of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine it might be more advantageous to alternatively or additionally look at unique peaks in the X-ray diffraction diagram of D compared to the X-ray diffraction diagram of A. Such a characteristic X-ray peak is the one of about 21.2±0.2 (2Θ).

Consequently, in some preferred embodiments of the invention crystalline form D comprises at least one X-ray peak selected from the group consisting of about 8.7±0.2 (2Θ), about 11.6±0.2 (2Θ), about 16.6±0.2 (2Θ), about 17.2±0.2 (2Θ), and the additional X-ray peak of about and about 21.2±0.2 (2Θ).

In some preferred embodiments, crystalline form D comprises X-ray powder diffraction peaks of about 8.7±0.2 (2Θ), about 16.6±0.2 (2Θ), about 17.2±0.2 (2Θ) and about 21.2±0.2 (2Θ). Optionally, X-ray powder diffraction peaks of about 11.6±0.2 (2Θ), about 20.0±0.2 (2Θ), about 11.0±0.2 (2Θ), and about 17.6±0.2 (2Θ) may be further comprised.

In further preferred embodiments, crystalline form D comprises X-ray powder diffraction peaks of about 8.7±0.2 (2Θ), about 11.6±0.2 (2Θ), about 16.6±0.2 (2Θ), about and 21.2±0.2 (2Θ) and optionally, X-ray powder diffraction peaks of about 11.0±0.2 (2Θ), about 17.2±0.2 (2Θ), about 17.6±0.2 (2Θ), and about 20.0±0.2 (2Θ) may be further comprised.

In further preferred embodiments, crystalline form D comprises X-ray powder diffraction peaks of about 8.7±0.2 (2Θ), about 16.6±0.2 (2Θ), about 21.2±0.2 (2Θ), about 17.2±0.2 (2Θ) and about 11.6±0.2 (2Θ). Optionally, an additional X-ray powder diffraction peak of about 20.0±0.2 (2Θ) may be comprised. Also optionally, additional X-ray powder diffraction peaks of about 11.0±0.2 (2Θ), about 17.6±0.2 (2Θ), and/or about 18.2±0.2 (2Θ) and/or about 22.7±0.2 (2Θ) and/or about 11.3±0.2 (2Θ) and/or about 12.5±0.2 (2Θ) and/or about 26.4.2±0.2 (2Θ) may be comprised, either in addition to the peak of about 20.0±02 (2Θ) or alternatively.

Crystalline form D according to the invention may further be characterized that it has a Raman peak at about 1612 cm$^{-1}$ and/or one Raman peak at about 1199 cm$^{-1}$.

Crystalline form D according to the invention may further be characterized that it has a Raman peak at about 1612 cm$^{-1}$ and/or one Raman peak at about 1199 cm$^{-1}$ and/or one peak selected from the group of about 84 cm$^{-1}$, about 121 cm$^{-1}$, about 158 cm$^{-1}$, about 1000 cm$^{-1}$, about 1563 cm$^{-1}$, and about 1599 cm$^{-1}$.

Additionally, crystalline form D may have one or more Raman peaks selected from the group consisting of about 237 cm$^{-1}$, about 268 cm$^{-1}$, about 294 cm$^{-1}$, about 335 cm$^{-1}$, about 372 cm$^{-1}$, about 402 cm$^{-1}$, about 434 cm$^{-1}$, about 466 cm$^{-1}$, about 489 cm$^{-1}$, about 503 cm$^{-1}$, about 542 cm$^{-1}$, about 618 cm$^{-1}$, about 675 cm$^{-1}$, about 782 cm$^{-1}$, about 886 cm$^{-1}$, about 1011 cm$^{-1}$, about 1030 cm$^{-1}$, about 1056 cm$^{-1}$, about 1154 cm$^{-1}$, about 1171 cm$^{-1}$, about 1199 cm$^{-1}$, about 1263 cm$^{-1}$, about 1289 cm$^{-1}$, about 1325 cm$^{-1}$, about 1447 cm$^{-1}$, about 1464 cm$^{-1}$, about 1576 cm$^{-1}$, about 1644 cm$^{-1}$, about 2946 cm$^{-1}$, about 2980 cm$^{-1}$, about 3010 cm$^{-1}$ and about 3065 cm$^{-1}$.

Also additionally, crystalline form D may have one or more Raman peaks of about 579 cm$^{-1}$, about 646 cm$^{-1}$, about 696 cm$^{-1}$, about 711 cm$^{-1}$, about 727 cm$^{-1}$, about 799 cm$^{-1}$, about 834 cm$^{-1}$, about 867 cm$^{-1}$, about 921 cm$^{-1}$, about 970 cm$^{-1}$, about 1085 cm$^{-1}$, about 1115 cm$^{-1}$, about 1343 cm$^{-1}$, about 1377 cm$^{-1}$, about 1406 cm$^{-1}$, about 2792 cm$^{-1}$, about 2846 cm$^{-1}$, about 2895 cm$^{-1}$, about 3152 and about 3196 cm$^{-1}$.

In DSC analyses, crystalline form D according to the present invention preferably exhibits an endothermal event with a peak temperature of about 140-180° C., preferably of about 145-170° C., more preferably of about 145-165° C., and/or an endothermal event with a peak temperature of about 230 to 255, preferably of about 237-250° C., more preferably of about 240-248° C. In some preferred embodiments crystalline form B exhibits an endothermal event with a peak temperature of about 242-248° C. Additionally, crystalline form D preferably exhibits an exothermal event with a peak temperature of about 200-230° C., preferably 205-225° C.

A further aspect of the present invention relates to a crystalline form E.

Preferably, the crystalline form E according to the invention has one or more X-ray powder diffraction peaks selected from the group consisting of about 6.9±0.2 (2Θ), about 8.1±0.2 (2Θ), about 18.3±0.2 (2Θ), and about 20.8±0.2 (2Θ).

In some preferred embodiments, the crystalline form E has an X-ray powder diffraction peak of about 18.3±0.2 (2Θ). In some preferred embodiments the crystalline form comprises X-ray powder diffraction peaks of about 18.3±0.2 (2Θ), about 6.9.0±0.2 (2Θ) and/or about 8.1±0.2 (2Θ).

In some preferred embodiments, crystalline form E comprises X-ray powder diffraction peaks of about 18.3±0.2 (2Θ), about 6.9±0.2 (2Θ), and about 8.1±0.2 (2Θ). In further preferred embodiments, crystalline form E may further comprise X-ray powder diffraction peaks of about 20.8±0.2 (2Θ), about 10.4±0.2 (2Θ), and about 13.8±0.2 (2Θ).

To discriminate between crystalline form E and crystalline form A cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine it might be more advantageous to alternatively or additionally look at unique peaks in the X-ray diffraction diagram of E compared to the X-ray diffraction diagram of A. Such characteristic X-ray peaks are besides those of about 6.9±0.2 (2Θ), about 8.1±0.2 (2Θ) and about 20.8±0.2 (2Θ) X-ray peaks of about 13.7±0.2 (2Θ), about 28.1±0.2 (2Θ), about 13.9±0.2 (2Θ), about 21.1±0.2 (2Θ), and about 19.0±0.2 (2Θ).

Consequently, in some preferred embodiments of the invention crystalline form C comprises at least one X-ray peak selected from the group consisting of about 6.9±0.2 (2Θ), about 8.1±0.2 (2Θ) and about 20.8±0.2 (2Θ) and at least one additional X-ray peak selected from about 13.7±0.2 (2Θ), about 28.1±0.2 (2Θ), about 13.9±0.2 (2Θ), about 21.1±0.2 (2Θ), and about 19.0±0.2 (2Θ).

In some preferred embodiments, crystalline form E comprises X-ray powder diffraction peaks of about 6.9±0.2 (2Θ), about 8.1±0.2 (2Θ), about 18.3±0.2 (2Θ) and about 20.8±0.2 (2Θ). Optionally, X-ray powder diffraction peaks of about 10.4±0.2 (2Θ), about 13.8±0.2 (2Θ), about 28.1±0.2 (2Θ), and/or about 13.9±0.2 (2Θ) and/or about 17.9±0.2 (2Θ) are further comprised.

In further preferred embodiments, crystalline form E comprises X-ray powder diffraction peaks of about 6.9±0.2 (2Θ), about 8.1±0.2 (2Θ), about 18.3±0.2 (2Θ), about 20.8±0.2 (2Θ), and about 10.4±0.2 (2Θ). Optionally, and X-ray powder diffraction peak of about 13.8±0.2 (2Θ) may be comprised. Also optionally, additional X-ray powder diffraction peaks of about 28.1±0.2 (2Θ), about 13.9±0.2 (2Θ), about 17.9±0.2 (2Θ) and about 16.9±0.2 (2Θ) may be comprised, either in addition to the peak of about 13.8±02 (2Θ) or alternatively.

In further preferred embodiments, crystalline form E comprises X-ray powder diffraction peaks of about 6.9±0.2 (2Θ), about 8.1±0.2 (2Θ), about 10.4±0.2 (2Θ), about 12.1±0.2 (2Θ), about 13.8±0.2 (2Θ), about 13.9±0.2 (2Θ), about 16.4±0.2 (2Θ), 16.6±0.2 (2Θ), about 16.9±0.2 (2Θ), about 17.9±0.2 (2Θ), about 18.3±0.2 (2Θ), about 18.7±0.2 (2Θ), about 19.0±0.2 (2Θ), about 20.8±0.2, about 21.1±0.2 (2Θ), about 27.5±0.2 (2Θ), and about 28.1±0.2 (2Θ).

In DSC analyses, crystalline form E according to the present invention preferably exhibits an endothermal event with a peak temperature of about 135-150° C., preferably of about 140-150° C., more preferably of about 143-146° C., and/or an endothermal event with a peak temperature of about 230 to 255, preferably of about 237-250° C., more preferably of about 240-248° C. In some preferred embodiments crystalline form E exhibits an endothermal event with a peak temperature of about 242-248° C. Additionally, crystalline form E preferably exhibits an exothermal event with a peak temperature of about 190-210° C., preferably about 197-212° C.

A further aspect of the present invention relates to a crystalline form F.

Preferably, the crystalline form F according to the invention has one or more X-ray powder diffraction peaks selected from the group consisting of about 8.7±0.2 (2Θ), about 12.5±0.2 (2Θ), and 20.9±0.2 (2Θ).

In some preferred embodiments, the crystalline form F has an X-ray powder diffraction peak of about 12.5±0.2 (2Θ). In some preferred embodiments the crystalline form comprises X-ray powder diffraction peaks of about 8.7±0.2 (2Θ), about 12.5±0.2 (2Θ) and/or about 20.9±0.2 (2Θ).

In some preferred embodiments, crystalline form F comprises X-ray powder diffraction peaks of about 8.7±0.2 (2Θ), about 12.5±0.2 (2Θ) and about 20.9±0.2 (2Θ). In further preferred embodiments, crystalline form F may further comprise one or more X-ray powder diffraction peaks selected from the groups consisting of about 11.3±0.2 (2Θ), about 16.7±0.2 (2Θ), about 25.2±0.2 (2Θ) and about 25.9±0.2 (2Θ).

In some preferred embodiments, crystalline form F comprises at least on X-ray powder diffraction peak selected from the group consisting of about 8.7±0.2 (2Θ), about 12.5±0.2 (2Θ), and about 20.9±0.2 (2Θ) and may optionally further comprise at least one X-ray peak selected from the group consisting of 11.3±0.2 (2Θ), about 16.7±0.2 (2Θ), about 18.4±0.2 (2Θ), about 25.2±0.2 (2Θ), about 25.9±0.2 (2Θ) and about 26.3±0.2 (2Θ).

To discriminate between crystalline form F and crystalline form A of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine it might be more advantageous to alternatively or additionally look at unique peaks in the X-ray diffraction diagram of F compared to the X-ray diffraction diagram of A. Such characteristic X-ray peaks are those of about 11.3±0.2 (2Θ), about 20.9±0.2 (2Θ), and about 25.2±0.2 (2Θ).

Consequently, in some preferred embodiments of the invention crystalline form F comprises at least one X-ray peak selected from the group consisting of about 11.3±0.2 (2Θ), about 20.9±0.2 (2Θ), and about 25.2±0.2 (2Θ), and may optionally comprise one or more X-ray peaks selected from the group consisting of 8.7±0.2 (2Θ), about 12.5±0.2 (2Θ), about 16.7±0.2 (2Θ), about 18.4±0.2 (2Θ), about 25.9±0.2 (2Θ) and about 26.3±0.2 (2Θ).

A further aspect of the present invention relates to a crystalline form G.

Preferably, the crystalline form G according to the invention has one or more X-ray powder diffraction peaks selected from the group consisting of about 6.6±0.2 (2Θ), about 8.0±0.2 (2Θ) about 18.0±0.2 (2Θ), and about 18.9±0.2 (2Θ).

In some preferred embodiments, the crystalline form G has an X-ray powder diffraction peak of about 6.6±0.2 (2Θ). In some preferred embodiments the crystalline form comprises X-ray powder diffraction peaks of about 6.6±0.2 (2Θ), about 18.0±0.2 (2Θ) and/or about 18.4±0.2 (2Θ).

In some preferred embodiments, crystalline form G comprises X-ray powder diffraction peaks of about 6.6±0.2 (2Θ), about 18.0±0.2 (2Θ) and about 18.4±0.2 (2Θ). In further preferred embodiments, crystalline form G may further comprise X-ray powder diffraction peaks of about 8.0±0.2 (2Θ), about 13.9±0.2 (2Θ), about 18.8±0.2 (2Θ) and about 19.3±0.2 (2Θ).

In some preferred embodiments, crystalline form G comprises X-ray powder diffraction peaks of about 6.6±0.2 (2Θ), about 8.0±0.2 (2Θ), about 18.0±0.2 (2Θ), and about 18.4±0.2 (2Θ). Optionally, X-ray powder diffraction peaks of about 13.3±0.2 (2Θ), 13.9±0.2 (2Θ), about 18.8±0.2 (2Θ), and about 19.3±0.2 (2Θ).

In further preferred embodiments crystalline form G comprises the X-ray powder diffraction peaks (CuKα radiation) of 6.6±0.2 (2Θ), 8.0±0.2 (2Θ), 18.0±0.2 (2Θ), and 18.9±0.2 (2Θ) and may optionally comprise one or more additional peaks selected from the group consisting of about 13.3±0.2 (2Θ), 13.9±0.2 (2Θ), about 18.4±0.2 (2Θ), about 18.8±0.2 (2Θ), and about 19.3±0.2 (2Θ)

In further preferred embodiments, crystalline form G comprises X-ray powder diffraction peaks of about 6.6±0.2 (2Θ), about 8.0±0.2 (2Θ), about 18.0±0.2 (2Θ), about 18.4±0.2 (2Θ), and about 18.9±0.2 (2Θ). Optionally, an additional X-ray powder diffraction peak of about 19.3±0.2 (2Θ) may be comprised. Also optionally, one or more additional X-ray powder diffraction peaks selected from the group consisting of about 7.0±0.2 (2Θ), about 10.4±0.2 (2Θ), about 11.8±0.2 (2Θ), about 12.4±0.2 (2Θ), about 13.3±0.2 (2Θ), about 13.9±0.2 (2Θ), about 15.5±0.2 (2Θ), about 15.6±0.2 (2Θ), about 17.6±0.2 (2Θ), and about 19.7±0.2 (2Θ).

To discriminate between crystalline form G and crystalline form A of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine it might be more advantageous to alternatively or additionally look at unique peaks in the X-ray diffraction diagram of G compared to the X-ray diffraction diagram of A. Such characteristic X-ray peaks are those of about 6.6±0.2 (2Θ), about 7.0±0.2 (2Θ), about 8.0±0.2 (2Θ), about 13.3±0.2 (2Θ), about 13.9±0.2 (2Θ), and about 19.3±0.2 (2Θ). Consequently, in some preferred embodiments of the invention crystalline form G comprises at least one X-ray peak selected from the group consisting of about 6.6±0.2 (2Θ), about 8.0±0.2 (2Θ), and about 19.3±0.2 (2Θ), and optionally at least one additional X-ray peak selected from the group consisting of about 7.0±0.2 (2Θ), about 13.3±0.2 (2Θ), and about 13.9±0.2 (2Θ).

In DSC analyses, crystalline form G according to the present invention preferably exhibits an endothermal event with a peak temperature of about 65-150° C., preferably of about 70-100° C., and/or an endothermal event with a peak temperature of about 230 to 255, preferably of about 237-250° C., more preferably of about 240-248° C. In some preferred embodiments crystalline form E exhibits an endothermal event with a peak temperature of about 242-248° C. Additionally, crystalline form E preferably exhibits an exothermal event with a peak temperature of about 200-220° C., preferably about 204-220° C.

A further aspect of the present invention relates to a crystalline form H

Preferably, the crystalline form H according to the invention has one or more X-ray powder diffraction peaks selected from the group consisting of about 7.1±0.2 (2Θ), about 8.0±0.2 (2Θ), about 18.2±0.2 (2Θ), and about 28.3±0.2 (2Θ).

In some preferred embodiments, the crystalline form H has an X-ray powder diffraction peak of about 18.2±0.2 (2Θ). In some preferred embodiments the crystalline form comprises X-ray powder diffraction peaks of about 8.0±0.2 (2Θ), about 18.2±0.2 (2Θ) and/or about 19.7±0.2 (2Θ).

In some preferred embodiments, crystalline form H comprises X-ray powder diffraction peaks of about 8.0±0.2 (2Θ), about 18.2±0.2 (2Θ), and about 19.7±0.2 (2Θ), and optionally, a further peak of about 18.1±0.2 (2Θ). In some preferred embodiments, crystalline form H may optionally further comprise X-ray powder diffraction peaks of about 17.7±0.2 (2Θ), about 18.8±0.2 (2Θ), and about 19.2±0.2 (2Θ).

In some preferred embodiments, crystalline form H comprises X-ray powder diffraction peaks of about 8.0±0.2 (2Θ), about 18.1±0.2 (2Θ), about 18.2±0.2 (2Θ), and about 19.7±0.2 (2Θ). Optionally, further X-ray peaks of about 17.7±0.2 (2Θ), about 18.8±0.2 (2Θ), about 19.2±0.2 (2Θ), and about 20.7±0.2 (2Θ) may be comprised.

In further preferred embodiments the crystalline form H according to the invention comprises the X-ray powder diffraction peaks of about 7.1±0.2 (2Θ), about 8.0±0.2 (2Θ), about 18.2±0.2 (2Θ), and about 28.3±0.2 (2Θ), and may optionally comprise one or more additional peaks selected from the group consisting of 17.7±0.2 (2Θ), about 18.1±0.2 (2Θ), about 18.3±0.2 (2Θ), about 18.8±0.2 (2Θ), about 19.2±0.2 (2Θ), about 19.7±0.2 (2Θ), and about 20.7±0.2 (2Θ).

In further preferred embodiments, crystalline form H comprises X-ray powder diffraction peaks of about 8.0±0.2 (2Θ), about 18.1±0.2 (2Θ), about 18.2±0.2 (2Θ), about 19.2±0.2 (2Θ), and about 19.7±0.2 (2Θ). Optionally, an additional X-ray powder diffraction peak of about 17.7±0.2 (2Θ) may be comprised. Also optionally, additional X-ray powder diffraction peaks of about 7.1±0.2 (2Θ), about 17.3±0.2 (2Θ), about 17.7±0.2 (2Θ), about 18.8±0.2 (2Θ), and about 20.7±0.2 (2Θ), may be comprised, either in addition to the peak of 17.7±02 (2Θ) or alternatively. Optionally, in some preferred embodiments, crystalline form H comprises at least one additional X-ray powder diffraction peak selected from about 10.4±02 (2Θ), about 17.5±02 (2Θ), about 20.9±02 (2Θ), about 22.3±02 (2Θ), and about 28.3±02 (2Θ). In further preferred embodiments, crystalline form H comprises all of the aforementioned optional additional X-ray peaks.

In order to discriminate between crystalline form H and crystalline form A it might be more advantageous to alternatively or additionally look at unique peaks in the X-ray diffractogram of crystalline form H where form A shows no lines with significant intensity. Such characteristic X-ray peaks are those of about 19.2±0.2 (2Θ), about 7.1±0.2 (2Θ), about 20.9±02 (2Θ), and about 28.3±02 (2Θ). Consequently, in some preferred embodiments of the invention crystalline form H comprises an X-ray peak of about 19.2±0.2 (2Θ), and at least one X-ray peak selected from the group consisting of about 7.1±0.2 (2Θ), about 20.9±02 (2Θ), and about 28.3±02 (2Θ).

In DSC analyses, crystalline form H according to the present invention preferably exhibits an endothermal event with a peak temperature of about 140-160° C., preferably of about 145-160° C., more preferably of about 153-156° C., and/or an endothermal event with a peak temperature of about 230 to 255, preferably of about 237-250° C., more preferably of about 240-248° C. In some preferred embodiments crystalline form H exhibits an endothermal event with a peak temperature of about 242-248° C. Additionally, crystalline form H preferably exhibits an exothermal event with a peak temperature of about 150-190° C., preferably about 163-175° C.

A further aspect of the present invention relates to a crystalline form I

Preferably, the crystalline form I according to the invention has one or more X-ray powder diffraction peaks selected from the group consisting of about 7.1±0.2 (2Θ), about 11.8±0.2 (2Θ), about 14.3±0.2 (2Θ), and about 17.5±0.2 (2Θ).

In some preferred embodiments, crystalline form I has an X-ray powder diffraction peak of about 17.5±0.2 (2Θ). In some preferred embodiments crystalline form I comprises X-ray powder diffraction peaks of about 7.1±0.2 (2Θ) and about 17.5±0.2 (2Θ).

In some preferred embodiments, crystalline form I comprises X-ray powder diffraction peaks of about 7.1±0.2 (2Θ), about 11.8±0.2 (2Θ) and about 17.5±0.2 (2Θ), and optionally, a further peak at about 12.7±0.2 (2Θ). In further preferred embodiments, crystalline form I may further comprise X-ray powder diffraction peaks of about 14.2±0.2 (2Θ), about 14.6±0.2 (2Θ), and about 15.7±0.2 (2Θ).

In some preferred embodiments, crystalline form I comprises X-ray powder diffraction peaks of about 7.1±0.2 (2Θ), about 11.8±0.2 (2Θ), about 12.7±0.2 (2Θ), and about 17.5±0.2 (2Θ). Optionally, X-ray powder diffraction peaks of about 14.2±0.2 (2Θ), about 14.6±0.2 (2Θ), about 15.7±0.2 (2Θ), and 19.6±0.2 (2Θ) are additionally comprised.

In further preferred embodiments, crystalline form I comprises X-ray powder diffraction peaks of about 7.1±0.2 (2Θ), about 11.8±0.2 (2Θ), about 14.3±0.2 (2Θ), and about 17.5±0.2 (2Θ) and may optionally comprise additional peaks selected from the group consisting of about 12.7±0.2 (2Θ), about 14.2±0.2 (2Θ), about 14.6±0.2 (2Θ), about 15.7±0.2 (2Θ), and 19.6±0.2 (2Θ).

In further preferred embodiments, crystalline form I comprises X-ray powder diffraction peaks of about 7.1±0.2 (2Θ), about 11.8±0.2 (2Θ), about 12.7±0.2 (2Θ), about 14.2±0.2 (2Θ), and about 17.5±0.2 (2Θ).

Optionally, an additional X-ray powder diffraction peak of about 14.6±0.2 (2Θ) may be comprised. Also optionally, additional X-ray powder diffraction peaks of about 9.7.±0.2 (2Θ), about 15.1±0.2 (2Θ), and about 15.7±0.2 (2Θ), and/or about 19.6±0.2 (2Θ) may be comprised. Optionally, in some preferred embodiments, crystalline form I comprises at least one additional X-ray powder diffraction peak selected from of about 11.0±0.2 (2Θ), about 16.4±0.2 (2Θ), about 17.9±0.2 (2Θ), about 18.9±0.2 (2Θ), about 21.2±0.2 (2Θ), about 21.6±0.2 (2Θ), about 22.9±0.2 (2Θ), and about 26.3±0.2 (2Θ). In some preferred embodiments, crystalline form I comprises all of the aforementioned optional additional X-ray peaks.

To discriminate between crystalline form I and crystalline form A the X-ray peaks of about 7.1±0.2 (2Θ), about 11.0±0.2 (2Θ), about 14.2±0.2 (2Θ), about 14.6±0.2 (2Θ), about 18.9±0.2 (2Θ), and about 21.2±0.2 (2Θ) might be more advantageously used.

Consequently, in a preferred embodiment of the invention, form I comprises at least one X-ray peak selected from the group consisting of 7.1±0.2 (2Θ), and about 14.2±0.2 (2Θ), and at least one X-ray peak selected from the group consisting of about 11.0±0.2 (2Θ), about 14.6±0.2 (2Θ), about 18.9±0.2 (2Θ), and about 21.2±0.2 (2Θ) 18.7±0.2 (2Θ).

A further aspect of the present invention relates to a crystalline form J

Preferably, the crystalline form J according to the invention has one or more X-ray powder diffraction peaks selected from the group consisting of about 7.1±0.2 (2Θ), about 11.1±0.2 (2Θ), about 14.5±0.2 (2Θ), and about 19.7±0.2 (2Θ).

In some preferred embodiments, the crystalline form has an X-ray powder diffraction peak of about 7.1±0.2 (2Θ). In some preferred embodiments the crystalline form comprises X-ray powder diffraction peaks of about 7.1±0.2 (2Θ), about 11.1±0.2 (2Θ) and/or about 14.5±0.2 (2Θ).

In some preferred embodiments, crystalline form A comprises X-ray powder diffraction peaks of about 7.1±0.2 (2Θ), about 11.1±0.2 (2Θ) and about 19.7±0.2 (2Θ), and optionally, a further peak at about 14.5±0.2 (2Θ). In further preferred embodiments, crystalline form A may further comprise X-ray powder diffraction peaks of about 16.8±0.2 (2Θ), about 17.0±0.2 (2Θ), and about 20.4±0.2 (2Θ).

In some preferred embodiments, crystalline form J comprises X-ray powder diffraction peaks of about 7.1±0.2 (2Θ), about 11.1±0.2 (2Θ), about 14.5±0.2 (2Θ), and about 19.7±0.2 (2Θ). Optionally, X-ray powder diffraction peaks of about 16.8±0.2 (2Θ), about 17.0±0.2 (2Θ), about 20.4±0.2 (2Θ), and 23.1±0.2 (2Θ) are additionally comprised.

In further preferred embodiments, crystalline form J comprises X-ray powder diffraction peaks of about 7.1±0.2 (2Θ), about 11.1±0.2 (2Θ), about 14.5±0.2 (2Θ), about 17.0±0.2 (2Θ), and about 19.7±0.2 (2Θ). Optionally, an additional X-ray powder diffraction peak of about 20.4±0.2 (2Θ) may be comprised. Also optionally, additional X-ray powder diffraction peaks of about 15.0±0.2 (2Θ), about 16.6±0.2 (2Θ), about 16.8±0.2 (2Θ), and about 23.1±0.2 (2Θ) may be comprised, either in addition to the peak of about 20.4±02 (2Θ) or alternatively. Optionally, in some preferred embodiments, crystalline form G comprises at least one additional X-ray powder diffraction peak selected from of about 9.1±0.2 (2Θ) and about 15.3±0.2 (2Θ). In further preferred embodiments, crystalline form J comprises all of the aforementioned optional additional X-ray peaks.

To discriminate between crystalline form J and crystalline form A the X-ray peaks of about 7.1±0.2 (2Θ), about 9.1±0.2 (2Θ), about 11.1±0.2 (2Θ), about 14.5±0.2 (2Θ), about 21.3±0.2 (2Θ), about 23.1±0.2 (2Θ), about 25.3±0.2 (2Θ), about 28.2±0.2 (2Θ), and about 28.8±0.2 (2Θ) might be more advantageously used. Consequently, in a preferred embodiment of the invention, form B comprises at least one X-ray peak selected from the group consisting of 7.1±0.2 (2Θ), about 11.1±0.2 (2Θ), and about 14.5±0.2 (2Θ), and at least one X-ray peak selected from at about 18.7±0.2 (2Θ) in combination with one or more X-ray peaks from the group consisting of about 9.1±0.2 (2Θ), about 21.3±0.2 (2Θ), about 23.1±0.2 (2Θ), about 25.3±0.2 (2Θ), about 28.2±0.2 (2Θ), and about 28.8±0.2 (2Θ).

In DSC analyses, crystalline form J according to the present invention preferably exhibits an endothermal event with a peak temperature of about 230 to 255, preferably of about 237-250° C., more preferably of about 240-248° C. In some preferred embodiments crystalline form J exhibits an endothermal event with a peak temperature of about 242-248° C. Additionally, crystalline form J preferably exhibits an exothermal event with a peak temperature of about 180-190° C., preferably about 183-187° C.

A further aspect of the present invention relates to a crystalline form K

Preferably, the crystalline form K according to the invention has one or more X-ray powder diffraction peaks selected from the group consisting of about 7.1±0.2 (2Θ), about 10.0±0.2 (2Θ), about 14.3±0.2 (2Θ), and about 19.5±0.2 (2Θ).

In some preferred embodiments, crystalline form K has an X-ray powder diffraction peak of about 7.1±0.2 (2Θ). In some preferred embodiments the crystalline form comprises X-ray powder diffraction peaks of about 7.1±0.2 (2Θ), about 14.3±0.2 (2Θ) and/or about 19.5±0.2 (2Θ).

In some preferred embodiments, crystalline form K comprises X-ray powder diffraction peaks of about 7.1±0.2 (2Θ), about 14.3±0.2 (2Θ) and about 19.5±0.2 (2Θ), and optionally, a further peak at about 10.0±0.2 (2Θ). In further preferred embodiments, crystalline form K may further comprise X-ray powder diffraction peaks of about 15.1±0.2 (2Θ), about 15.4±0.2 (2Θ), and about 19.9±0.2 (2Θ).

In some preferred embodiments, crystalline form K comprises X-ray powder diffraction peaks of about 7.1±0.2 (2Θ), about 10.0±0.2 (2Θ), about 14.3±0.2 (2Θ), and about 19.5±0.2 (2Θ). Optionally, X-ray powder diffraction peaks of about 11.2±0.2 (2Θ), 15.1±0.2 (2Θ), about 15.4±0.2 (2Θ), and about 19.9±0.2 (2Θ), are additionally comprised.

In further preferred embodiments, crystalline form K comprises X-ray powder diffraction peaks of about 7.1±0.2 (2Θ), about 10.0±0.2 (2Θ), about 14.3±0.2 (2Θ), about 15.4±0.2 (2Θ), and about 19.4±0.2 (2Θ). Optionally, an additional X-ray powder diffraction peak of about 15.1±0.2 (2Θ) may be comprised. Also optionally, additional X-ray powder diffraction peaks of about 11.2±0.2 (2Θ), about 15.1±0.2 (2Θ), and about 19.9±0.2 (2Θ), either in addition to the peak of about 15.1±02 (2Θ) or alternatively. Optionally, in some preferred embodiments, crystalline form K comprises at least one additional X-ray powder diffraction peak selected from of about 21.4±0.2 (2Θ) and about 27.7±0.2 (2Θ). In some preferred embodiments, crystalline form K comprises all of the aforementioned optional additional X-ray peaks.

To discriminate between crystalline form K and crystalline form A the X-ray peaks of about 7.1±0.2 (2Θ), about 11.2±0.2 (2Θ), about 14.3±0.2 (2Θ), about 21.4±0.2 (2Θ), about 26.7±0.2 (2Θ), and about 27.7 might be more advantageously used. Consequently, in a preferred embodiment of the invention, crystalline form K comprises at least one X-ray peak selected from the group consisting of about 7.1±0.2 (2Θ), about 11.2±0.2 (2Θ), and about 14.3±0.2 (2Θ), and at least one X-ray peak selected from about 21.4±0.2 (2Θ), about 26.7±0.2 (2Θ), and about 27.7 4±0.2 (2Θ).

In DSC analyses, crystalline form K according to the present invention preferably exhibits an endothermal event with a peak temperature of about 90-145° C., preferably of about 120-140° C., more preferably of about 130-140° C., and/or an endothermal event with a peak temperature of about 230 to 255, preferably of about 237-250° C., more preferably of about 240-248° C. In some preferred embodiments crystalline form K exhibits an endothermal event with a peak temperature of about 242-248° C. Additionally, crystalline form K preferably exhibits an exothermal event with a peak temperature of about 180-190° C.

A further aspect of the present invention relates to a crystalline form L.

Preferably, the crystalline form L according to the invention has one or more X-ray powder diffraction peaks selected from the group consisting of about 8.1±0.2 (2Θ), about 12.0±0.2 (2Θ), about 17.1±0.2 (2Θ), and about 20.1±0.2 (2Θ).

In some preferred embodiments, crystalline form L has an X-ray powder diffraction peak of about 8.1±0.2 (2Θ). In some preferred embodiments the crystalline form comprises X-ray powder diffraction peaks of about 8.1±0.2 (2Θ), about 17.1±0.2 (2Θ) and/or about 20.1±0.2 (2Θ).

In some preferred embodiments, crystalline form L comprises X-ray powder diffraction peaks of about 8.1±0.2 (2Θ), about 17.1±0.2 (2Θ) and about 20.1±0.2 (2Θ), and optionally, a further peak at about 12.0±0.2 (2Θ). In further preferred embodiments, crystalline form K may further comprise X-ray powder diffraction peaks of about 24.3±0.2 (2Θ), about 21.2±0.2 (2Θ), and about 21.9±0.2 (2Θ).

In some preferred embodiments, crystalline form L comprises X-ray powder diffraction peaks of about 8.1±0.2 (2Θ), about 12.0±0.2 (2Θ), about 17.1±0.2 (2Θ), and about 20.1±0.2 (2Θ). Optionally, X-ray powder diffraction peaks of about 16.4±0.2 (2Θ), 21.2±0.2 (2Θ), 21.9±0.2 (2Θ), about and 24.3±0.2 (2Θ), are additionally comprised.

In further preferred embodiments, crystalline form L comprises X-ray powder diffraction peaks of about 8.1±0.2 (2Θ), about 12.0±0.2 (2Θ), about 17.1±0.2 (2Θ), about 20.1±0.2 (2Θ), and about 24.3±0.2 (2Θ). Optionally, an additional X-ray powder diffraction peak of about 21.2±0.2 (2Θ) may be comprised. Also optionally, additional X-ray powder diffraction peaks of about 7.7±0.2 (2Θ), about 16.4±0.2 (2Θ), and about 21.9±0.2 (2Θ), either in addition to the peak of about 21.2±02 (2Θ) or alternatively. Optionally, in some preferred embodiments, crystalline form L comprises one additional X-ray powder diffraction peak of 18.0±0.2 (2Θ). In preferred embodiments, crystalline form L comprises all of the aforementioned optional additional X-ray peaks.

To discriminate between crystalline form L and crystalline form A the X-ray peaks of about 8.1±0.2 (2Θ), about 21.2±0.2 (2Θ), and about 24.3±0.2 (2Θ), might be more advantageously used. Consequently, in a preferred embodiment of the invention, crystalline form K comprises an X-ray peak of about 8.1±0.2 (2Θ), about 21.2±0.2 (2Θ) and/or about 24.3±0.2 (2Θ).

In DSC analyses, crystalline form L according to the present invention preferably exhibits an endothermal event with a peak temperature of about 135 to 150° C., preferably of about 140-150° C., and/or an endothermal event with a peak temperature of about 230 to 255, preferably of about 237-250° C., more preferably of about 240-248° C. In some preferred embodiments crystalline form L exhibits an endothermal event with a peak temperature of about 242-248° C. Additionally, crystalline form L preferably exhibits an exothermal event with a peak temperature of about 170-210° C., preferably about 190-210° C.

A further aspect of the present invention relates to a crystalline form Q.

Preferably, the crystalline form Q according to the invention has one or more X-ray powder diffraction peaks selected from the group consisting of about 8.2±0.2 (2Θ), about 8.6±0.2 (2Θ), about 17.2±0.2 (2Θ), and about 24.4±0.2 (2Θ).

In some preferred embodiments, crystalline form Q has an X-ray powder diffraction peak of about 8.2±0.2 (2Θ). In some preferred embodiments the crystalline form comprises X-ray powder diffraction peaks of about 8.2±0.2 (2Θ), about 17.2±0.2 (2Θ) and/or about 24.4±0.2 (2Θ).

In some preferred embodiments, crystalline form Q comprises X-ray powder diffraction peaks of about 8.2±0.2 (2Θ), about 17.2±0.2 (2Θ) and about 24.4±0.2 (2Θ), and optionally, a further peak at about 8.6±0.2 (2Θ). In further preferred embodiments, crystalline form Q may further comprise X-ray powder diffraction peaks of about 11.0±0.2 (2Θ), about 12.0±0.2 (2Θ), and about 16.5±0.2 (2Θ).

In some preferred embodiments, crystalline form Q comprises X-ray powder diffraction peaks of about 8.2±0.2 (2Θ), about 17.2±0.2 (2Θ), about 24.4±0.2 (2Θ), and about 8.6±0.2 (2Θ). Optionally, X-ray powder diffraction peaks of about 11.0±0.2 (2Θ), about 12.0±0.2 (2Θ), about 16.5±0.2 (2Θ) and about 20.1±0.2 (2Θ), are additionally comprised.

In further preferred embodiments, crystalline form Q comprises X-ray powder diffraction peaks of about 8.2±0.2 (2Θ), about 8.6±0.2 (2Θ), about 17.2±0.2 (2Θ), about 24.4±0.2 (2Θ), and about 16.5±0.2 (2Θ). Optionally, an additional X-ray powder diffraction peak of about 11.0±0.2 (2Θ) may be comprised. Also optionally, X-ray powder diffraction peaks of about 11.5±0.2 (2Θ), 12.0±0.2 (2Θ), about 16.5±0.2 (2Θ) and about 20.1±0.2 (2Θ) are additionally comprised.

Optionally, in some preferred embodiments, crystalline form Q comprises one additional X-ray powder diffraction peak of 21.3±0.2 (2Θ). In preferred embodiments, crystalline form Q comprises all of the aforementioned optional additional X-ray peaks.

To discriminate between crystalline form Q and crystalline form A the X-ray peaks of about 8.2±0.2 (2Θ), about 11.0±0.2

(2Θ), about 21.3±0.2 (2Θ), and about 24.4±0.2 (2Θ) might be more advantageously used. Consequently, in a preferred embodiment of the invention, crystalline form Q comprises an X-ray peak of about 8.2±0.2 (2Θ), about 11.0±0.2 (2Θ) and/or about 24.4±0.2 (2Θ) and may optionally comprise an X-ray peak of about 21.3±0.2 (2Θ).

In DSC analyses, crystalline form Q according to the present invention preferably exhibits at least one endothermal event with a peak temperature of about 115 to 140° C., preferably of about 130-140° C., and/or an endothermal event with a peak temperature of about 155 to 165 and/or an endothermal event with a peak temperature of about 230 to 255, preferably of about 237-250° C., more preferably of about 240-248° C. In some preferred embodiments crystalline form L exhibits an endothermal event with a peak temperature of about 242-248° C. Additionally, crystalline form Q preferably exhibits an exothermal event with a peak temperature of about 180-210° C., preferably about 185-205° C.

Another aspect of the present invention relates to a process for the production of the crystalline form according to the invention.

In a preferred embodiment, the process comprises the step of
(a-1) suspending cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine in a solvent.

In step (a-1) cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine can be partially or even completely dissolved in the solvent.

Conventional solvents known to persons skilled in the art may be used as solvents in a suspension of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; and also N-methyl-2-pyrrolidone, dimethyl formamide and dimethyl sulfoxide; and mixtures thereof.

In a preferred embodiment, the solvent comprises at least one alcohol selected from the group consisting of methanol, ethanol, n-propanol and iso-propanol.

In another preferred embodiment, the solvent comprises at least one organic solvent selected from the group consisting of n-pentane, n-hexane, tert-butylmethylether, ethylacetate, acetone, acetonitrile, diethylether, dichloromethane, tetrahydrofurane, ethylmethylketone and toluene or mixtures thereof.

In yet another preferred embodiment, the solvent additionally comprises water.

In still another preferred embodiment, the solvent consists of isopropanol or a mixture of isopropanol and water.

Preferably, in the process according to the invention, step (a-1) is carried out at a temperature below or at the boiling point of the respective solvent, preferably at a temperature not higher than 120° C., more preferably not higher than 100° C., even more preferably not higher than 90° C., and in particular in a temperature range of 40° C. to 90° C.

Preferably, in the process according to the invention, the suspension/solution obtained in step (a-1) is stirred for a time period of at least 0.3 h, preferably in the range of 0.3 h to 5 days, preferably 0.3 h to 4 days, more preferably 0.3 h to 2 days, still more preferably 0.3 h to 1 day, even more preferably between 0.3 h to 12 h, especially preferably 0.3 to 2 h.

Preferably, the process according to the invention further comprises the step
(b-1) separating, preferably filtering off the solid obtained in step (a-1).

In preferred embodiments of the process according to the invention separation step (b-1) comprises the addition step of cooling the suspension or solution obtained in step (a-1) prior to the separation of the solid. This is especially preferred if step (a-1) is carried out at elevated temperatures and/or if cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine is completely or partially dissolved in the solvent.

Preferably, the process according to the invention further comprises the step
(c-1) drying of the solid obtained in step (b-1).

Preferably, in the process according to the invention, step (c-1) takes place under air. However, drying under vacuum, more preferably at a vacuum of 0 to 900 mbar, even more preferably at a vacuum of 1 to 500 mbar, and in particular at a vacuum of 10 to 200 mbar is also possible.

Preferably, in the process according to the invention, step (c-1) takes place in a temperature range from 0 to 75° C., preferably from 10° C. to 60° C. more preferably from 20 to 55° C.

By a preferred embodiment of the process according to the present invention crystalline form A can be obtained. This preferred embodiment comprises the steps of
(a-1') suspending cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine for at least 0.3 h in a solvent at a temperature in the range of 20° C. and the boiling point of the solvent, wherein the solvent is selected from the group consisting of isopropanol and a mixture of isopropanol and water, wherein the mixture may comprise up to 75 vol-% water;
(b-1') separating, preferably filtering off the solid obtained in step (a-1'), and
(c-1') drying the solid obtained in step (b-1') at a temperature in the range of 0° to 75° C., preferably at a temperature in the range of 20 to 55° C., more preferably at 50° C.

Preferably, step (b-1") comprises the additional step of cooling the suspension obtained in step (a-1'), preferably to ambient temperature, prior to separating the solid from the solvent. Furthermore, drying step (c-1") is preferably conducted under reduced pressure.

By a more preferred embodiment of the process according to the present invention crystalline form A can be obtained. This embodiment comprises the steps of
(a-1''') suspending cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine for at least 0.3 h in a solvent at a temperature in the range of 20° C. and the boiling point of the solvent, wherein the solvent is selected from the group consisting of isopropanol and a mixture of isopropanol and water, wherein the mixture may comprise up to 75 vol-% water;
(b-1''') separating, preferably filtering off the solid obtained in step (a-1'), and
(c-1''') drying the solid obtained in step (b-1'), preferably at a temperature in the range of 0° to 75° C., more preferably at a temperature in the range of 20 to 55° C., even more preferably at 50° C.

Preferably, step (b-1''') comprises the additional step of cooling the suspension obtained in step (a-1'''), preferably to ambient temperature, prior to separating the solid from the solvent. Furthermore, drying step (c-1''') is preferably conducted under reduced pressure.

A further aspect of the invention relates to crystalline form A obtainable by the process as described above.

In another preferred embodiment of the process according to the present invention crystalline form B can be obtained. This preferred embodiment comprises the step of (a-2) suspending cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine in a solvent at a temperature in the range of 20° C. to 60° C., wherein the solvent is a mixture of water and an alcohol selected from the group consisting of ethanol, n-propanol and isopropanol, wherein the mixture may comprise up to 50 vol.-% water, preferably up to 30% water;

(b-2) separating, preferably filtering off the solid obtained in step (a-2), and (c-2) drying the solid obtained in step (b-2).

Preferably, on or more of crystalline forms A, D or Q of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine is suspended in step (a-2)

In a preferred embodiment of this process, the crystalline form is step (a-2) is suspended in the solvent for at least 2 h, preferably, at least 6 h, more preferably 12 h. In further preferred embodiments crystalline form B is suspended in the solvent for between 2 h and 14 d, preferably between 12 h and 7 d, more preferably between 1 d and 5 d.

In preferred embodiments of this process, the solvent is a mixture of ethanol and water, wherein the mixture may contain between 99.9 and 50 vol.-% of ethanol. Preferably, the mixture comprises 60 to 75 vol.-% ethanol. In additional preferred embodiments the solvent is a mixture of n-propanol and water or of isopropanol and water. Preferably, in these mixtures the n-propanol or isopropanol is present in 60 to 99 vol.-%, preferably in 75 to 97 vol.-%.

In further preferred embodiments, the solid obtained from step (b-2) is dried in step (c-2) at a temperature in the range of 20° C. and 60° C., preferably 30° to 55° C., more preferably at 50° C. Optionally, the solid obtained in step (b-2) is dried in step (c-2) at reduced pressure.

A further aspect of the invention relates to crystalline form B obtainable by the process as described above.

In another preferred embodiment of the process according to the present invention crystalline form C can be obtained. This preferred embodiment comprises the step of (a-3) suspending cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine in a solvent at a temperature in the range of 20° C. and the boiling point of the solvent, wherein the solvent is methanol or a mixture of water and methanol, wherein the mixture may comprise up to 50 vol.-% water, preferably up to 25 vol.-% water;

(b-3) separating, preferably filtering off the solid obtained in step (a-3), and (c-3) drying the solid obtained in step (b-3).

Preferably, one or more of crystalline forms A, D, and E of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine are suspended in step (a-2).

In a preferred embodiment of this process, the crystalline form in step a-3 is suspended in the solvent for a time between at least 2 h and up to 14 d, preferably for at least 2 h to 24 h. The lower the temperature applied to the suspension in step (a-3) the longer the stirring time should be.

In further preferred embodiments, the solid obtained from step (b-3) is dried in step (c-3) at a temperature in the range of 20° C. and 40° C., preferably 20° to 30° C., more preferably at 20° C. Preferably, the solid obtained in step (b-3) is in step (c-3) dried at ambient pressure.

A further aspect of the invention relates to crystalline form C obtainable by the process as described above.

In another preferred embodiment of the process according to the present invention crystalline form D can be obtained. This preferred embodiment comprises the step of In another preferred embodiment of the process according to the present invention crystalline form D can be obtained. This preferred embodiment comprises the step of (a-4) suspending cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine for at least 0.3 h in a solvent at a temperature in the range of 20° C. and the boiling point of the solvent, wherein the solvent is selected from the group consisting of acetonitrile, acetone and water, or mixtures of acetonitrile or acetone with water;

(b-4) separating, preferably filtering off the solid obtained in step (a-4), and (c-4) drying the solid obtained in step (b-3).

Preferably, crystalline forms A, E, or G are suspended in step (a-4).

Preferably, the solvent is acetone and the temperature at which the crystalline form is suspended is the boiling point of acetone. Preferable, the suspension is maintained at this temperature of 0.3 to 1 h, preferably 0.5 h.

In a preferred embodiment, step (b-4) comprises the step of cooling the suspension to ambient temperature prior to separation the solvent from the solid obtained in step (a-4).

A further aspect of the invention relates to crystalline form D obtainable by the process as described above.

Another aspect of the invention relates to a process for the production of crystalline form E of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine.

This process comprises the step:

(a-4) suspending cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine fumarate in water;

(b-4) adding an excess of an organic base to the suspension and stirring the reaction mixture of at least 2 h; and (c-4) separating, preferably filtering off the solid obtained in step (b-4), and (d-4) drying the solid obtained in step (c-4).

In a preferred embodiment the organic base in step (b-4) is a dialkyl- or trialkylamine, preferably triethylamine.

In a further preferred embodiment, step (c-4) comprises as additional step (c-4.1) at least once slurrying the isolated solid in water and separating, preferably filtering off the solid obtained in step (c-4.1).

In a preferred embodiment the solid obtained in step (c-4/c-4.1) is dried at 40° C. to 75° C., preferably at 70° C. and preferably at reduced pressure.

A further aspect of the invention relates to crystalline form E obtainable by the process as described above.

In a preferred embodiment the crystalline form according to the invention is subsequently transformed into an amorphous form.

Suitable methods for the preparation of amorphous forms are known to a person skilled in the art. For example, amorphous forms or amorphous mixtures may be obtained by means of the following methods or combinations thereof:
i) precipitation from solution,
ii) lyophilization,
iii) spray drying,
iv) melts extrusion,
v) flash evaporation,
vi) quench cooling of the melt,
vii) grinding at ambient or liquid nitrogen temperatures,
viii) working under protection of an inert atmosphere (e.g. gaseous nitrogen or argon), and/or
ix) using capillary crystallization technology.

Another aspect of the invention relates to an amorphous form of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine, preferably to an amorphous form that is obtainable by any of the above methods or combinations thereof.

Mixtures of the crystalline forms A, B, C, D, E, F, G, H, I, J, K, L and Q, preferably mixtures of two of these crystalline forms, are also included within the scope of the present invention.

For example, such mixtures of two crystalline forms may be obtained from one or more of the crystalline forms A, B, C, D, E, F, G, H, I, J, K, L and Q during a crystallization process (e.g. cooling or evaporation) or respectively during a separation process (e.g. filtration), or respectively during a process where heat is applied (e.g. drying), or respectively during a process where mechanical energy is inserted (e.g. milling or grinding).

Furthermore, such mixtures of two crystalline forms may be obtained from one or more of crystalline forms A, B, C, D, E, F, G, H, I, J, K, L or Q by a partial uptake of hydrate water or respectively by a partial loss of hydrate water, or respectively by a solvent/water exchange.

Another aspect of the invention relates to a composition comprising a mixture of at least two crystalline forms as described herein; or a mixture of at least one crystalline form as described herein with an amorphous form; or a mixture of at least one crystalline form as described herein with a salt of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine with fumaric acid; in any mixing ratio.

Preferably, the degree of crystallinity, i.e. the content of crystalline form(s) of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine relative to the total content of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine (crystalline form(s)+amorphous form(s)) is at least 40 wt.-%, more preferably at least 60 wt.-%, still more preferably at least 80 wt.-%, yet more preferably at least 90 wt.-%, even more preferably at least 95 wt.-%, most preferably at least 99 wt.-%, and in particular at least 99.5 wt.-%.

Yet a further aspect the invention relates to a pharmaceutical composition comprising at least one crystalline form according to the invention.

In another aspect the present invention relates to methods of treating pain, comprising administering a pharmaceutical composition that comprises a crystalline form as described herein to a patient in need thereof (for example, a patient who has been diagnosed with a pain disorder).

The term pain as used herein preferably includes but is not limited to pain selected from the group consisting of neuropathic pain, diabetic neuropathic pain, chronic neuropathic pain.

In another aspect the present invention relates to a pharmaceutical composition comprising a crystalline form as described herein and optionally one or more suitable additives and/or adjuvants such as described below.

Preferably said pharmaceutical composition may be used for the treatment of pain.

In still another aspect the present invention relates to a medicament comprising a crystalline form as described herein, preferably a pharmaceutical composition as described herein. In a preferred embodiment, the medicament is a solid drug form. The medicament is preferably manufactured for oral administration. However, other forms of administration are also possible, e.g. for buccal, sublingual, transmucosal, rectal, intralumbal, intraperitoneal, transdermal, intravenous, intramuscular, intragluteal, intracutaneous and subcutaneous application.

Depending on the configuration, the medicament (dosage form) preferably contains suitable additives and/or adjuvants. Suitable additives and/or adjuvants in the sense of the invention are all substances known to a person skilled in the art for the formation of galenic formulations. The choice of these adjuvants and also the quantities to be used are dependent on how the medication is to be administered, i.e. orally, intravenously, intraperitoneally, intradermally, intramuscularly, intranasally, buccally or locally.

Furthermore, the present invention relates to a method for treating pain in a patient, preferably in a mammal, which comprises administering an effective amount of a crystalline form as described herein to a patient.

EXAMPLES

The following examples serve to explain the invention in more detail, but should not be interpreted as restrictive.

The following abbreviations are used in the examples:
d day
DMSO dimethylsulfoxid
EtOAc ethyl acetate
EtOH ethanol
Ex example
FT-Raman Fourier transformation Raman spectroscopy
H hour
IPE diisopropyl ether
MeCN acetonitril
MEK 2-butanone
MeOH methanol
min minute
NMP N-methyl-2-pyrrolidone
1PrOH n-propanol (1-propanol)
2PrOH iso-propanol (2-propanol)
PXRD powder x-ray diffraction
r.h. relative humidity
RT room temperature, preferably 20-25° C.
SCXRD single crystal X-ray diffraction
sec seconds t time (duration)
T Temperature
TBME tert-butyl methyl ether
TG-FTIR thermogravimetry coupled with Fourier transform infrared spectroscopy
THF tetrahydrofuran
XRPD X-ray powder diffraction In the following "compound (1)" denotes cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine.

Unless otherwise specified, solvent mixtures are always volume/volume.

The synthesis of compound (1) is described in WO2012/013343 A1, page 48-49.

A) Crystalline Form A

General Procedure for Syntheses:

A quantity of compound (1) is charged into a vial or flask and an amount of solvent is added. The resulting suspension/solution is stirred (e.g. orbital shaker or overhead-stirrer) for a given time at a specific temperature. Subsequently, if the suspension/solution was stirred at an elevated temperature, it is allowed to cool to room temperature or any other predetermined temperature to precipitate or crystallize the product and the solvent is removed by filtration.

The thus obtained solid is dried, preferably at room temperature.

In table 1 below, specific reaction conditions for syntheses of crystalline form A are listed.

TABLE 1

| Example | Crystalline form of starting material | Amount [mg] | Solvent/ amount | T [° C.] | Reaction time [d] | Comment |
|---|---|---|---|---|---|---|
| A1 | D | 227.7 | 2-propanol/ 5 ml | RT | 5 d | Day 5 without stirring |
| A2 | D | 190 | 2-propanol/ 10 ml | RT | 3 d | — |
| A3 | D | 206.1 | 1-propanol/ 5 ml | RT | 5 d | Day 5 without stirring |
| A4 | E | 101 | 1-pentane/ 2.5 ml | 40 | 0.75 d | — |
| A5 | E | 102 | 1-propanol/ 2.5 ml | 40 | 0.75 d | — |
| A6.1 | E | 110.5 | TBME/2.5 ml | 40 | 0.75 d | — |
| A6.2 | E | 102.8 | n-hexane/ 2.5 ml | 30 | 0.75 d | — |
| A6.3 | E | 102 | n-pentane/ 2.5 ml | 30 | 0.75 d | — |
| A6.4 | E | 107 | 1-propanol/ 2.5 ml | 40 | 0.75 d | — |
| A10.1 | D | 206.1 | 1-propanol/ 5 ml | RT | 4 d | — |
| A10.2 | D | 227.7 | 2-propanol/ 5 ml | RT | 4 d | — |
| A12 | B | 8300 | 2-propanol/ 120 ml Water/280 ml (3:7) | 52 | 5 d | After cooling to RT the suspension was stirred for an additional hour. |

Example A13

Crystalline form H of compound (1) can be transformed into form A by heating a sample of crystalline form H, which was filled into a quartz capillary to a temperature between 150° C. to 250° C. The sample remained crystalline form A upon cooling the sample to 20° C.

Example A 17

Interconversion/Slurry Experiments

About 25 mg of a specific crystalline form of compound (1) and 25 mg of the same or another crystalline form of compound (1) were charged into a vial and 1.0 mL of 2-Propanol was added. The vials were closed and the mixtures were stirred (via shaking using an Eppendorf Thermomixer, starting with 750 rpm, increased to 1000 rpm after 1 day) at an elevated temperature (30±2° C.) for 7 days. Subsequently the mixtures were cooled to 20±2° C. and stirred for an additional 2 hours.

The solids were then separated via filtration using a suction filter. To dry the thus obtained solid material an air flow was applied for 2 to 3 hours.

The crystalline form of the obtained materials was determined using XRPD. The experiments are summarized below in table 2 below.

TABLE 2

| ID | Amount compound (1)/[mg] and crystalline forms in starting material | Resulting crystalline form |
|---|---|---|
| A17.1 | 24.8 mg D 26.2 mg D | A |

TABLE 2-continued

| ID | Amount compound (1)/[mg] and crystalline forms in starting material | Resulting crystalline form |
|---|---|---|
| A17.2 | 21.8 mg E 24.8 mg A | A |

TABLE 2-continued

| ID | Amount compound (1)/[mg] and crystalline forms in starting material | Resulting crystalline form |
|---|---|---|
| A17.3 | 24.0 mg E<br>23.8 mg D | A |
| A17.4 | 22.9 mg E<br>21.4 mg 63* | A |
| A17.5 | 20.7 mg E<br>22.1 mg G | A |
| A17.6 | 23.1 mg E<br>22.6 mg C | H |
| A17.8 | 24.5 mg E<br>24.2 mg 58* | A |
| A17.9 | 22.6 mg E<br>22.2 mg L | A + H |
| A17.10 | 23.0 mg E<br>34.7 mg 64* | A + H |
| A17.11 | 24.0 mg E<br>24.4 mg A + Pks* | A |
| A17.12 | 23.6 mg E<br>23.3 mg P | A |
| A17.13 | 25.9 mg E<br>24.1 mg O | A |
| A17.14 | 24.7 mg D<br>25.6 mg D | A |
| A17.15 | 20.9 mg E<br>23.2 mg A | A |
| A17.16 | 21.8 mg E<br>20.9 mg D | A |
| A17.17 | 20.6 mg E<br>20.7 mg 63* | A |
| A17.18 | 23.3 mg E<br>22.7 mg G | A |
| A17.19 | 23.3 mg E<br>24.2 mg C | H |
| A17.20 | 25.1 mg E<br>25.3 mg 58* | A |
| A17.21 | 22.8 mg E<br>23.4 mg L | A + H |
| A17.22 | 22.6 mg E<br>22.2 mg 64* | A + H |
| A17.23 | 24.1 mg E<br>25.4 mg A + Pks* | A |
| A17.24 | 26.2 mg E<br>26.2 mg P | A |
| A17.25 | 25.2 mg E<br>24.3 mg O | A |

[*denote crystalline material in a polymorphic form not further characterized but most likely other than the ones described herein]

From the above interconversion experiments, it becomes apparent that under these reaction conditions, crystalline form A is predominantly formed, i.e. that crystalline form A is thermodynamically more stable than the other crystalline forms. This advantageous property makes crystalline form A an attractive material for use in pharmaceutical compositions.

Example A15

100 mg of crystalline form A of compound (1) was charged into a vial and 10 mL of a mixture ethylacetate/water 70:30 (vol/vol, i.e. 7 mL ethylacetate, 3 mL water) was added. The vial was closed and the mixture (a white suspension) was stirred (by means of shaking, 400 rpm, PLS Synthesiser) at room temperature (22±2° C.) for 13 days.

The solid was separated using a suction filter and dried by applying an air flow for additional 5 to 30 minutes (until the solid appeared to be dry). The resulting material was identified via x-ray powder diffraction to be crystalline form A of compound (1).

Example A16

0.99 g of crystalline form A of compound (1) was charged into a vial and 25 mL of ethanol p.a. was added. The vial was closed and the suspension was stirred (by means of shaking, PLS shaker, 400 rpm) at an elevated temperature (40° C.±2) for 20 h.

The mixture was cooled to 20±2° C. The solid was separated using a suction filter (G4) and dried by applying an air flow until the sample appeared to be dry. The white solid was subsequently left for 1 h at ambient conditions. Subsequently, it was identified via x-ray powder diffractometry to be crystalline form A of compound (1).

Example A18

Crystalline form A of compound (1) can be obtained by suspending in the flask fitted with a reflux condenser 34.6 g of compound (1) (e.g. as crystalline form C, E, G and/H, or any other form) in a mixture of 260 ml water and 606 ml isopropanol. The suspension is subsequently heated and stirred at 100° C. for 30 minutes which leads to the formation of a very fine suspension of crystalline material which settles very quickly after stirring is stopped.

The reaction slurry is cooled to 20° C. and the solvent mixture is removed by filtration (suction filter). The solid crystalline material is dried over night at 50° C. under reduced pressure Yield: 26 g (75%)

B) Crystalline Form B

General Procedure for Syntheses: See General Procedure for Syntheses of Crystalline Form A.

In table 3 below, specific reaction conditions for syntheses of crystalline form B are listed.

TABLE 3

| Ex. | Crystalline form of starting material | Amount [mg] | Solvent/amount | T [° C.] | Reaction time [d] | Comment |
|---|---|---|---|---|---|---|
| B1 | D | 224.7 | Ethanol/5 ml | RT | 5 | Day 5 without stirring |
| B2 | D | 165.3 | Ethanol 10.5 ml/water 4.5 ml (7:3) | RT | 3 | — |
| B3 | D | 176.4 | Ethanol 10.5 ml/water 4.5 ml (7:3) | 50 | 3 | — |
| B4 | D | 225 | Ethanol/5 ml | RT | 4 | — |
| B6 | D | 488 | Ethanol 21 ml/water 9 ml (7:3) | 50 | 4.83 | For the final 20 h, the suspension is stirred at RT. |
| B7 | A | 101 | Ethanol 7 ml/water 3 ml (7:3) | RT | 13 | |
| B9.1 | Q | 30.7 | 1-Propanol:water (8:2) 1.5 ml | RT | 7 | |
| B9.2 | Q | 30.0 | 2-Propanol:water (8:2) 1.5 ml | RT | 7 | |

Example B8

Stability of Crystalline Form B

Two samples (100 mg each) of crystalline form B of compound (1) were charged into a petri dish and dried at 50±2° C. at reduced pressure (about 7 mBar) for 72 hours. The samples were let to cool to room temperature under ambient conditions before they were analyzed. The analysis revealed that the obtained material was still compound (1) in crystalline form B.

This example and example B7 demonstrate that in the presence of water, crystalline form B may form as a relatively stable polymorph or hydrate although the water content may vary and/or change. The formation of form A (ansolvate) or form B (hydrate) in the presence of water depends on the organic co-solvent used as the reaction medium (preferably ethanol) and the reaction temperature (preferable room temperature).

C) Crystalline Form C

General Procedure for Syntheses: See General Procedure for Syntheses of Crystalline Form A. In table 4 below, specific reaction conditions for syntheses of crystalline form B are listed.

TABLE 4

| Ex. | Crystalline form of starting material | Amount [mg] | Solvent/amount | T [° C.] | Reaction time [d] | Comment |
|---|---|---|---|---|---|---|
| C1 | E | 100 | Methanol/2.5 ml | 40 | 0.75 | |
| C2 | A | 1010 | Methanol/25 ml | 40 | 0.83 | |
| C3 | E | 103 | Methanol/2.5 ml | 40 | 0.75 | |
| C4 | A | 53.7 | Methanol/2 ml | 30 | 19 | |
| C5.1 | A | 100 | Methanol/5 ml | 50 | 1 | |
| C5.2 | A | 100 | Methanol/3.5; Water/1.5 ml | 50 | 1 | |
| C6 | A | 100 | Methanol/7 ml; Water/3 ml | RT | 13 | |
| C7 | D | 650 | Methanol/150 ml | 56 | 5 | |
| C8 | D | 280 | Methanol/150 ml | 80 | 0.125 (3 h) | Reflux |
| C9 | D | 778 | Methanol/250 ml | 80 | 0.17 (4 h) | Reflux |
| C10 | E | 150 | Methanol/50 ml | 70 | 0.125 (3 h) | Solid was filtered from hot suspension. |
| C11 | H | 75 | Methanol/75 ml | 50 | 14 | |

D) Crystalline Form D

General Procedure for Syntheses: See General Procedure for Syntheses of Crystalline Form A. In table 5 below, specific reaction conditions for syntheses of crystalline form D are listed.

TABLE 5

| Ex. | Crystalline form of starting material | Amount [mg] | Solvent/amount | T [° C.] | Reaction time [d] | Comment |
|---|---|---|---|---|---|---|
| D6.1 | E | 116.6 | Acetone/2.5 ml | 40 | 0.75 | — |
| D6.2 | E | 113 | Acetonitrile/2.5 ml | 40 | 0.75 | — |
| D6.3 | E | 106.4 | Diethylether/7.5 ml | 40 | 0.75 | — |
| D6.4 | E | 104.5 | Dichloromethane/7.5 ml | 40 | 0.75 | — |
| D6.5 | E | 105.2 | Ethylmethylketone/2.5 ml | 40 | 0.75 | — |
| D8.1 | A | 49.7 | Dichloromethane/2 ml | 30 | 19 | |
| D8.2 | A | 53.6 | Diethylether/2 ml | 30 | 19 | |
| D8.3 | A | 73.7 | Acetone/1 ml | 30 | 19 | |
| D8.4. | A | 95.9 | THF/0.5 ml | 30 | 19 | Solvent was removed by evaporation under ambient conditions instead of filtration. |
| D8.5 | A | 51.5 | Acetonitrile/2 ml | 30 | 19 | |
| D9.1 | A | 100 | Acetone/5 ml | 50 | 1 | |
| D9.2 | A | 100 | Acetone/3.5 ml; Water/1.5 ml | 50 | 1 | |
| D12.1 | G | 55 | Acetone/1.5 ml | RT | 1 | |
| D12.2 | G | 51 | Dichloromethane | RT | 1 | |

Examples D1, D2, D3, D4, D10, D11 and D13

In the above mentioned examples, which were carried out as described in the general procedure for syntheses of polymorph D under reaction conditions listed below in table 6, crystalline form D did not transform into another polymorphic form.

TABLE 6

Stability of crystalline form D

| Ex. | Crystalline form of starting material | Amount [mg] | Solvent/amount | T [° C.] | Reaction time [d] |
|---|---|---|---|---|---|
| D1 | D | 207.6 | Acetonitrile/5 ml | RT | 5 d* |
| D2 | D | 170.7 | Acetone/10.5 ml; Water/4.5 ml | RT | 3 d |
| D3 | D | 188.6 | Acetone/10.5 ml; Water/4.5 ml | 50 | 3 d |
| D4 | D | 196 | Water/10 ml | RT | 3 d |
| D10 | D | 208 | Acetonitrile/5 ml | RT | 4 d |
| D11 | D | 196 | Water/10 ml | RT | 4 d |
| D13 | D | 517 | Acetonitrile/20 ml | 50 | 5 d** |

*Day 5 without stirring.
**Day 5 at RT.

Example D14

238 g of crystalline form E of compound (1) are charged into a suitable reaction vessel under inert conditions ($N_2$-atmosphere) and 17 l of acetone are added. Whilst stirring at 130 rpm the suspension is heated to reflux (55° C.) for 30 min. The suspended solid is thereby completely dissolved. The heating is switched off and the solution is slowly cooled to 18° C. The precipitated solid is filtered off under suction via a glass frit (G3) and dried for 3 h in the air flow. The solid is further dried at 50° C. in a vacuum oven under reduced pressure (p<2 mbar) for 35 h.

The dried product (136.6 g) was analyzed and identified to be crystalline form D or compound (1).

E) Crystalline Form E

Example E1

Crystalline form can be obtained by drying crystalline form G for 2 h at 100° C. in ambient atmosphere and pressure (e.g. in an oven).

Example E2

Crystalline form E of compound (1) can be obtained in high purity by reaction compound (1) with fumaric acid to give the corresponding fumarate salt and subsequently reacting the isolated salt with a base to give free compound (1) again.

7 l ethylacetate are charged into a reaction vessel and 1.1 equivalent of fumaric acid (728.5 mmol=84.7 g) are added to the solvent. The solvent is heated to 60° C. thereby dissolving the fumaric acid to a large degree. One equivalent of compound (1) (336 g) dissolved in 10 l ethylacetate are added stepwise. A white suspension is quickly formed. The reaction mixture is stirred for 90 minutes then the mixture is allowed to cool to ambient temperature and stirred for another 2 days. The precipitated solid is isolated via filtration (G3 glass frit), washed three times with about 700 ml ethylacetate, dried by applying a strong air flow with the suction pump and then further dried at 40° C. in a vacuum oven at a pressure of below 2 mbar until no further loss of mass was observed.

The thus obtained solid (293 g) was charged into a reaction vessel together with 8 l distilled water. Whilst stirring at 150 rpm 610 ml diethylamine are added to the resulting white suspension. Subsequently, 200 ml of ethanol are added and the reaction mixture is stirred at 24° C. for 16 h. Then, the solid is isolated from the suspension via filtration (G3 glass frit) and slurried 4 times in 1 l of water. The resulting solid is dried overnight on a nutsch filter with suction. The resulting white solid was further dried for 2 days in a vacuum oven at 70° C. 250 g of (1) are isolated (74.4%).

XRPD analysis of the dried solid revealed it to be crystalline form E of compound (1).

F) Crystalline Form F

Crystalline form F was observed during an experiment in a multi-well plate. Approximately 5 mg of either crystalline forms D or A, or a mixture of crystalline forms D and E were charged into respective wells. 0.25 ml of a specific solvent were added to each well and the lid of the plate closed. The plate was shaken at 30° C. for 16 h. Subsequently, the plate was allowed to cool to RT. Upon opening, it was found, that part of the solid had been spread all over the plate. Residual solvent was removed by evaporation from the plate and the solid samples in the respective wells analyzed. The results are listed below in table 7.

TABLE 7

Multiwell experiment

| | Starting with polymorph D and E | Starting with polymorph A | Starting with polymorph E |
|---|---|---|---|
| Acetone | F | 83* | F |
| Acetonitrile | D | 83* | D |
| Dichloromethane | F | D | 83* |
| Ethylacetate | F | M | 75* |
| Diethylether | M | F | F |
| Hexane | F | F | M |
| Methy-ethyl-ketone | M | F | M |
| Methanol | K | K | K |
| Pentane | F | F | D + peaks |
| 1-Propanol | am** | F | 77 |
| 2-Propanol | am** | A | F |
| Ethanol | am** | F | M |
| Tetrahydrofurane | am** | E + peaks | D + peaks |
| Toluene | M | D + peaks | am** |
| tBME | F | F | M |
| Water | M | D | E + peaks |
| Acetone/Water | F | F | F |
| Acetone/Water__1 | F | F | F |
| Acetone/Water__2 | M | M | F |
| Tetrahydrofurane/Hexane | am** | M | M |

*numbers denote crystalline forms which were not further characterized
**am = amorphous or of poor crystallinity
"+ peaks" means that additional peaks were found in the XRPD of the solid, which were considered not to belong to the indicated crystalline form.

G) Crystalline Form G

General Procedure for Syntheses: See General Procedure for Syntheses of Crystalline Form A. In table 8 below, specific reaction conditions for syntheses of crystalline form G are listed.

TABLE 8

| Ex. | Crystalline form of starting material | Amount [mg] | Solvent/amount | T [° C.] | Reaction time [d] |
|---|---|---|---|---|---|
| G1 | E | 176.4 | Ethanol/15 ml; water/4.5 ml | 50 | 3 |
| G3 | L | 1210 | Ethanol/25 ml | 40 | 0.83 (20 h) |
| G4 | A | 1550 | Ethanol/175 ml | 75 -->0* | 0.65 (15.25 h)* |
| G5.1 | E | 106.1 | Ethanol | 40 | 0.75 |
| G5.2 | E | 115.7 | 1-Propanol/2.5 ml; Water/2.5.ml | 40 | 0.75 |

*15 min heated to 75° C., cooled to 0° C. during 6 h, stirred at 0° C. for 9 h.

H) Crystalline Form H

General Procedure for Syntheses: See General Procedure for Syntheses of Crystalline Form A. In table 9 below, specific reaction conditions for syntheses of crystalline form H are listed.

TABLE 9

| Ex. | Crystalline form of starting material | Amount [mg] | Solvent/amount | T [° C.] | Reaction time [d] |
|---|---|---|---|---|---|
| H3 | E | 105.8 | 2-Propanol/2.5 ml | 40 | 0.75 |
| H5 | E | 103 | 2-Propanol/2.5 ml | 40 | 0.75 |

Example H1

Interconversion Experiments

A mixture of two different crystalline forms of compound (1) was charged into a vial and 1.0 mL of 2-Propanol was added (details see table).

The vials were closed and the mixtures were stirred (by means of shaking, Eppendorf Thermomixer, 750 rpm at first, increased to 1000 rpm after 1 d) at elevated temperature (30±2° C.) for 7 days.

Subsequently, the mixtures were cooled to 20±2° C. and stirred for additional 2 hours.

The solids were then isolated via filtration using a suction filter. The air flow from the suction pump was applied for 2 to 3 hours to dry the isolated solid.

The results of the experiments are listed below in table 10:

TABLE 10

| Ex. | Mixture of crystalline forms/ [mg] | Solvent (1 ml) | Temperature/ ° C. (time) | resulting crystalline form |
|---|---|---|---|---|
| H1.1 | 23.1 mg E 22.6 mg C | 2-Propanol | 30 (7 d) 20 (2 h) | H |
| H1.2 | 22.6 mg E 22.2 mg L | 2-Propanol | 30 (7 d) 20 (2 h) | A + H |
| H1.4 | 23.3 mg E 24.2 mg C | 2-Propanol | 30 (7 d) 20 (2 h) | H |
| H1.5 | 22.8 mg E 23.4 mg L | 2-Propanol | 30 (7 d) 20 (2 h) | A + H |

I) Crystalline Form I

A sample of crystalline form C (characterized by X-ray diffraction) was stored for up to 4 months, during which, according to X-ray diffraction analysis, the sample converted to Polymorph I in three to four months.

It was observed that under the conditions of a variable Temperature x-ray diffraction experiment (STOE diffractometer, radiation CuKα, sample filled in quartz capillary) starting from crystalline form I upon heating in a temperature range from 30° C. to 10° C. the sample remained crystalline form I until it transformed into crystalline form J at higher temperature in the range from 110° C. to 130° C. Upon further heating in a temperature range from 140° C. to 160° C. the sample became poorly crystalline to amorphous. The sample remained poorly crystalline to amorphous upon cooling to 20° C.

J) Crystalline Form J 45 mg or 78 mg crystalline form C were stored in a vacuum oven at reduced pressure (10 mbar) at 25° C. for 24 h, at 41° C. for 24 h or at 65° C. for 72 h. In all cases crystalline form C transformed into crystalline form J.

K) Crystalline Form K

Example K1

39.6 mg of crystalline form C were stored in a vacuum oven at reduced pressure (5 to 10 mbar) at 50° C. for 16 h. It was found that crystalline form C had transformed into crystalline form K.

Example K2

99.5 mg of crystalline form C were stored in a vacuum oven C at reduced pressure (5 to 10 mbar) at 60° C. for 16 h. It was found that crystalline form C had transformed into crystalline form K.

L) Crystalline form L

General Procedure for Syntheses: See General Procedure for Syntheses of Crystalline Form A.

In table XXX below, specific reaction conditions for syntheses of crystalline form L are listed.

| Ex. | Crystalline form of starting material | Amount [mg] | Solvent/amount | T [° C.] | Reaction time |
|---|---|---|---|---|---|
| L1 | E | 102 | Toluene/2.5 ml | 40 | 16 h |
| L2 | A | 1110 | Toluene/30 ml | 40 | 64 h |
| L3 | E | 101 | Toluene/2.5 ml | 40 | 16 h |
| L4 | A | 83.9 | Toluene/1 ml | 30 | 19 d |

Q) Crystalline Form Q

Example Q1

Compound (1) (6.6 g) was charged to a 250 mL flask and suspended in toluene p.a. (1.25 moles; 132.00 mL; 115.00 g) and vigorously stirred with a magnetic stir bar for 3 h at 21° C. The solid was separated from the solvent by means of a suction filter, washed with 5 mL of toluene and subsequently washed again with another 10 mL of toluene.

Example Q2

1.08 g of crystalline form A of compound (1) was charged into a vial and 30 mL of toluene p.a. were added. A thick suspension was formed. The vial was closed and the suspension was stirred (by means of shaking, PLS shaker, 400 rpm) at elevated temperature (40° C.±2) for 22 h. The mixture was cooled to 22±2° C. and shaken for another 30 min. The solid was separated using a suction filter (G4) and dried by applying the air flow from the suction pump for 10 min. A white fluffy solid was produced.

1) Transformation of Crystalline Form Q into Amorphous Material.

31.1 mg of crystalline form Q of compound (1) was charged into a vial and 1.5 mL of an acetone/water mixture (8:2 vol/vol) was added. The vial was closed and the mixture (a suspension) was stirred (by means of shaking, Eppendorf Thermomixer, 1000 rpm) at room temperature (23±2° C.) for 7 days.

The solid was separated using a suction filter and dried by applying the air flow for an additional 15 minutes. The resulting solid was analyzed (SM1).

The solvent from the filtrate was let to evaporate (23±2° C.) in a fume hood to give a second solid material (SM2). This was also analyzed.

According to XRPD-analyses SM1 is a poorly crystalline material, SM2 amorphous.

Example S1

Chemical Stability of Crystalline Forms of Compound (1)

Samples of compound 1 in different crystalline forms were stored in open vials under controlled conditions at different temperatures and rel. humidities for 28 days. Prior to storage and after 14 and 28 days the content of compound (1) in the sample was determined via HPLC and the crystalline form was measured via XRPD.

The results of this stability study are listed below in table 12:

The data shows that the content of compound (1) of crystalline form A in the respective samples remains essentially unchanged after 28 days of open storage at the indicated temperatures and relative humidity.

Contrary to this, the other two ansolvate crystalline forms show a higher degree of chemical degradation after 28 days storage at the respective storage conditions, wherein this effect is more pronounced at 50° C. with crystalline form E than with D.

Of the three ansolvate forms tested, crystalline form A is observed to be the chemically most stable one.

Furthermore, it can be seen that crystalline form E transforms into different crystalline forms at 40° C. and a relative humidity of 75%. This is a disadvantage of crystalline form E compared to A and D, because it is advantageous that in the formulation of solid dosage forms the pharmaceutical active ingredient retains the same crystalline form. Be it during formulation and storage of the dosage form so that the desired pharmacokinetic properties of the dosage form are achieved after formulation and remain essentially stable over the shelf-life of the dosage form. Crystalline form C shows a comparable chemical stability to crystalline form A, but transforms into other crystalline forms during storage over 28 days at the indicated conditions.

Crystalline form B does not transform into different forms but it exhibits a higher degree of chemical degradation in the experiments, i.e. a lower chemical stability compared both to form A and C.

Example S2

Chemical Stability in Pharmaceutical Compositions

To test the chemical stability, i.e. compatibility of different crystalline forms of compound (1), solid multi component

TABLE 12

| Ex-No. | Initial solid form | Storage [d] | T[° C.] | Rel. humidity % r.H. | Resulting solid form | Content cmpd (1) [%] |
|---|---|---|---|---|---|---|
| S1-A1 | A | 0 | 50 | | A | 99.58 |
| | A | 14 | 50 | | A | 99.49 |
| | A | 28 | 50 | | A | 99.37 |
| S1-A2 | A | 0 | 40 | 75 | A | 99.58 |
| | A | 14 | 40 | 75 | A | 99.63 |
| | A | 28 | 40 | 75 | A | 99.39 |
| S1-B1 | B | 0 | 50 | | B | 84.85 |
| | B | 14 | 50 | | B | 82.63 |
| | B | 28 | 50 | | B | 81.26 |
| S1-B2 | B | 0 | 40 | 75 | B | 84.85 |
| | B | 14 | 40 | 75 | B | 84.21 |
| | B | 28 | 40 | 75 | B | 83.74 |
| S1-C1 | C | 0 | 50 | | C | 99.67 |
| | C | 14 | 50 | | P | 99.57 |
| | C | 28 | 50 | | P | 99.20 |
| S1-C2 | C | 0 | 40 | 75 | C | 99.67 |
| | C | 14 | 40 | 75 | J | 99.68 |
| | C | 28 | 40 | 75 | J | 99.44 |
| S1-D1 | D | 0 | 50 | | D | 84.61 |
| | D | 14 | 50 | | D | 84.65 |
| | D | 28 | 50 | | D | 83.54 |
| S1-D2 | D | 0 | 40 | 75 | D | 84.61 |
| | D | 14 | 40 | 75 | D | 84.27 |
| | D | 28 | 40 | 75 | D | 83.92 |
| S1-E1 | E | 0 | 50 | | E | 99.76 |
| | E | 14 | 50 | | E | 97.25 |
| | E | 28 | 50 | | E | 95.53 |
| S1-E2 | E | 0 | 40 | 75 | E | 99.76 |
| | E | 14 | 40 | 75 | G | 99.80 |
| | E | 28 | 40 | 75 | B | 99.50 | mixtures were prepared comprising well established excipients used for solid oral dosage form and having different functions therein. The single components of each mixture were exactly weighed and intensively triturated using a mortar and a pestle. Subsequently, 10% (w/w) of compound (1) (either crystalline form A or B) were added to the respective mixtures and triturated using the same method as for preparation of the excipient mixtures.

10 g of the final mixtures were separately filled into glass vials (open or closed) and stored under the conditions outlined below in table 13. Samples were taken and analyzed initially and after 1, 2 and 3 months with respect to the content of compound (1) within the mixtures.

The comparison of the data obtained for the two different crystalline forms demonstrate that chemical degradation of compound (1) occurred to a lesser degree over the duration of storage at higher temperatures (e.g. 50° C.) if the compound was present in crystalline form A. Consequently, crystalline form A demonstrates superior properties compared to crystalline form B with respect to chemical degradation, i.e. higher chemical stability, and therefore superior properties for the use in solid dosage forms.

TABLE 13

| Example | crystalline form | $T_{storage}$ | humidity | excipients | | | | 0 month | 1 month | 2 months | 3 months |
|---|---|---|---|---|---|---|---|---|---|---|---|
| S2-1A | A | 50° C. | dry | Microcrystalline cellulose | HPMC 6 mPas | L-HPC LH21 | magnesium stearate | 99.64 | 99.59 | 99.59 | 99.62 |
| S2-1B | B | | | | | | | 99.75 | 95.74 | 91.45 | 87.34 |
| S2-2A | A | 40° C. | 75% rel. hum. | Microcrystalline cellulose | HPMC 6 mPas | L-HPC LH21 | magnesium stearate | 90.64 | 99.61 | 99.60 | 99.66 |
| S2-2B | B | | | | | | | 99.69 | 99.53 | 98.57 | 99.39 |
| S2-3A | A | 50° C. | dry | Lactose monohydrate | PVP25 | Crospovidone | Talcum | 99.66 | 99.58 | 99.54 | 99.56 |
| S2-3B | B | | | | | | | 99.57 | 95.82 | 91.04 | 85.33 |
| S2-4A | A | 40° C. | 75% rel. hum. | Lactose monohydrate | PVP25 | Crospovidone | Talcum | 99.66 | 99.93 | 99.72 | 99.86 |
| S2-4B | B | | | | | | | 99.57 | 99.22 | 99.05 | 96.87 |

Example X1

Analysis—XRPD (X-Ray Powder Diffraction) or PXRD (Powder X-Ray Diffraction)

XRPD analyses were carried out in transmission geometry with a STOE StadiP or a Panalytical X'Pert Pro X-ray powder diffractometer in reflection geometry, monochromatised CuK radiation being used by means of a germanium monocrystal. Measurements were carried out in an angular range between 5° and 50° in 2θ. In general, the 2θ values have an error rate of ±0.2° in 2θ.

The samples were measured without any special treatment other than the application of slight pressure to get a flat surface. An ambient air atmosphere was used. Unless stated otherwise, measurements were performed at room temperature (i.e. 298 K (±5 K)).

In general a baseline correction of the measured diffractograms was done using the program WinXPow (STOE).

Crystalline Form A

Table 14 shows the peak list for crystalline form A. The uncertainty in the 2θ values is ±0.2° in 2θ; rel. I is the relative intensity of the respective peaks. Maximum relative intensity is 100.

TABLE 14

| d value [Å] | 2θ [°] | rel. I [%] |
|---|---|---|
| 11.5 | 7.7 | 27 |
| 10.2 | 8.7 | 33 |

TABLE 14-continued

| d value [Å] | 2θ [°] | rel. I [%] |
|---|---|---|
| 9.3 | 9.5 | 9 |
| 8.8 | 10.0 | 33 |
| 7.9 | 11.2 | 6 |
| 7.5 | 11.9 | 85 |
| 7.2 | 12.3 | 25 |
| 5.8 | 15.3 | 73 |
| 5.6 | 15.8 | 34 |
| 5.5 | 16.2 | 19 |
| 5.3 | 16.7 | 53 |
| 5.1 | 17.4 | 79 |
| 5.0 | 17.8 | 100 |
| 4.8 | 18.3 | 83 |
| 4.7 | 18.8 | 14 |
| 4.6 | 19.2 | 12 |
| 4.5 | 19.7 | 35 |
| 4.4 | 20.2 | 38 |
| 4.2 | 21.3 | 19 |
| 4.1 | 21.5 | 13 |
| 4.0 | 21.9 | 58 |
| 4.0 | 22.2 | 35 |

TABLE 14-continued

| d value [Å] | 2θ [°] | rel. I [%] |
|---|---|---|
| 3.9 | 22.5 | 29 |
| 3.9 | 23.1 | 15 |
| 3.7 | 23.9 | 18 |
| 3.6 | 24.8 | 15 |
| 3.5 | 25.2 | 7 |
| 3.5 | 25.7 | 14 |
| 3.4 | 26.2 | 29 |
| 3.3 | 27.1 | 38 |
| 3.2 | 27.9 | 7 |
| 3.2 | 28.2 | 10 |
| 3.1 | 28.5 | 14 |
| 3.1 | 29.0 | 6 |
| 3.1 | 29.2 | 5 |
| 3.0 | 29.6 | 7 |
| 3.0 | 30.0 | 4 |
| 2.9 | 30.4 | 11 |
| 2.9 | 31.1 | 13 |
| 2.8 | 31.6 | 5 |
| 2.7 | 32.7 | 10 |
| 2.7 | 33.5 | 5 |
| 2.6 | 34.1 | 9 |
| 2.6 | 34.9 | 6 |
| 2.5 | 36.5 | 5 |
| 2.4 | 37.4 | 8 |
| 2.4 | 38.2 | 6 |
| 2.3 | 38.9 | 5 |
| 2.3 | 39.1 | 4 |
| 2.2 | 40.1 | 7 |
| 2.2 | 41.2 | 5 |
| 2.2 | 41.9 | 4 |
| 2.1 | 42.6 | 5 |
| 2.1 | 43.0 | 3 |

TABLE 14-continued

| d value [Å] | 2θ [°] | rel. I [%] |
|---|---|---|
| 2.1 | 43.7 | 11 |
| 2.0 | 44.4 | 4 |
| 2.0 | 45.0 | 2 |
| 1.9 | 48.0 | 4 |

Crystalline Form B

Table 15 shows the peak list for crystalline form B. The uncertainty in the 2θ values is ±0.2° in 2θ; rel. I is the relative intensity of the respective peaks. Maximum intensity is 100.

TABLE 15

| d value [Å] | 2θ [°] | rel. I [%] |
|---|---|---|
| 12.9 | 6.8 | 40 |
| 12.0 | 7.3 | 29 |
| 8.8 | 10.0 | 4 |
| 8.6 | 10.3 | 10 |
| 7.6 | 11.6 | 9 |
| 7.3 | 12.1 | 100 |
| 6.8 | 13.0 | 15 |
| 6.5 | 13.7 | 21 |
| 6.3 | 14.1 | 39 |
| 5.7 | 15.5 | 30 |
| 5.6 | 15.8 | 4 |
| 5.4 | 16.3 | 7 |
| 5.3 | 16.8 | 11 |
| 5.0 | 17.6 | 12 |
| 4.9 | 18.0 | 56 |
| 4.8 | 18.4 | 52 |
| 4.7 | 18.7 | 81 |
| 4.6 | 19.3 | 18 |
| 4.5 | 19.5 | 14 |
| 4.5 | 19.8 | 46 |
| 4.4 | 20.2 | 3 |
| 4.3 | 20.8 | 38 |
| 4.0 | 22.1 | 28 |
| 4.0 | 22.4 | 19 |
| 3.9 | 22.7 | 9 |
| 3.9 | 23.0 | 5 |
| 3.8 | 23.3 | 12 |
| 3.7 | 24.0 | 2 |
| 3.6 | 24.4 | 10 |
| 3.6 | 25.0 | 4 |
| 3.5 | 25.4 | 12 |
| 3.4 | 26.2 | 8 |
| 3.3 | 26.9 | 7 |
| 3.3 | 27.4 | 3 |
| 3.2 | 27.8 | 8 |
| 3.1 | 28.3 | 46 |
| 3.1 | 29.2 | 5 |
| 3.0 | 29.5 | 3 |
| 3.0 | 29.7 | 5 |
| 3.0 | 30.2 | 2 |
| 2.9 | 30.8 | 4 |
| 2.9 | 31.3 | 3 |
| 2.8 | 31.9 | 4 |
| 2.8 | 32.3 | 3 |
| 2.7 | 33.4 | 4 |
| 2.6 | 34.6 | 2 |
| 2.5 | 36.4 | 3 |
| 2.4 | 36.9 | 4 |
| 2.4 | 37.3 | 4 |
| 2.4 | 37.6 | 7 |
| 2.3 | 39.9 | 6 |
| 2.2 | 40.6 | 4 |
| 2.2 | 41.3 | 3 |
| 2.1 | 42.8 | 5 |
| 2.0 | 44.3 | 3 |
| 2.0 | 45.0 | 2 |
| 1.9 | 48.7 | 2 |

Crystalline Form C

Table 16 shows the peak list for crystalline form C. The uncertainty in the 2θ values is ±0.2° in 2θ; rel. I is the relative intensity of the respective peaks. Maximum relative intensity is 100.

TABLE 16

| d value [Å] | 2θ [°] | rel. I [%] |
|---|---|---|
| 12.7 | 7.0 | 30 |
| 12.4 | 7.1 | 42 |
| 10.7 | 8.3 | 6 |
| 9.1 | 9.7 | 51 |
| 7.8 | 11.3 | 31 |
| 7.6 | 11.6 | 55 |
| 7.1 | 12.5 | 46 |
| 6.8 | 13.0 | 58 |
| 6.3 | 13.9 | 60 |
| 6.2 | 14.3 | 32 |
| 5.9 | 15.1 | 16 |
| 5.8 | 15.4 | 19 |
| 5.1 | 17.5 | 8 |
| 5.0 | 17.9 | 100 |
| 4.5 | 19.8 | 6 |
| 4.4 | 20.3 | 8 |
| 4.2 | 21.0 | 30 |
| 4.2 | 21.1 | 29 |
| 4.0 | 22.2 | 5 |
| 3.9 | 22.6 | 19 |
| 3.9 | 23.0 | 13 |
| 3.8 | 23.4 | 9 |
| 3.8 | 23.6 | 16 |
| 3.7 | 24.1 | 19 |
| 3.5 | 25.1 | 6 |
| 3.4 | 26.3 | 23 |
| 3.3 | 26.7 | 8 |
| 3.3 | 27.0 | 9 |
| 3.2 | 27.7 | 4 |
| 3.2 | 28.2 | 3 |
| 3.1 | 29.2 | 6 |
| 3.0 | 29.8 | 5 |
| 2.9 | 31.3 | 4 |
| 2.8 | 31.7 | 8 |
| 2.7 | 33.3 | 5 |
| 2.4 | 37.0 | 7 |
| 2.3 | 39.7 | 4 |
| 2.1 | 42.9 | 5 |
| 1.9 | 47.4 | 4 |

Crystalline Form D

Table 17 shows the peak list for crystalline form D. The uncertainty in the 2θ values is ±0.2° in 2θ; rel. I is the relative intensity of the respective peaks. Maximum relative intensity is 100.

TABLE 17

| d value [Å] | 2θ [°] | rel. I [%] |
|---|---|---|
| 10.2 | 8.7 | 100 |
| 8.0 | 11.0 | 15 |
| 7.8 | 11.3 | 10 |
| 7.6 | 11.6 | 22 |
| 7.1 | 12.5 | 10 |
| 6.5 | 13.7 | 9 |
| 5.6 | 15.8 | 3 |
| 5.4 | 16.6 | 27 |
| 5.1 | 17.2 | 23 |
| 5.1 | 17.5 | 15 |
| 4.9 | 18.2 | 11 |
| 4.4 | 20.0 | 20 |
| 4.2 | 20.9 | 4 |
| 4.2 | 21.2 | 24 |
| 4.1 | 21.7 | 7 |
| 4.0 | 22.0 | 6 |
| 3.9 | 22.7 | 10 |

TABLE 17-continued

| d value [Å] | 2θ [°] | rel. I [%] |
|---|---|---|
| 3.8 | 23.2 | 3 |
| 3.7 | 23.9 | 5 |
| 3.6 | 24.4 | 4 |
| 3.6 | 25.0 | 6 |
| 3.5 | 25.5 | 5 |
| 3.4 | 26.0 | 4 |
| 3.4 | 26.3 | 10 |
| 3.3 | 27.1 | 2 |
| 3.3 | 27.4 | 2 |
| 3.2 | 27.7 | 5 |
| 3.1 | 28.4 | 5 |
| 3.1 | 28.8 | 6 |
| 3.0 | 29.5 | 5 |
| 2.7 | 33.3 | 3 |
| 2.7 | 33.6 | 3 |
| 2.1 | 42.4 | 3 |
| 2.0 | 46.0 | 2 |

Crystalline Form E

Table 18 shows the peak list for crystalline form E. The uncertainty in the 2θ values is ±0.2° in 2θ; rel. I is the relative intensity of the respective peaks. Maximum relative intensity is 100.

TABLE 18

| d value [Å] | 2θ [°] | rel. I [%] |
|---|---|---|
| 12.8 | 6.9 | 35 |
| 10.9 | 8.1 | 29 |
| 10.2 | 8.7 | 4 |
| 9.2 | 9.6 | 6 |
| 9.0 | 9.8 | 6 |
| 8.5 | 10.4 | 18 |
| 8.3 | 10.6 | 9 |
| 7.3 | 12.1 | 10 |
| 7.0 | 12.5 | 8 |
| 6.4 | 13.8 | 17 |
| 6.4 | 13.9 | 16 |
| 6.2 | 14.3 | 7 |
| 5.9 | 15.1 | 4 |
| 5.6 | 15.9 | 2 |
| 5.4 | 16.4 | 12 |
| 5.3 | 16.6 | 14 |
| 5.2 | 16.9 | 14 |
| 5.0 | 17.7 | 6 |
| 5.0 | 17.9 | 16 |
| 4.8 | 18.3 | 100 |
| 4.8 | 18.7 | 10 |
| 4.7 | 18.8 | 4 |
| 4.7 | 19.0 | 11 |
| 4.6 | 19.2 | 6 |
| 4.6 | 19.4 | 4 |
| 4.5 | 19.6 | 8 |
| 4.4 | 19.9 | 8 |
| 4.3 | 20.8 | 22 |
| 4.2 | 21.1 | 13 |
| 4.1 | 21.9 | 3 |
| 4.0 | 22.2 | 7 |
| 3.9 | 22.6 | 5 |
| 3.9 | 23.0 | 6 |
| 3.8 | 23.7 | 7 |
| 3.7 | 24.0 | 5 |
| 3.6 | 24.6 | 3 |
| 3.6 | 24.9 | 2 |
| 3.5 | 25.3 | 4 |
| 3.4 | 26.2 | 4 |
| 3.3 | 27.2 | 3 |
| 3.2 | 27.5 | 10 |
| 3.2 | 27.8 | 9 |
| 3.2 | 28.1 | 16 |
| 3.1 | 29.0 | 2 |
| 3.0 | 29.4 | 2 |

TABLE 18-continued

| d value [Å] | 2θ [°] | rel. I [%] |
|---|---|---|
| 2.8 | 32.3 | 2 |
| 2.6 | 34.4 | 4 |
| 2.5 | 36.2 | 1 |
| 2.3 | 38.6 | 2 |
| 2.2 | 40.5 | 2 |
| 2.1 | 42.9 | 2 |

Crystalline Form F

Table 19 shows the peak list for crystalline form F. The uncertainty in the 2θ values is ±0.2° in 2θ; rel. I is the relative intensity of the respective peaks. Maximum relative intensity is 100.

TABLE 19

| d value [Å] | 2θ [°] | rel. I [%] |
|---|---|---|
| 10.5 | 8.4 | 8 |
| 10.2 | 8.7 | 38 |
| 9.5 | 9.3 | 1 |
| 7.8 | 11.3 | 16 |
| 7.1 | 12.5 | 100 |
| 6.5 | 13.6 | 1 |
| 6.0 | 14.6 | 1 |
| 5.6 | 15.7 | 1 |
| 5.4 | 16.6 | 6 |
| 5.3 | 16.7 | 15 |
| 4.9 | 18.2 | 4 |
| 4.8 | 18.4 | 11 |
| 4.4 | 19.9 | 6 |
| 4.2 | 20.9 | 47 |
| 4.2 | 21.1 | 7 |
| 4.1 | 21.7 | 4 |
| 3.9 | 22.6 | 6 |
| 3.7 | 23.9 | 4 |
| 3.7 | 24.3 | 2 |
| 3.5 | 25.2 | 14 |
| 3.5 | 25.5 | 7 |
| 3.4 | 25.9 | 13 |
| 3.4 | 26.3 | 10 |
| 3.3 | 27.1 | 2 |
| 3.1 | 28.7 | 2 |
| 3.0 | 29.4 | 5 |
| 2.9 | 30.5 | 4 |
| 2.9 | 31.1 | 1 |
| 2.8 | 32.1 | 1 |
| 2.7 | 33.2 | 8 |
| 2.6 | 34.2 | 2 |
| 2.6 | 34.6 | 1 |

Crystalline Form G

Table 20 shows the peak list for crystalline form G. The uncertainty in the 2θ values is ±0.2° in 2θ; rel. I is the relative intensity of the respective peaks. Maximum relative intensity is 100.

TABLE 20

| d value [Å] | 2θ [°] | rel. I [%] |
|---|---|---|
| 13.3 | 6.6 | 100 |
| 12.6 | 7.0 | 12 |
| 11.0 | 8.0 | 30 |
| 9.4 | 9.4 | 6 |
| 8.5 | 10.4 | 11 |
| 7.5 | 11.8 | 10 |
| 7.1 | 12.4 | 14 |
| 6.6 | 13.3 | 16 |
| 6.4 | 13.9 | 18 |
| 5.9 | 15.1 | 4 |

TABLE 20-continued

| d value [Å] | 2θ [°] | rel. I [%] |
|---|---|---|
| 5.7 | 15.5 | 11 |
| 5.7 | 15.6 | 10 |
| 5.0 | 17.6 | 13 |
| 4.9 | 18.0 | 59 |
| 4.8 | 18.4 | 43 |
| 4.7 | 18.9 | 39 |
| 4.6 | 19.3 | 27 |
| 4.5 | 19.7 | 13 |
| 4.4 | 19.9 | 8 |
| 4.4 | 20.3 | 5 |
| 4.3 | 20.6 | 7 |
| 4.2 | 21.3 | 4 |
| 4.1 | 21.6 | 5 |
| 3.9 | 22.5 | 6 |
| 3.8 | 23.3 | 10 |
| 3.6 | 24.6 | 5 |
| 3.5 | 25.3 | 3 |
| 3.4 | 26.4 | 2 |
| 3.3 | 27.0 | 8 |
| 3.2 | 27.4 | 9 |
| 3.2 | 27.7 | 10 |
| 3.1 | 28.5 | 4 |

Crystalline Form H

Table 21 shows the peak list for crystalline form H. The uncertainty in the 2θ values is ±0.2° in 2θ; rel. I is the relative intensity of the respective peaks. Maximum relative intensity is 100.

TABLE 21

| d value [Å] | 2θ [°] | rel. I [%] |
|---|---|---|
| 17.3 | 5.1 | 4 |
| 12.4 | 7.1 | 32 |
| 11.9 | 7.4 | 10 |
| 11.0 | 8.0 | 79 |
| 8.8 | 10.1 | 5 |
| 8.5 | 10.4 | 23 |
| 7.8 | 11.4 | 4 |
| 7.5 | 11.8 | 8 |
| 7.3 | 12.1 | 4 |
| 7.1 | 12.4 | 12 |
| 6.8 | 13.0 | 12 |
| 6.4 | 13.8 | 9 |
| 6.2 | 14.3 | 12 |
| 6.1 | 14.5 | 5 |
| 6.0 | 14.9 | 7 |
| 5.7 | 15.5 | 9 |
| 5.5 | 16.0 | 5 |
| 5.5 | 16.0 | 6 |
| 5.3 | 16.8 | 15 |
| 5.2 | 17.1 | 19 |
| 5.1 | 17.3 | 40 |
| 5.1 | 17.5 | 27 |
| 5.0 | 17.7 | 60 |
| 4.9 | 18.1 | 73 |
| 4.9 | 18.2 | 100 |
| 4.7 | 18.8 | 44 |
| 4.6 | 19.2 | 66 |
| 4.6 | 19.4 | 19 |
| 4.5 | 19.7 | 74 |
| 4.4 | 19.9 | 6 |
| 4.4 | 20.2 | 15 |
| 4.3 | 20.7 | 44 |
| 4.2 | 20.9 | 26 |
| 4.2 | 21.1 | 8 |
| 4.2 | 21.2 | 8 |
| 4.1 | 21.5 | 9 |
| 4.0 | 22.3 | 6 |
| 3.9 | 22.8 | 20 |
| 3.8 | 23.3 | 6 |
| 3.7 | 23.7 | 8 |

TABLE 21-continued

| d value [Å] | 2θ [°] | rel. I [%] |
|---|---|---|
| 3.7 | 24.3 | 6 |
| 3.6 | 24.6 | 6 |
| 3.6 | 24.9 | 4 |
| 3.5 | 25.4 | 4 |
| 3.5 | 25.7 | 9 |
| 3.4 | 26.1 | 4 |
| 3.3 | 26.7 | 8 |
| 3.3 | 27.0 | 10 |
| 3.3 | 27.2 | 14 |
| 3.2 | 27.6 | 15 |
| 3.2 | 28.1 | 18 |
| 3.2 | 28.3 | 27 |
| 3.1 | 28.9 | 7 |
| 3.1 | 29.1 | 5 |
| 3.0 | 29.3 | 7 |
| 3.0 | 29.9 | 3 |
| 2.9 | 30.4 | 8 |
| 2.9 | 30.9 | 4 |
| 2.9 | 31.3 | 5 |
| 2.8 | 31.7 | 3 |
| 2.8 | 32.3 | 5 |
| 2.7 | 32.9 | 7 |
| 2.7 | 33.4 | 7 |
| 2.6 | 34.6 | 2 |
| 2.6 | 35.1 | 3 |
| 2.5 | 35.9 | 5 |
| 2.4 | 37.0 | 8 |
| 2.4 | 37.5 | 6 |
| 2.3 | 38.3 | 3 |
| 2.3 | 38.8 | 5 |
| 2.2 | 40.4 | 3 |
| 2.2 | 40.7 | 4 |
| 2.2 | 41.1 | 2 |
| 2.2 | 41.5 | 3 |
| 2.1 | 42.5 | 5 |
| 2.0 | 45.9 | 3 |
| 1.9 | 47.6 | 3 |
| 1.8 | 49.3 | 3 |

Crystalline Form I

Table 22 shows the peak list for crystalline form I. The uncertainty in the 2θ values is ±0.2° in 2θ; rel. I is the relative intensity of the respective peaks. Maximum relative intensity is 100.

TABLE 22

| d value [Å] | 2θ [°] | rel. I [%] |
|---|---|---|
| 12.5 | 7.1 | 99 |
| 9.1 | 9.7 | 47 |
| 8.0 | 11.0 | 34 |
| 7.5 | 11.8 | 78 |
| 7.0 | 12.7 | 74 |
| 6.2 | 14.2 | 59 |
| 6.1 | 14.6 | 51 |
| 5.9 | 15.1 | 44 |
| 5.6 | 15.7 | 50 |
| 5.4 | 16.4 | 31 |
| 5.1 | 17.5 | 100 |
| 4.9 | 17.9 | 35 |
| 4.7 | 18.9 | 32 |
| 4.5 | 19.6 | 49 |
| 4.2 | 21.2 | 41 |
| 4.1 | 21.6 | 41 |
| 3.9 | 22.9 | 42 |
| 3.4 | 26.3 | 31 |

Crystalline Form J

Table 23 shows the peak list for crystalline form J. The uncertainty in the 2θ values is ±0.2° in 2θ; rel. I is the relative intensity of the respective peaks. Maximum relative intensity is 100.

TABLE 23

| d value [Å] | 2θ [°] | rel. I [%] |
|---|---|---|
| 12.5 | 7.1 | 100 |
| 11.8 | 7.5 | 18 |
| 9.7 | 9.1 | 43 |
| 7.9 | 11.1 | 73 |
| 7.1 | 12.4 | 20 |
| 6.1 | 14.5 | 73 |
| 5.9 | 15.0 | 50 |
| 5.8 | 15.3 | 34 |
| 5.4 | 16.6 | 51 |
| 5.3 | 16.8 | 61 |
| 5.2 | 17.0 | 72 |
| 5.0 | 17.9 | 29 |
| 4.8 | 18.4 | 22 |
| 4.5 | 19.7 | 97 |
| 4.3 | 20.4 | 70 |
| 4.2 | 21.3 | 29 |
| 3.8 | 23.1 | 55 |
| 3.5 | 25.3 | 21 |
| 3.4 | 26.1 | 27 |
| 3.4 | 26.4 | 28 |
| 3.2 | 28.2 | 24 |
| 3.1 | 28.8 | 25 |
| 3.0 | 30.3 | 11 |
| 2.6 | 34.1 | 13 |
| 2.4 | 37.0 | 11 |
| 2.3 | 39.3 | 12 |
| 2.1 | 42.4 | 11 |
| 2.1 | 43.9 | 10 |

Crystalline Form K

Table 24 shows the peak list for crystalline form K. The uncertainty in the 2θ values is ±0.2° in 2θ; rel. I is the relative intensity of the respective peaks. Maximum relative intensity is 100.

TABLE 24

| d value [Å] | 2θ [°] | rel. I [%] |
|---|---|---|
| 12.4 | 7.1 | 100 |
| 8.8 | 10.0 | 56 |
| 7.9 | 11.2 | 42 |
| 7.0 | 12.7 | 17 |
| 6.2 | 14.3 | 83 |
| 5.9 | 15.1 | 50 |
| 5.8 | 15.4 | 53 |
| 5.4 | 16.4 | 27 |
| 5.3 | 16.8 | 23 |
| 4.6 | 19.5 | 76 |
| 4.5 | 19.9 | 52 |
| 4.2 | 21.4 | 28 |
| 4.0 | 22.4 | 21 |
| 3.9 | 23.0 | 13 |
| 3.6 | 24.4 | 17 |
| 3.3 | 26.7 | 27 |
| 3.2 | 27.7 | 30 |
| 2.7 | 33.2 | 12 |
| 2.4 | 37.0 | 11 |

Crystalline Form L

Table 25 shows the peak list for crystalline form L. The uncertainty in the 2θ values is ±0.2° in 2θ; rel. I is the relative intensity of the respective peaks. Maximum relative intensity is 100.

TABLE 25

| d value [Å] | 2θ [°] | rel. I [%] |
|---|---|---|
| 11.4 | 7.7 | 28 |
| 10.9 | 8.1 | 100 |
| 8.3 | 10.7 | 5 |
| 7.9 | 11.2 | 4 |
| 7.4 | 12.0 | 66 |
| 6.2 | 14.4 | 9 |
| 6.0 | 14.9 | 16 |
| 5.6 | 15.7 | 9 |
| 5.4 | 16.4 | 35 |
| 5.3 | 16.8 | 13 |
| 5.2 | 17.1 | 91 |
| 4.9 | 18.0 | 20 |
| 4.9 | 18.2 | 4 |
| 4.7 | 18.7 | 7 |
| 4.6 | 19.3 | 7 |
| 4.4 | 20.1 | 68 |
| 4.3 | 20.4 | 8 |
| 4.3 | 20.6 | 4 |
| 4.2 | 21.2 | 39 |
| 4.1 | 21.5 | 15 |
| 4.1 | 21.9 | 39 |
| 3.9 | 22.5 | 8 |
| 3.9 | 23.1 | 8 |
| 3.8 | 23.3 | 9 |
| 3.7 | 24.0 | 9 |
| 3.7 | 24.3 | 41 |
| 3.6 | 25.0 | 2 |
| 3.4 | 25.8 | 21 |
| 3.4 | 26.3 | 5 |
| 3.3 | 26.8 | 11 |
| 3.3 | 27.0 | 5 |
| 3.3 | 27.3 | 6 |
| 3.2 | 27.5 | 10 |
| 3.2 | 27.8 | 4 |
| 3.2 | 28.0 | 4 |
| 3.1 | 28.5 | 17 |
| 3.1 | 29.0 | 14 |
| 3.0 | 30.2 | 3 |
| 2.9 | 30.6 | 1 |
| 2.9 | 31.0 | 4 |
| 2.9 | 31.3 | 5 |
| 2.8 | 31.6 | 2 |
| 2.8 | 32.0 | 3 |
| 2.7 | 33.0 | 3 |
| 2.7 | 33.8 | 4 |
| 2.6 | 34.4 | 3 |
| 2.6 | 34.9 | 2 |
| 2.5 | 35.8 | 7 |
| 2.4 | 36.7 | 2 |
| 2.4 | 37.5 | 2 |
| 2.4 | 38.0 | 3 |
| 2.3 | 38.7 | 3 |
| 2.3 | 39.1 | 3 |
| 2.3 | 40.0 | 3 |
| 2.2 | 40.8 | 3 |
| 2.2 | 41.1 | 3 |
| 2.2 | 41.9 | 3 |
| 2.1 | 42.5 | 2 |
| 2.1 | 43.8 | 2 |
| 2.0 | 44.7 | 3 |
| 2.0 | 45.3 | 3 |
| 2.0 | 45.8 | 2 |
| 1.9 | 48.5 | 3 |
| 1.9 | 49.0 | 2 |
| 1.8 | 49.6 | 3 |

Crystalline Form Q

Table 26 shows the peak list for crystalline form Q. The uncertainty in the 2θ values is ±0.2° in 2θ; rel. I is the relative intensity of the respective peaks. Maximum relative intensity is 100.

TABLE 26

| D value [Å] | 2θ [°] | rel. I [%] |
|---|---|---|
| 10.7 | 8.2 | 49 |
| 10.2 | 8.6 | 40 |
| 8.1 | 11.0 | 23 |
| 7.7 | 11.5 | 18 |
| 7.3 | 12.0 | 26 |
| 6.1 | 14.5 | 7 |
| 5.9 | 15.0 | 10 |
| 5.4 | 16.5 | 28 |
| 5.2 | 17.2 | 100 |
| 5.0 | 17.6 | 12 |
| 4.9 | 18.0 | 12 |
| 4.4 | 20.1 | 19 |
| 4.2 | 21.3 | 18 |
| 4.1 | 21.6 | 16 |
| 4.0 | 22.0 | 13 |
| 3.9 | 22.6 | 7 |
| 3.6 | 24.4 | 18 |
| 3.6 | 25.1 | 10 |
| 3.4 | 26.0 | 10 |
| 3.1 | 28.5 | 11 |
| 3.1 | 29.2 | 5 |

Calculated XRPD

X-ray powder diffractogram (XRPD) may be calculated from a single crystal diffractogram (SCXRD) measured using MoK radiation having a wavelength of 0.71073 Å at 100 K (±5 K) or 130 K (±5 K) or 230 K (±5 K). Due to the fact that the SCXRD was determined at 100 K (±5 K) or 130 K (±5 K) or at 230 K (±5 K), the peak positions determined by a XRPD measured at 298 K (±5 K) may differ because of temperature dependent variations of the lattice parameters of the unit cell. Therefore, the uncertainty in the 2θ values is ±1.0°, preferably ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ.

SCXRD (Single Crystal X-Ray Diffraction)
Polymorph A (Measure at Low Temperature)

SCXRD analyses of crystalline forms A was carried out with a Bruker D8-goniometer with SMART APEX CCD area detector at 100 K (±5 K) using MoKα radiation (wavelength of 0.71073 Å, Incoatec microsource, multilayer optics).

TABLE 27

Crystal data and structure refinement for ansolvat__lt.

| | |
|---|---|
| Empirical formula | C33H34FN3O |
| Formula weight | 507.63 |
| Temperature | 100(2) K |
| Wavelength | .71073 Å |
| Crystal system | Monoclinic |
| Space group | P 21/c |
| Unit cell dimensions | a = 12.1568(7) Å alpha = 90 deg. |
| | b = 21.6289(12) Å beta = 113.3610(10) deg. |
| | c = 10.9424(6) Å gamma = 90 deg. |
| Volume | 2641.3(3) Å$^3$ |
| Z | 4 |
| Density (calculated) | 1.277 Mg/m$^3$ |
| Absorption coefficient | 0.082 mm$^{-1}$ |
| F(000) | 1080 |
| Crystal size | 0.45 × 0.21 × 0.08 mm |
| Theta range for data collection | 1.82 to 28.30 deg. |
| Index ranges | −15 <= h <= 16, −27 <= k <= 28, −14 <= l <= 14 |
| Reflections collected | 30878 |
| Independent reflections | 6534 [R(int) = 0.0477] |
| Absorption correction | None |
| Refinement method | Full-matrix least-squares on F$^2$ |
| Data/restraints/parameters | 6534/0/346 |
| Goodness-of-fit on F$^2$ | 1.000 |
| Final R indices [I > 2sigma(I)] | R1 = 0.0497, wR2 = 0.1281 |
| R indices (all data) | R1 = 0.0643, wR2 = 0.1405 |
| Largest diff. peak and hole | .496 and −.260 e · Å$^{-3}$ |

TABLE 28

Atomic coordinates (×10$^4$) and equivalent isotropic displacement parameters (Å$^2$ × 10$^3$). U(eq) is defined as one third of the trace of the orthogonalized Uij tensor.

| | x | y | z | U(eq) |
|---|---|---|---|---|
| F(1) | −1204(1) | 86(1) | 877(1) | 37(1) |
| O(1) | 5159(1) | 2358(1) | 3238(1) | 21(1) |
| N(1) | 496(1) | 2509(1) | 936(1) | 20(1) |
| N(2) | 4304(1) | 1813(1) | 1278(1) | 17(1) |
| N(3) | 4431(1) | 322(1) | 3012(1) | 18(1) |
| C(1) | −626(1) | 567(1) | 1675(2) | 23(1) |
| C(2) | −32(1) | 976(1) | 1184(2) | 20(1) |
| C(3) | 611(1) | 1466(1) | 1983(1) | 18(1) |
| C(4) | 1255(1) | 1945(1) | 1456(1) | 17(1) |
| C(5) | −720(1) | 2372(1) | −34(2) | 25(1) |
| C(6) | 389(2) | 2911(1) | 1959(2) | 23(1) |
| C(7) | 1548(1) | 1693(1) | 300(1) | 18(1) |
| C(8) | 2454(1) | 1166(1) | 685(1) | 18(1) |
| C(9) | 3675(1) | 1347(1) | 1802(1) | 17(1) |
| C(10) | 5036(1) | 2266(1) | 2081(1) | 16(1) |
| C(11) | 5663(1) | 2682(1) | 1476(1) | 18(1) |
| C(12) | 6456(1) | 3089(1) | 2250(1) | 19(1) |
| C(13) | 7072(1) | 3566(1) | 1805(2) | 20(1) |
| C(14) | 7665(1) | 4040(1) | 2684(2) | 26(1) |
| C(15) | 8186(2) | 4527(1) | 2275(2) | 33(1) |
| C(16) | 8115(2) | 4547(1) | 980(2) | 34(1) |
| C(17) | 7544(1) | 4073(1) | 99(2) | 29(1) |
| C(18) | 7032(1) | 3584(1) | 506(2) | 23(1) |
| C(19) | 4616(1) | 1555(1) | 200(1) | 21(1) |
| C(20) | 5609(1) | 1070(1) | 749(2) | 23(1) |
| C(21) | 5339(1) | 652(1) | 1693(1) | 19(1) |
| C(22) | 4483(1) | 790(1) | 2172(1) | 18(1) |
| C(23) | 5276(1) | −121(1) | 3095(1) | 18(1) |
| C(24) | 5862(1) | 74(1) | 2273(1) | 19(1) |
| C(25) | 6781(1) | −296(1) | 2196(2) | 22(1) |
| C(26) | 7101(1) | −831(1) | 2948(2) | 26(1) |
| C(27) | 6502(1) | −1016(1) | 3749(2) | 25(1) |
| C(28) | 5576(1) | −666(1) | 3830(2) | 22(1) |
| C(29) | 3343(1) | 1574(1) | 2947(1) | 17(1) |
| C(30) | 2476(1) | 2124(1) | 2558(1) | 17(1) |
| C(31) | 607(1) | 1519(1) | 3261(1) | 20(1) |
| C(32) | −3(1) | 1097(1) | 3720(2) | 23(1) |
| C(33) | −630(1) | 608(1) | 2927(2) | 25(1) |

TABLE 29

Bond lengths [Å] and angles [deg]

| | | | |
|---|---|---|---|
| F(1)—C(1) | 1.3620(18) | C(8)—H(8B) | .9900 |
| O(1)—C(10) | 1.2307(17) | C(9)—C(22) | 1.506(2) |
| N(1)—C(6) | 1.4639(19) | C(9)—C(29) | 1.5408(19) |
| N(1)—C(5) | 1.4685(19) | C(10)—C(11) | 1.4938(19) |

TABLE 29-continued

| Bond lengths [A] and angles [deg] | | | |
|---|---|---|---|
| N(1)—C(4) | 1.4991(18) | C(11)—C(12) | 1.332(2) |
| N(2)—C(10) | 1.3785(18) | C(11)—H(11) | .9500 |
| N(2)—C(19) | 1.4855(18) | C(12)—C(13) | 1.466(2) |
| N(2)—C(9) | 1.5091(17) | C(12)—H(12) | .9500 |
| N(3)—C(23) | 1.3802(18) | C(13)—C(14) | 1.396(2) |
| N(3)—C(22) | 1.3856(18) | C(13)—C(18) | 1.403(2) |
| N(3)—H(3N) | .8663 | C(14)—C(15) | 1.391(2) |
| C(1)—C(33) | 1.375(2) | C(14)—H(14) | .9500 |
| C(1)—C(2) | 1.378(2) | C(15)—C(16) | 1.386(3) |
| C(2)—C(3) | 1.398(2) | C(15)—H(15) | .9500 |
| C(2)—H(2) | .9500 | C(16)—C(17) | 1.389(3) |
| C(3)—C(31) | 1.405(2) | C(16)—H(16) | .9500 |
| C(3)—C(4) | 1.542(2) | C(17)—C(18) | 1.388(2) |
| C(4)—C(7) | 1.5436(19) | C(17)—H(17) | .9500 |
| C(4)—C(30) | 1.5447(19) | C(18)—H(18) | .9500 |
| C(5)—H(5A) | .9800 | C(19)—C(20) | 1.531(2) |
| C(5)—H(5B) | .9800 | C(19)—H(19A) | .9900 |
| C(5)—H(5C) | .9800 | C(19)—H(19B) | .9900 |
| C(6)—H(6A) | .9800 | C(20)—C(21) | 1.503(2) |
| C(6)—H(6B) | .9800 | C(20)—H(20A) | .9900 |
| C(6)—H(6C) | .9800 | C(20)—H(20B) | .9900 |
| C(7)—C(8) | 1.523(2) | C(21)—C(22) | 1.371(2) |
| C(7)—H(7A) | .9900 | C(21)—C(24) | 1.432(2) |
| C(7)—H(7B) | .9900 | C(23)—C(28) | 1.393(2) |
| C(8)—C(9) | 1.5518(19) | C(23)—C(24) | 1.415(2) |
| C(8)—H(8A) | .9900 | C(24)—C(25) | 1.403(2) |
| C(25)—C(26) | 1.385(2) | N(1)—C(4)—C(3) | 111.21(11) |
| C(25)—H(25) | .9500 | C(7)—C(4)—C(3) | 112.67(12) |
| C(26)—C(27) | 1.401(2) | N(1)—C(4)—C(30) | 110.43(11) |
| C(26)—H(26) | .9500 | C(7)—C(4)—C(30) | 105.39(11) |
| C(27)—C(28) | 1.388(2) | C(3)—C(4)—C(30) | 110.44(11) |
| C(27)—H(27) | .9500 | N(1)—C(5)—H(5A) | 109.5 |
| C(28)—H(28) | .9500 | N(1)—C(5)—H(5B) | 109.5 |
| C(29)—C(30) | 1.533(2) | H(5A)—C(5)—H(5B) | 109.5 |
| C(29)—H(29A) | .9900 | N(1)—C(5)—H(5C) | 109.5 |
| C(29)—H(29B) | .9900 | H(5A)—C(5)—H(5C) | 109.5 |
| C(30)—H(30A) | .9900 | H(5B)—C(5)—H(5C) | 109.5 |
| C(30)—H(30B) | .9900 | N(1)—C(6)—H(6A) | 109.5 |
| C(31)—C(32) | 1.389(2) | N(1)—C(6)—H(6B) | 109.5 |
| C(31)—H(31) | .9500 | H(6A)—C(6)—H(6B) | 109.5 |
| C(32)—C(33) | 1.388(2) | N(1)—C(6)—H(6C) | 109.5 |
| C(32)—H(32) | .9500 | H(6A)—C(6)—H(6C) | 109.5 |
| C(33)—H(33) | .9500 | H(6B)—C(6)—H(6C) | 109.5 |
| | | C(8)—C(7)—C(4) | 114.44(12) |
| C(6)—N(1)—C(5) | 107.70(12) | C(8)—C(7)—H(7A) | 108.7 |
| C(6)—N(1)—C(4) | 114.92(11) | C(4)—C(7)—H(7A) | 108.7 |
| C(5)—N(1)—C(4) | 113.68(12) | C(8)—C(7)—H(7B) | 108.7 |
| C(10)—N(2)—C(19) | 117.99(11) | C(4)—C(7)—H(7B) | 108.7 |
| C(10)—N(2)—C(9) | 121.96(11) | H(7A)—C(7)—H(7B) | 107.6 |
| C(19)—N(2)—C(9) | 112.14(11) | C(7)—C(8)—C(9) | 112.98(12) |
| C(23)—N(3)—C(22) | 108.75(12) | C(7)—C(8)—H(8A) | 109.0 |
| C(23)—N(3)—H(3N) | 120.3 | C(9)—C(8)—H(8A) | 109.0 |
| C(22)—N(3)—H(3N) | 130.5 | C(7)—C(8)—H(8B) | 109.0 |
| F(1)—C(1)—C(33) | 118.92(14) | C(9)—C(8)—H(8B) | 109.0 |
| F(1)—C(1)—C(2) | 117.24(14) | H(8A)—C(8)—H(8B) | 107.8 |
| C(33)—C(1)—C(2) | 123.80(14) | C(22)—C(9)—N(2) | 105.22(11) |
| C(1)—C(2)—C(3) | 119.46(14) | C(22)—C(9)—C(29) | 112.91(12) |
| C(1)—C(2)—H(2) | 120.3 | N(2)—C(9)—C(29) | 115.53(11) |
| C(3)—C(2)—H(2) | 120.3 | C(22)—C(9)—C(8) | 109.16(11) |
| C(2)—C(3)—C(31) | 117.55(13) | N(2)—C(9)—C(8) | 109.87(11) |
| C(2)—C(3)—C(4) | 121.08(13) | C(29)—C(9)—C(8) | 104.10(11) |
| C(31)—C(3)—C(4) | 121.32(13) | O(1)—C(10)—N(2) | 123.67(13) |
| N(1)—C(4)—C(7) | 106.48(11) | O(1)—C(10)—C(11) | 118.88(13) |
| N(2)—C(10)—C(11) | 117.37(12) | C(22)—C(21)—C(24) | 106.88(13) |
| C(12)—C(11)—C(10) | 118.96(13) | C(22)—C(21)—C(20) | 122.57(14) |
| C(12)—C(11)—H(11) | 120.5 | C(24)—C(21)—C(20) | 130.55(13) |
| C(10)—C(11)—H(11) | 120.5 | C(21)—C(22)—N(3) | 109.70(13) |
| C(11)—C(12)—C(13) | 126.15(14) | C(21)—C(22)—C(9) | 125.74(13) |
| C(11)—C(12)—H(12) | 116.9 | N(3)—C(22)—C(9) | 124.51(12) |
| C(13)—C(12)—H(12) | 116.9 | N(3)—C(23)—C(28) | 130.03(13) |
| C(14)—C(13)—C(18) | 118.60(14) | N(3)—C(23)—C(24) | 107.51(13) |
| C(14)—C(13)—C(12) | 118.72(14) | C(28)—C(23)—C(24) | 122.45(14) |
| C(18)—C(13)—C(12) | 122.58(13) | C(25)—C(24)—C(23) | 118.81(14) |
| C(15)—C(14)—C(13) | 120.71(16) | C(25)—C(24)—C(21) | 134.01(14) |
| C(15)—C(14)—H(14) | 119.6 | C(23)—C(24)—C(21) | 107.16(13) |
| C(13)—C(14)—H(14) | 119.6 | C(26)—C(25)—C(24) | 118.90(14) |
| C(16)—C(15)—C(14) | 120.09(16) | C(26)—C(25)—H(25) | 120.5 |
| C(16)—C(15)—H(15) | 120.0 | C(24)—C(25)—H(25) | 120.5 |

TABLE 29-continued

Bond lengths [A] and angles [deg]

| | | | |
|---|---|---|---|
| C(14)—C(15)—H(15) | 120.0 | C(25)—C(26)—C(27) | 121.20(14) |
| C(17)—C(16)—C(15) | 119.86(16) | C(25)—C(26)—H(26) | 119.4 |
| C(17)—C(16)—H(16) | 120.1 | C(27)—C(26)—H(26) | 119.4 |
| C(15)—C(16)—H(16) | 120.1 | C(28)—C(27)—C(26) | 121.30(15) |
| C(18)—C(17)—C(16) | 120.27(16) | C(28)—C(27)—H(27) | 119.4 |
| C(18)—C(17)—H(17) | 119.9 | C(26)—C(27)—H(27) | 119.4 |
| C(16)—C(17)—H(17) | 119.9 | C(27)—C(28)—C(23) | 117.31(14) |
| C(17)—C(18)—C(13) | 120.45(15) | C(27)—C(28)—H(28) | 121.3 |
| C(17)—C(18)—H(18) | 119.8 | C(23)—C(28)—H(28) | 121.3 |
| C(13)—C(18)—H(18) | 119.8 | C(30)—C(29)—C(9) | 113.19(11) |
| N(2)—C(19)—C(20) | 110.87(12) | C(30)—C(29)—H(29A) | 108.9 |
| N(2)—C(19)—H(19A) | 109.5 | C(9)—C(29)—H(29A) | 108.9 |
| C(20)—C(19)—H(19A) | 109.5 | C(30)—C(29)—H(29B) | 108.9 |
| N(2)—C(19)—H(19B) | 109.5 | C(9)—C(29)—H(29B) | 108.9 |
| C(20)—C(19)—H(19B) | 109.5 | H(29A)—C(29)—H(29B) | 107.8 |
| H(19A)—C(19)—H(19B) | 108.1 | C(29)—C(30)—C(4) | 111.40(11) |
| C(21)—C(20)—C(19) | 109.17(12) | C(29)—C(30)—H(30A) | 109.3 |
| C(21)—C(20)—H(20A) | 109.8 | C(4)—C(30)—H(30A) | 109.3 |
| C(19)—C(20)—H(20A) | 109.8 | C(29)—C(30)—H(30B) | 109.3 |
| C(21)—C(20)—H(20B) | 109.8 | C(4)—C(30)—H(30B) | 109.3 |
| C(19)—C(20)—H(20B) | 109.8 | H(30A)—C(30)—H(30B) | 108.0 |
| H(20A)—C(20)—H(20B) | 108.3 | C(32)—C(31)—C(3) | 121.30(14) |
| C(32)—C(31)—H(31) | 119.4 | C(31)—C(32)—H(32) | 119.6 |
| C(3)—C(31)—H(31) | 119.4 | C(1)—C(33)—C(32) | 117.00(14) |
| C(33)—C(32)—C(31) | 120.89(14) | C(1)—C(33)—H(33) | 121.5 |
| C(33)—C(32)—H(32) | 119.6 | C(32)—C(33)—H(33) | 121.5 |

TABLE 30

Hydrogen coordinates (×10^4) and isotropic displacement parameters (^2 × 10^3).

| | x | y | z | U(eq) |
|---|---|---|---|---|
| H(2) | −60 | 926 | 310 | 24 |
| H(5A) | −1181 | 2177 | 421 | 37 |
| H(5B) | −677 | 2090 | −715 | 37 |
| H(5C) | −1115 | 2756 | −457 | 37 |
| H(6A) | −79 | 3279 | 1538 | 35 |
| H(6B) | 1189 | 3037 | 2583 | 35 |
| H(6C) | −15 | 2687 | 2441 | 35 |
| H(7A) | 797 | 1547 | −415 | 22 |
| H(7B) | 1863 | 2036 | −67 | 22 |
| H(8A) | 2589 | 1034 | −111 | 22 |
| H(8B) | 2118 | 810 | 989 | 22 |
| H(11) | 5498 | 2658 | 552 | 21 |
| H(12) | 6640 | 3068 | 3177 | 23 |
| H(14) | 7712 | 4031 | 3572 | 31 |
| H(15) | 8592 | 4846 | 2884 | 40 |
| H(16) | 8456 | 4884 | 695 | 40 |
| H(17) | 7504 | 4084 | −786 | 35 |
| H(18) | 6652 | 3259 | −98 | 27 |
| H(19A) | 4886 | 1892 | −227 | 25 |
| H(19B) | 3896 | 1363 | −487 | 25 |
| H(20A) | 5657 | 824 | 9 | 28 |
| H(20B) | 6391 | 1277 | 1221 | 28 |
| H(25) | 7177 | −180 | 1636 | 27 |
| H(26) | 7737 | −1078 | 2921 | 31 |
| H(27) | 6734 | −1389 | 4247 | 29 |
| H(28) | 5164 | −794 | 4365 | 26 |
| H(29A) | 2973 | 1228 | 3242 | 20 |
| H(29B) | 4085 | 1695 | 3709 | 20 |
| H(30A) | 2832 | 2467 | 2239 | 21 |
| H(30B) | 2352 | 2270 | 3351 | 21 |
| H(31) | 1030 | 1850 | 3822 | 24 |
| H(32) | 9 | 1144 | 4588 | 27 |
| H(33) | −1043 | 315 | 3236 | 30 |
| H(3N) | 4032 | 297 | 3514 | 39(6) |

TABLE 31

Anisotropic displacement parameters (^2 × 10^3). The anisotropic displacement factor exponent takes the form: −2 pi^2 [h^2 a*^2 U11 + ... + 2 h k a* b* U12]

| | U11 | U22 | U33 | U23 | U13 | U12 |
|---|---|---|---|---|---|---|
| F(1) | 42(1) | 36(1) | 39(1) | −16(1) | 23(1) | −22(1) |
| O(1) | 26(1) | 23(1) | 16(1) | −3(1) | 10(1) | −6(1) |
| N(1) | 22(1) | 19(1) | 18(1) | 1(1) | 7(1) | 0(1) |
| N(2) | 21(1) | 17(1) | 15(1) | −1(1) | 10(1) | −4(1) |
| N(3) | 20(1) | 19(1) | 20(1) | 1(1) | 12(1) | 0(1) |
| C(1) | 22(1) | 21(1) | 28(1) | −6(1) | 11(1) | −5(1) |
| C(2) | 20(1) | 23(1) | 19(1) | −2(1) | 8(1) | −1(1) |
| C(3) | 16(1) | 18(1) | 18(1) | 1(1) | 6(1) | 1(1) |
| C(4) | 19(1) | 17(1) | 15(1) | 0(1) | 7(1) | 0(1) |
| C(5) | 22(1) | 27(1) | 23(1) | 2(1) | 6(1) | 2(1) |
| C(6) | 28(1) | 19(1) | 23(1) | 0(1) | 11(1) | 2(1) |
| C(7) | 20(1) | 21(1) | 14(1) | −1(1) | 7(1) | −2(1) |
| C(8) | 21(1) | 19(1) | 16(1) | −4(1) | 8(1) | −4(1) |
| C(9) | 21(1) | 15(1) | 16(1) | −1(1) | 9(1) | −3(1) |
| C(10) | 17(1) | 15(1) | 15(1) | 0(1) | 6(1) | 0(1) |
| C(11) | 20(1) | 17(1) | 16(1) | 1(1) | 7(1) | −1(1) |
| C(12) | 20(1) | 20(1) | 18(1) | 2(1) | 7(1) | 0(1) |
| C(13) | 16(1) | 18(1) | 24(1) | 2(1) | 6(1) | 0(1) |
| C(14) | 23(1) | 24(1) | 31(1) | −3(1) | 10(1) | −4(1) |
| C(15) | 26(1) | 21(1) | 51(1) | −4(1) | 14(1) | −5(1) |
| C(16) | 26(1) | 24(1) | 51(1) | 11(1) | 17(1) | −3(1) |
| C(17) | 21(1) | 33(1) | 32(1) | 13(1) | 10(1) | 1(1) |
| C(18) | 19(1) | 25(1) | 22(1) | 3(1) | 6(1) | −2(1) |
| C(19) | 30(1) | 22(1) | 16(1) | −4(1) | 13(1) | −7(1) |
| C(20) | 28(1) | 23(1) | 24(1) | −5(1) | 17(1) | −6(1) |
| C(21) | 20(1) | 19(1) | 19(1) | −6(1) | 10(1) | −5(1) |
| C(22) | 20(1) | 17(1) | 18(1) | −2(1) | 9(1) | −4(1) |
| C(23) | 17(1) | 19(1) | 19(1) | −5(1) | 7(1) | −3(1) |
| C(24) | 18(1) | 20(1) | 20(1) | −7(1) | 8(1) | −5(1) |
| C(25) | 19(1) | 25(1) | 25(1) | −10(1) | 10(1) | −4(1) |
| C(26) | 20(1) | 27(1) | 28(1) | −10(1) | 7(1) | 1(1) |
| C(27) | 26(1) | 19(1) | 24(1) | −3(1) | 5(1) | 2(1) |
| C(28) | 22(1) | 21(1) | 21(1) | −3(1) | 8(1) | −2(1) |
| C(29) | 19(1) | 19(1) | 14(1) | −1(1) | 8(1) | −3(1) |
| C(30) | 19(1) | 18(1) | 15(1) | −2(1) | 7(1) | −2(1) |
| C(31) | 21(1) | 22(1) | 17(1) | −1(1) | 7(1) | −1(1) |
| C(32) | 23(1) | 26(1) | 21(1) | 1(1) | 11(1) | −1(1) |
| C(33) | 24(1) | 25(1) | 29(1) | 1(1) | 14(1) | −4(1) |

Example X2

Polymorph A (Measured at High Temperature SCXRD (Single Crystal X-Ray Diffraction)

SCXRD analyses of crystalline forms A was carried out with a Bruker D8-goniometer with SMART APEX CCD area detector at 230 K (±5 K) using MoKα radiation (wavelength of 0.71073 Å, Incoatec microsource, multilayer optics).

TABLE 32

Crystal data and structure refinement

| | |
|---|---|
| Empirical formula | C33H34FN3O |
| Formula weight | 507.63 |
| Temperature | 230(2) K |
| Wavelength | .71073 Å |
| Crystal system | Monoclinic |
| Space group | P 21/c |
| Unit cell dimensions | a = 12.2651(9) Å alpha = 90 deg. |
| | b = 21.6265(16) Å beta = 112.395(2) deg. |
| | c = 10.9590(8) Å gamma = 90 deg. |
| Volume | 2687.6(3) Å$^3$ |
| Z | 4 |
| Density (calculated) | 1.255 Mg/m$^3$ |
| Absorption coefficient | 0.081 mm$^{-1}$ |
| F(000) | 1080 |
| Crystal size | 0.45 × 0.21 × 0.08 mm |
| Theta range for data collection | 1.80 to 28.27 deg. |
| Index ranges | −16 <= h <= 15, −27 <= k <= 28, −14 <= l <= 14 |
| Reflections collected | 31943 |
| Independent reflections | 6654 [R(int) = 0.1802] |
| Absorption correction | None |
| Refinement method | Full-matrix least-squares on F$^2$ |
| Data/restraints/parameters | 6654/0/346 |
| Goodness-of-fit on F$^2$ | 0.946 |
| Final R indices [I > 2sigma(I)] | R1 = 0.0625, wR2 = 0.1445 |
| R indices (all data) | R1 = 0.1004, wR2 = 0.1600 |
| Largest diff. peak and hole | 0.323 and −0.319 e·Å$^{-3}$ |

TABLE 33

Atomic coordinates (×10$^4$) and equivalent isotropic displacement parameters (Å$^2$ × 10$^3$). U(eq) is defined as one third of the trace of the orthogonalized Uij tensor.

| | x | y | z | U(eq) |
|---|---|---|---|---|
| F(1) | −1154(1) | 73(1) | 906(1) | 80(1) |
| O(1) | 5140(1) | 2339(1) | 3240(1) | 46(1) |
| N(1) | 523(1) | 2490(1) | 956(1) | 44(1) |
| N(2) | 4294(1) | 1814(1) | 1283(1) | 36(1) |
| N(3) | 4436(1) | 321(1) | 3004(1) | 39(1) |
| C(1) | −587(2) | 552(1) | 1706(2) | 49(1) |
| C(2) | 4(2) | 961(1) | 1214(2) | 44(1) |
| C(3) | 631(2) | 1448(1) | 1996(2) | 37(1) |
| C(4) | 1271(2) | 1926(1) | 1468(2) | 38(1) |
| C(5) | −666(2) | 2354(1) | −17(2) | 57(1) |
| C(6) | 404(2) | 2894(1) | 1960(2) | 54(1) |
| C(7) | 1583(2) | 1676(1) | 328(2) | 40(1) |
| C(8) | 2481(2) | 1157(1) | 705(2) | 39(1) |
| C(9) | 3674(2) | 1343(1) | 1810(2) | 35(1) |
| C(10) | 5019(2) | 2259(1) | 2092(2) | 34(1) |
| C(11) | 5639(2) | 2682(1) | 1497(2) | 37(1) |
| C(12) | 6430(2) | 3075(1) | 2249(2) | 40(1) |
| C(13) | 7046(2) | 3554(1) | 1808(2) | 41(1) |
| C(14) | 7639(2) | 4016(1) | 2688(2) | 54(1) |
| C(15) | 8160(2) | 4500(1) | 2280(3) | 69(1) |
| C(16) | 8091(2) | 4533(1) | 1016(3) | 73(1) |
| C(17) | 7520(2) | 4072(1) | 132(2) | 64(1) |
| C(18) | 7009(2) | 3583(1) | 532(2) | 50(1) |
| C(19) | 4608(2) | 1562(1) | 205(2) | 45(1) |
| C(20) | 5583(2) | 1082(1) | 734(2) | 49(1) |
| C(21) | 5331(2) | 661(1) | 1678(2) | 40(1) |
| C(22) | 4476(2) | 790(1) | 2163(2) | 37(1) |
| C(23) | 5283(2) | −116(1) | 3077(2) | 39(1) |
| C(24) | 5850(2) | 88(1) | 2250(2) | 40(1) |
| C(25) | 6770(2) | −276(1) | 2165(2) | 48(1) |
| C(26) | 7086(2) | −810(1) | 2904(2) | 55(1) |
| C(27) | 6504(2) | −1002(1) | 3707(2) | 54(1) |
| C(28) | 5592(2) | −658(1) | 3807(2) | 46(1) |
| C(29) | 3323(2) | 1567(1) | 2941(2) | 37(1) |
| C(30) | 2460(2) | 2108(1) | 2552(2) | 38(1) |
| C(31) | 614(2) | 1497(1) | 3259(2) | 43(1) |
| C(32) | 6(2) | 1079(1) | 3721(2) | 50(1) |
| C(33) | −606(2) | 594(1) | 2931(2) | 54(1) |

TABLE 34

Bond lengths [Å] and angles [deg].

| | | | |
|---|---|---|---|
| F(1)—C(1) | 1.365(2) | C(3)—C(4) | 1.537(3) |
| O(1)—C(10) | 1.2214(18) | C(4)—C(7) | 1.537(2) |
| N(1)—C(6) | 1.455(2) | C(4)—C(30) | 1.540(2) |
| N(1)—C(5) | 1.472(2) | C(5)—H(5A) | .9700 |
| N(1)—C(4) | 1.502(2) | C(5)—H(5B) | .9700 |
| N(2)—C(10) | 1.379(2) | C(5)—H(5C) | .9700 |
| N(2)—C(19) | 1.479(2) | C(6)—H(6A) | .9700 |
| N(2)—C(9) | 1.512(2) | C(6)—H(6B) | .9700 |
| N(3)—C(22) | 1.383(2) | C(6)—H(6C) | .9700 |
| N(3)—C(23) | 1.385(2) | C(7)—C(8) | 1.515(3) |
| N(3)—H(3N) | .8609 | C(7)—H(7A) | .9800 |
| C(1)—C(33) | 1.355(3) | C(7)—H(7B) | .9800 |
| C(1)—C(2) | 1.377(3) | C(8)—C(9) | 1.556(2) |
| C(2)—C(3) | 1.391(3) | C(8)—H(8A) | .9800 |
| C(2)—H(2) | .9400 | C(8)—H(8B) | .9800 |
| C(3)—C(31) | 1.396(2) | C(9)—C(22) | 1.502(3) |
| C(9)—C(29) | 1.538(2) | C(29)—H(29B) | .9800 |
| C(10)—C(11) | 1.490(2) | C(30)—H(30A) | .9800 |
| C(11)—C(12) | 1.316(2) | C(30)—H(30B) | .9800 |
| C(11)—H(11) | .9400 | C(31)—C(32) | 1.384(3) |
| C(12)—C(13) | 1.469(3) | C(31)—H(31) | .9400 |
| C(12)—H(12) | .9400 | C(32)—C(33) | 1.385(3) |
| C(13)—C(18) | 1.383(3) | C(32)—H(32) | .9400 |
| C(13)—C(14) | 1.387(3) | C(33)—H(33) | .9400 |
| C(14)—C(15) | 1.387(3) | | |
| C(14)—H(14) | .9400 | C(6)—N(1)—C(5) | 108.11(16) |
| C(15)—C(16) | 1.357(3) | C(6)—N(1)—C(4) | 115.41(14) |
| C(15)—H(15) | .9400 | C(5)—N(1)—C(4) | 113.77(16) |

TABLE 34-continued

Bond lengths [A] and angles [deg].

| | | | |
|---|---|---|---|
| C(16)—C(17) | 1.381(3) | C(10)—N(2)—C(19) | 118.05(15) |
| C(16)—H(16) | .9400 | C(10)—N(2)—C(9) | 121.32(13) |
| C(17)—C(18) | 1.383(3) | C(19)—N(2)—C(9) | 112.20(14) |
| C(17)—H(17) | .9400 | C(22)—N(3)—C(23) | 108.89(15) |
| C(18)—H(18) | .9400 | C(22)—N(3)—H(3N) | 132.3 |
| C(19)—C(20) | 1.521(3) | C(23)—N(3)—H(3N) | 118.4 |
| C(19)—H(19A) | .9800 | C(33)—C(1)—F(1) | 119.36(19) |
| C(19)—H(19B) | .9800 | C(33)—C(1)—C(2) | 123.77(19) |
| C(20)—C(21) | 1.497(3) | F(1)—C(1)—C(2) | 116.85(17) |
| C(20)—H(20A) | .9800 | C(1)—C(2)—C(3) | 119.68(18) |
| C(20)—H(20B) | .9800 | C(1)—C(2)—H(2) | 120.2 |
| C(21)—C(22) | 1.372(2) | C(3)—C(2)—H(2) | 120.2 |
| C(21)—C(24) | 1.425(3) | C(2)—C(3)—C(31) | 117.03(17) |
| C(23)—C(28) | 1.387(3) | C(2)—C(3)—C(4) | 121.23(16) |
| C(23)—C(24) | 1.408(3) | C(31)—C(3)—C(4) | 121.69(16) |
| C(24)—C(25) | 1.406(3) | N(1)—C(4)—C(7) | 106.69(14) |
| C(25)—C(26) | 1.378(3) | N(1)—C(4)—C(3) | 111.08(15) |
| C(25)—H(25) | .9400 | C(7)—C(4)—C(3) | 113.06(15) |
| C(26)—C(27) | 1.392(3) | N(1)—C(4)—C(30) | 110.08(15) |
| C(26)—H(26) | .9400 | C(7)—C(4)—C(30) | 105.17(15) |
| C(27)—C(28) | 1.383(3) | C(3)—C(4)—C(30) | 110.54(14) |
| C(27)—H(27) | .9400 | N(1)—C(5)—H(5A) | 109.5 |
| C(28)—H(28) | .9400 | N(1)—C(5)—H(5B) | 109.5 |
| C(29)—C(30) | 1.527(3) | H(5A)—C(5)—H(5B) | 109.5 |
| C(29)—H(29A) | .9800 | N(1)—C(5)—H(5C) | 109.5 |
| H(5A)—C(5)—H(5C) | 109.5 | C(14)—C(13)—C(12) | 118.64(18) |
| H(5B)—C(5)—H(5C) | 109.5 | C(15)—C(14)—C(13) | 120.3(2) |
| N(1)—C(6)—H(6A) | 109.5 | C(15)—C(14)—H(14) | 119.9 |
| N(1)—C(6)—H(6B) | 109.5 | C(13)—C(14)—H(14) | 119.9 |
| H(6A)—C(6)—H(6B) | 109.5 | C(16)—C(15)—C(14) | 120.7(2) |
| N(1)—C(6)—H(6C) | 109.5 | C(16)—C(15)—H(15) | 119.6 |
| H(6A)—C(6)—H(6C) | 109.5 | C(14)—C(15)—H(15) | 119.6 |
| H(6B)—C(6)—H(6C) | 109.5 | C(15)—C(16)—C(17) | 119.8(2) |
| C(8)—C(7)—C(4) | 114.70(15) | C(15)—C(16)—H(16) | 120.1 |
| C(8)—C(7)—H(7A) | 108.6 | C(17)—C(16)—H(16) | 120.1 |
| C(4)—C(7)—H(7A) | 108.6 | C(16)—C(17)—C(18) | 119.9(2) |
| C(8)—C(7)—H(7B) | 108.6 | C(16)—C(17)—H(17) | 120.0 |
| C(4)—C(7)—H(7B) | 108.6 | C(18)—C(17)—H(17) | 120.0 |
| H(7A)—C(7)—H(7B) | 107.6 | C(17)—C(18)—C(13) | 120.8(2) |
| C(7)—C(8)—C(9) | 113.05(15) | C(17)—C(18)—H(18) | 119.6 |
| C(7)—C(8)—H(8A) | 109.0 | C(13)—C(18)—H(18) | 119.6 |
| C(9)—C(8)—H(8A) | 109.0 | N(2)—C(19)—C(20) | 110.73(15) |
| C(7)—C(8)—H(8B) | 109.0 | N(2)—C(19)—H(19A) | 109.5 |
| C(9)—C(8)—H(8B) | 109.0 | C(20)—C(19)—H(19A) | 109.5 |
| H(8A)—C(8)—H(8B) | 107.8 | N(2)—C(19)—H(19B) | 109.5 |
| C(22)—C(9)—N(2) | 105.07(14) | C(20)—C(19)—H(19B) | 109.5 |
| C(22)—C(9)—C(29) | 113.57(14) | H(19A)—C(19)—H(19B) | 108.1 |
| N(2)—C(9)—C(29) | 115.57(14) | C(21)—C(20)—C(19) | 109.80(16) |
| C(22)—C(9)—C(8) | 108.97(15) | C(21)—C(20)—H(20A) | 109.7 |
| N(2)—C(9)—C(8) | 109.74(13) | C(19)—C(20)—H(20A) | 109.7 |
| C(29)—C(9)—C(8) | 103.86(14) | C(21)—C(20)—H(20B) | 109.7 |
| O(1)—C(10)—N(2) | 123.79(16) | C(19)—C(20)—H(20B) | 109.7 |
| O(1)—C(10)—C(11) | 118.84(16) | H(20A)—C(20)—H(20B) | 108.2 |
| N(2)—C(10)—C(11) | 117.30(14) | C(22)—C(21)—C(24) | 106.63(16) |
| C(12)—C(11)—C(10) | 120.00(16) | C(22)—C(21)—C(20) | 122.25(19) |
| C(12)—C(11)—H(11) | 120.0 | C(24)—C(21)—C(20) | 131.12(17) |
| C(10)—C(11)—H(11) | 120.0 | C(21)—C(22)—N(3) | 109.58(17) |
| C(11)—C(12)—C(13) | 126.77(17) | C(21)—C(22)—C(9) | 125.71(17) |
| C(11)—C(12)—H(12) | 116.6 | N(3)—C(22)—C(9) | 124.67(16) |
| C(13)—C(12)—H(12) | 116.6 | N(3)—C(23)—C(28) | 130.15(17) |
| C(18)—C(13)—C(14) | 118.47(19) | N(3)—C(23)—C(24) | 106.96(17) |
| C(18)—C(13)—C(12) | 122.80(17) | C(28)—C(23)—C(24) | 122.88(18) |
| C(25)—C(24)—C(23) | 118.18(19) | C(9)—C(29)—H(29B) | 108.9 |
| C(25)—C(24)—C(21) | 133.87(18) | H(29A)—C(29)—H(29B) | 107.8 |
| C(23)—C(24)—C(21) | 107.94(16) | C(29)—C(30)—C(4) | 111.75(15) |
| C(26)—C(25)—C(24) | 118.92(19) | C(29)—C(30)—H(30A) | 109.3 |
| C(26)—C(25)—H(25) | 120.5 | C(4)—C(30)—H(30A) | 109.3 |
| C(24)—C(25)—H(25) | 120.5 | C(29)—C(30)—H(30B) | 109.3 |
| C(25)—C(26)—C(27) | 121.6(2) | C(4)—C(30)—H(30B) | 109.3 |
| C(25)—C(26)—H(26) | 119.2 | H(30A)—C(30)—H(30B) | 107.9 |
| C(27)—C(26)—H(26) | 119.2 | C(32)—C(31)—C(3) | 121.78(18) |
| C(28)—C(27)—C(26) | 120.9(2) | | |
| C(28)—C(27)—H(27) | 119.5 | C(32)—C(31)—H(31) | 119.1 |
| C(26)—C(27)—H(27) | 119.5 | C(3)—C(31)—H(31) | 119.1 |
| C(27)—C(28)—C(23) | 117.43(19) | C(31)—C(32)—C(33) | 120.36(19) |
| C(27)—C(28)—H(28) | 121.3 | | |
| C(23)—C(28)—H(28) | 121.3 | C(31)—C(32)—H(32) | 119.8 |
| C(30)—C(29)—C(9) | 113.18(14) | C(33)—C(32)—H(32) | 119.8 |

TABLE 34-continued

Bond lengths [A] and angles [deg].

| | | | |
|---|---|---|---|
| C(30)—C(29)—H(29A) | 108.9 | C(1)—C(33)—C(32) | 117.4(2) |
| C(9)—C(29)—H(29A) | 108.9 | C(1)—C(33)—H(33) | 121.3 |
| C(30)—C(29)—H(29B) | 108.9 | C(32)—C(33)—H(33) | 121.3 |

TABLE 35

Hydrogen coordinates (×10^4) and isotropic displacement parameters (Å^2 × 10^3) for ansolvat_ht.

| | x | y | z | U(eq) |
|---|---|---|---|---|
| H(2) | −15 | 910 | 354 | 52 |
| H(5A) | −1135 | 2167 | 427 | 85 |
| H(5B) | −609 | 2069 | −675 | 85 |
| H(5C) | −1038 | 2734 | −443 | 85 |
| H(6A) | −22 | 3265 | 1545 | 81 |
| H(6B) | 1181 | 3007 | 2588 | 81 |
| H(6C) | −25 | 2681 | 2416 | 81 |
| H(7A) | 859 | 1528 | −372 | 49 |
| H(7B) | 1889 | 2018 | −36 | 49 |
| H(8A) | 2624 | 1029 | −79 | 47 |
| H(8B) | 2154 | 802 | 1005 | 47 |
| H(11) | 5465 | 2669 | 585 | 45 |
| H(12) | 6620 | 3046 | 3163 | 49 |
| H(14) | 7687 | 4001 | 3564 | 65 |
| H(15) | 8565 | 4810 | 2886 | 82 |
| H(16) | 8432 | 4868 | 744 | 88 |
| H(17) | 7480 | 4090 | −742 | 77 |
| H(18) | 6631 | 3267 | −70 | 60 |
| H(19A) | 4872 | 1899 | −215 | 54 |
| H(19B) | 3911 | 1372 | −464 | 54 |
| H(20A) | 5633 | 841 | 0 | 59 |
| H(20B) | 6341 | 1290 | 1184 | 59 |
| H(25) | 7161 | −157 | 1614 | 58 |
| H(26) | 7711 | −1050 | 2864 | 66 |
| H(27) | 6735 | −1372 | 4188 | 65 |
| H(28) | 5196 | −786 | 4349 | 56 |
| H(29A) | 2964 | 1222 | 3235 | 44 |
| H(29B) | 4036 | 1692 | 3687 | 44 |
| H(30A) | 2806 | 2450 | 2234 | 45 |
| H(30B) | 2326 | 2253 | 3331 | 45 |
| H(31) | 1027 | 1822 | 3811 | 52 |
| H(32) | 8 | 1125 | 4574 | 60 |
| H(33) | −1017 | 304 | 3234 | 64 |
| H(3N) | 4057 | 282 | 3518 | 72(7) |

TABLE 36

Anisotropic displacement parameters (Å^2 × 10^3).
The anisotropic displacement factor exponent takes the form:
$-2\pi^2 [h^2 a^{*2} U11 + \ldots + 2 h k a^* b^* U12]$

| | U11 | U22 | U33 | U23 | U13 | U12 |
|---|---|---|---|---|---|---|
| F(1) | 80(1) | 78(1) | 96(1) | −37(1) | 50(1) | −45(1) |
| O(1) | 51(1) | 53(1) | 37(1) | −8(1) | 20(1) | −15(1) |
| N(1) | 42(1) | 43(1) | 43(1) | 1(1) | 12(1) | 3(1) |
| N(2) | 42(1) | 37(1) | 34(1) | −5(1) | 17(1) | −11(1) |
| N(3) | 38(1) | 39(1) | 49(1) | 1(1) | 25(1) | −3(1) |
| C(1) | 42(1) | 47(1) | 62(1) | −13(1) | 23(1) | −13(1) |
| C(2) | 38(1) | 49(1) | 47(1) | −4(1) | 19(1) | −5(1) |
| C(3) | 32(1) | 37(1) | 40(1) | −1(1) | 12(1) | 1(1) |
| C(4) | 38(1) | 37(1) | 38(1) | 0(1) | 14(1) | −2(1) |
| C(5) | 42(1) | 60(2) | 60(1) | 5(1) | 10(1) | 5(1) |
| C(6) | 60(1) | 44(1) | 59(1) | 3(1) | 24(1) | 9(1) |
| C(7) | 39(1) | 45(1) | 36(1) | −1(1) | 13(1) | −6(1) |
| C(8) | 40(1) | 40(1) | 39(1) | −6(1) | 17(1) | −9(1) |
| C(9) | 37(1) | 34(1) | 36(1) | −3(1) | 17(1) | −9(1) |
| C(10) | 34(1) | 35(1) | 32(1) | −1(1) | 11(1) | −1(1) |
| C(11) | 37(1) | 40(1) | 34(1) | 2(1) | 12(1) | −3(1) |
| C(12) | 38(1) | 42(1) | 40(1) | 1(1) | 13(1) | −6(1) |
| C(13) | 31(1) | 39(1) | 48(1) | 4(1) | 10(1) | −1(1) |
| C(14) | 45(1) | 49(1) | 68(1) | −6(1) | 20(1) | −11(1) |
| C(15) | 54(1) | 46(2) | 106(2) | −7(1) | 30(1) | −15(1) |
| C(16) | 54(2) | 52(2) | 113(2) | 26(1) | 33(2) | −8(1) |
| C(17) | 45(1) | 72(2) | 75(2) | 30(1) | 22(1) | −3(1) |
| C(18) | 36(1) | 57(1) | 52(1) | 9(1) | 12(1) | −8(1) |
| C(19) | 60(1) | 44(1) | 37(1) | −9(1) | 26(1) | −18(1) |
| C(20) | 57(1) | 47(1) | 55(1) | −11(1) | 35(1) | −13(1) |
| C(21) | 41(1) | 42(1) | 45(1) | −12(1) | 24(1) | −11(1) |
| C(22) | 35(1) | 38(1) | 40(1) | −3(1) | 18(1) | −8(1) |
| C(23) | 33(1) | 39(1) | 45(1) | −7(1) | 15(1) | −5(1) |
| C(24) | 33(1) | 43(1) | 45(1) | −13(1) | 17(1) | −9(1) |
| C(25) | 37(1) | 53(1) | 58(1) | −20(1) | 24(1) | −9(1) |
| C(26) | 38(1) | 60(2) | 64(1) | −20(1) | 15(1) | 5(1) |
| C(27) | 48(1) | 48(1) | 60(1) | −4(1) | 12(1) | 5(1) |
| C(28) | 42(1) | 45(1) | 51(1) | −2(1) | 17(1) | −2(1) |
| C(29) | 38(1) | 38(1) | 36(1) | −2(1) | 16(1) | −7(1) |
| C(30) | 38(1) | 37(1) | 38(1) | −3(1) | 15(1) | −5(1) |
| C(31) | 39(1) | 46(1) | 45(1) | −4(1) | 16(1) | −6(1) |
| C(32) | 46(1) | 59(2) | 49(1) | 0(1) | 24(1) | −6(1) |
| C(33) | 47(1) | 55(1) | 67(1) | −2(1) | 31(1) | −12(1) |

Polymorph B

SCXRD (Single Crystal X-Ray Diffraction)

SCXRD analyses of crystalline forms A was carried out with a Bruker D8-goniometer with SMART APEX CCD area detector at 100 K (±5 K) using MoKα radiation (wavelength of 0.71073 Å, Incoatec microsource, multilayer optics).

TABLE 37

Crystal data and structure refinement

| | |
|---|---|
| Identification code | GM391-063-P1A1 |
| Empirical formula | C33H40FN3O4 |
| Formula weight | 561.68 |
| Temperature | 100(2) K |
| Wavelength | .71073 Å |
| Crystal system | Orthorhombic |
| Space group | P b c a |
| Unit cell dimensions | a = 9.6937(12) Å alpha = 90 deg. |
| | b = 25.858(3) Å beta = 90 deg. |
| | c = 23.491(3) Å gamma = 90 deg. |
| Volume | 5888.2(13) Å^3 |
| Z | 8 |
| Density (calculated) | 1.267 Mg/m^3 |
| Absorption coefficient | 0.088 mm^−1 |
| F(000) | 2400 |
| Crystal size | 0.31 × 0.08 × 0.02 mm |
| Theta range for data collection | 1.73 to 17.30 deg. |
| Index ranges | −8 <= h <= 8, −21 <= k <= 21, |
| | −19 <= l <= 19 |
| Reflections collected | 17449 |
| Independent reflections | 1797 [R(int) = 0.0904] |
| Absorption correction | None |
| Refinement method | Full-matrix least-squares on F^2 |
| Data/restraints/parameters | 1797/48/172 |
| Goodness-of-fit on F^2 | 1.200 |
| Final R indices [I > 2sigma(I)] | R1 = 0.1515, wR2 = 0.3024 |
| R indices (all data) | R1 = 0.1580, wR2 = 0.3055 |
| Largest diff. peak and hole | .840 and −.560 e · Å^−3 |

TABLE 38

Atomic coordinates (×10^4) and equivalent isotropic displacement parameters (Å^2 × 10^3). U(eq) is defined as one third of the trace of the orthogonalized Uij tensor.

| | x | y | z | U(eq) |
|---|---|---|---|---|
| F(1) | 3998(14) | 561(5) | −65(6) | 103(4) |
| O(1) | 3137(11) | 3318(4) | 1280(4) | 25(3) |
| N(1) | 5513(13) | 1742(5) | 1773(5) | 28(3) |
| N(2) | 5488(14) | 3380(5) | 1096(5) | 27(3) |
| N(3) | 5620(13) | 3217(5) | −476(5) | 28(3) |
| C(1) | 5090(2) | 866(8) | 147(9) | 68(4) |
| C(2) | 4810(2) | 1264(7) | 499(8) | 54(4) |
| C(3) | 5880(19) | 1543(7) | 733(7) | 39(3) |
| C(4) | 5623(17) | 1971(6) | 1163(7) | 29(3) |
| C(5) | 4444(16) | 1347(6) | 1830(7) | 30(4) |
| C(6) | 6828(17) | 1541(6) | 2007(7) | 36(5) |
| C(7) | 4322(17) | 2265(6) | 1046(7) | 29(3) |
| C(8) | 4417(17) | 2636(6) | 550(7) | 28(3) |
| C(9) | 5599(17) | 3021(6) | 599(7) | 26(3) |
| C(10) | 4323(18) | 3484(6) | 1405(7) | 29(3) |
| C(11) | 4500(18) | 3800(6) | 1921(7) | 28(3) |
| C(12) | 3543(17) | 4105(6) | 2110(7) | 27(3) |
| C(13) | 3517(18) | 4420(6) | 2622(7) | 31(3) |
| C(14) | 4506(18) | 4318(7) | 3040(7) | 37(3) |
| C(15) | 4484(19) | 4648(7) | 3532(7) | 44(4) |
| C(16) | 3521(19) | 5025(7) | 3594(8) | 44(4) |
| C(17) | 2600(2) | 5106(7) | 3188(7) | 40(4) |
| C(18) | 2531(19) | 4802(6) | 2696(7) | 34(4) |
| C(19) | 6546(17) | 3776(6) | 1108(7) | 26(3) |
| C(20) | 6241(17) | 4176(6) | 659(6) | 27(3) |
| C(21) | 5960(17) | 3893(6) | 121(7) | 29(3) |
| C(22) | 5736(17) | 3387(6) | 87(7) | 27(3) |
| C(23) | 5778(17) | 3656(6) | −818(7) | 31(3) |
| C(24) | 6009(17) | 4080(6) | −469(7) | 30(3) |
| C(25) | 6149(16) | 4570(6) | −706(7) | 31(3) |
| C(26) | 6076(17) | 4623(7) | −1292(7) | 33(4) |
| C(27) | 5877(17) | 4196(6) | −1621(7) | 33(4) |
| C(28) | 5684(17) | 3697(6) | −1418(7) | 33(3) |
| C(29) | 6919(16) | 2703(6) | 667(7) | 28(3) |
| C(30) | 6855(16) | 2354(6) | 1191(7) | 28(3) |
| C(31) | 7205(19) | 1368(7) | 588(7) | 41(4) |
| C(32) | 7420(2) | 976(7) | 206(8) | 49(4) |
| C(33) | 6380(2) | 709(8) | −33(8) | 58(4) |
| O(2) | 526(12) | 2738(4) | 1134(5) | 47(4) |
| O(3) | 4823(11) | 2458(4) | 2660(4) | 34(3) |
| O(4) | 2311(11) | 2973(4) | 2428(4) | 37(3) |

TABLE 39

Bond lengths [Å] and angles [deg]

| | | | |
|---|---|---|---|
| F(1)—C(1) | 1.41(2) | C(11)—C(12) | 1.296(19) |
| O(1)—C(10) | 1.261(17) | C(11)—H(11) | .9500 |
| N(1)—C(5) | 1.461(18) | C(12)—C(13) | 1.45(2) |
| N(1)—C(6) | 1.484(19) | C(12)—H(12) | .9500 |
| N(1)—C(4) | 1.55(2) | C(13)—C(18) | 1.38(2) |
| N(2)—C(10) | 1.369(19) | C(13)—C(14) | 1.40(2) |
| N(2)—C(19) | 1.448(18) | C(14)—C(15) | 1.44(2) |
| N(2)—C(9) | 1.495(19) | C(14)—H(14) | .9500 |
| N(3)—C(22) | 1.397(18) | C(15)—C(16) | 1.36(2) |
| N(3)—C(23) | 1.399(19) | C(15)—H(15) | .9500 |
| N(3)—H(3) | .9200 | C(16)—C(17) | 1.32(2) |
| C(1)—C(2) | 1.35(2) | C(16)—H(16) | .9500 |
| C(1)—C(33) | 1.38(3) | C(17)—C(18) | 1.40(2) |
| C(2)—C(3) | 1.38(2) | C(17)—H(17) | .9500 |
| C(2)—H(2) | .9500 | C(18)—H(18) | .9500 |
| C(3)—C(31) | 1.40(2) | C(19)—C(20) | 1.51(2) |
| C(3)—C(4) | 1.52(2) | C(19)—H(19A) | .9900 |
| C(4)—C(7) | 1.50(2) | C(19)—H(19B) | .9900 |
| C(4)—C(30) | 1.55(2) | C(20)—C(21) | 1.48(2) |
| C(5)—H(5A) | .9800 | C(20)—H(20A) | .9900 |
| C(5)—H(5B) | .9800 | C(20)—H(20B) | .9900 |
| C(5)—H(5C) | .9800 | C(21)—C(22) | 1.328(19) |
| C(6)—H(6A) | .9800 | C(21)—C(24) | 1.47(2) |
| C(6)—H(6B) | .9800 | C(23)—C(24) | 1.39(2) |
| C(6)—H(6C) | .9800 | C(23)—C(28) | 1.42(2) |
| C(7)—C(8) | 1.51(2) | C(24)—C(25) | 1.39(2) |
| C(7)—H(7A) | .9900 | C(25)—C(26) | 1.39(2) |
| C(7)—H(7B) | .9900 | C(25)—H(25) | .9500 |
| C(8)—C(9) | 1.52(2) | C(26)—C(27) | 1.36(2) |
| C(8)—H(8A) | .9900 | C(26)—H(26) | .9500 |
| C(8)—H(8B) | .9900 | C(27)—C(28) | 1.39(2) |
| C(9)—C(29) | 1.53(2) | C(27)—H(27) | .9500 |
| C(9)—C(22) | 1.54(2) | C(28)—H(28) | .9500 |
| C(10)—C(11) | 1.47(2) | C(29)—C(30) | 1.53(2) |
| C(29)—H(29A) | .9900 | C(7)—C(4)—N(1) | 107.7(13) |
| C(29)—H(29B) | .9900 | C(3)—C(4)—N(1) | 110.3(12) |
| C(30)—H(30A) | .9900 | C(30)—C(4)—N(1) | 104.9(12) |
| C(30)—H(30B) | .9900 | N(1)—C(5)—H(5A) | 109.5 |
| C(31)—C(32) | 1.37(2) | N(1)—C(5)—H(5B) | 109.5 |

TABLE 39-continued

| Bond lengths [A] and angles [deg] | | | |
|---|---|---|---|
| C(31)—H(31) | .9500 | H(5A)—C(5)—H(5B) | 109.5 |
| C(32)—C(33) | 1.35(2) | N(1)—C(5)—H(5C) | 109.5 |
| C(32)—H(32) | .9500 | H(5A)—C(5)—H(5C) | 109.5 |
| C(33)—H(33) | .9500 | H(5B)—C(5)—H(5C) | 109.5 |
| O(2)—H(1W) | .8500 | N(1)—C(6)—H(6A) | 109.5 |
| O(2)—H(2W) | .8499 | N(1)—C(6)—H(6B) | 109.5 |
| O(3)—H(3W) | .8499 | H(6A)—C(6)—H(6B) | 109.5 |
| O(3)—H(4W) | .8500 | N(1)—C(6)—H(6C) | 109.5 |
| O(4)—H(5W) | .8499 | H(6A)—C(6)—H(6C) | 109.5 |
| O(4)—H(6W) | .8502 | H(6B)—C(6)—H(6C) | 109.5 |
| | | C(4)—C(7)—C(8) | 114.3(14) |
| C(5)—N(1)—C(6) | 109.3(12) | C(4)—C(7)—H(7A) | 108.7 |
| C(5)—N(1)—C(4) | 113.5(12) | C(8)—C(7)—H(7A) | 108.7 |
| C(6)—N(1)—C(4) | 114.6(12) | C(4)—C(7)—H(7B) | 108.7 |
| C(10)—N(2)—C(19) | 115.8(13) | C(8)—C(7)—H(7B) | 108.7 |
| C(10)—N(2)—C(9) | 126.5(13) | H(7A)—C(7)—H(7B) | 107.6 |
| C(19)—N(2)—C(9) | 113.7(12) | C(7)—C(8)—C(9) | 113.7(13) |
| C(22)—N(3)—C(23) | 106.3(13) | C(7)—C(8)—H(8A) | 108.8 |
| C(22)—N(3)—H(3) | 123.1 | C(9)—C(8)—H(8A) | 108.8 |
| C(23)—N(3)—H(3) | 128.3 | C(7)—C(8)—H(8B) | 108.8 |
| C(2)—C(1)—C(33) | 126(2) | C(9)—C(8)—H(8B) | 108.8 |
| C(2)—C(1)—F(1) | 120(2) | H(8A)—C(8)—H(8B) | 107.7 |
| C(33)—C(1)—F(1) | 113.9(19) | N(2)—C(9)—C(8) | 114.3(13) |
| C(1)—C(2)—C(3) | 120(2) | N(2)—C(9)—C(29) | 108.3(13) |
| C(1)—C(2)—H(2) | 120.1 | C(8)—C(9)—C(29) | 106.5(12) |
| C(3)—C(2)—H(2) | 120.1 | N(2)—C(9)—C(22) | 103.6(12) |
| C(2)—C(3)—C(31) | 114.9(16) | C(8)—C(9)—C(22) | 114.1(13) |
| C(2)—C(3)—C(4) | 121.7(17) | C(29)—C(9)—C(22) | 109.9(13) |
| C(31)—C(3)—C(4) | 123.2(16) | O(1)—C(10)—N(2) | 124.2(14) |
| C(7)—C(4)—C(3) | 112.8(14) | O(1)—C(10)—C(11) | 119.1(15) |
| C(7)—C(4)—C(30) | 109.3(12) | N(2)—C(10)—C(11) | 116.7(15) |
| C(3)—C(4)—C(30) | 111.5(14) | C(12)—C(11)—C(10) | 122.5(16) |
| C(12)—C(11)—H(11) | 118.7 | C(24)—C(21)—C(20) | 129.4(14) |
| C(10)—C(11)—H(11) | 118.7 | C(21)—C(22)—N(3) | 112.4(14) |
| C(11)—C(12)—C(13) | 129.6(16) | C(21)—C(22)—C(9) | 124.9(15) |
| C(11)—C(12)—H(12) | 115.2 | N(3)—C(22)—C(9) | 122.7(13) |
| C(13)—C(12)—H(12) | 115.2 | C(24)—C(23)—N(3) | 108.6(14) |
| C(18)—C(13)—C(14) | 121.3(15) | C(24)—C(23)—C(28) | 122.8(16) |
| C(18)—C(13)—C(12) | 121.0(15) | N(3)—C(23)—C(28) | 128.7(15) |
| C(14)—C(13)—C(12) | 117.6(15) | C(23)—C(24)—C(25) | 119.9(15) |
| C(13)—C(14)—C(15) | 116.3(16) | C(23)—C(24)—C(21) | 107.0(14) |
| C(13)—C(14)—H(14) | 121.8 | C(25)—C(24)—C(21) | 132.9(15) |
| C(15)—C(14)—H(14) | 121.8 | C(26)—C(25)—C(24) | 118.9(16) |
| C(16)—C(15)—C(14) | 121.6(18) | C(26)—C(25)—H(25) | 120.6 |
| C(16)—C(15)—H(15) | 119.2 | C(24)—C(25)—H(25) | 120.6 |
| C(14)—C(15)—H(15) | 119.2 | C(27)—C(26)—C(25) | 119.4(16) |
| C(17)—C(16)—C(15) | 119.9(19) | C(27)—C(26)—H(26) | 120.3 |
| C(17)—C(16)—H(16) | 120.0 | C(25)—C(26)—H(26) | 120.3 |
| C(15)—C(16)—H(16) | 120.0 | C(26)—C(27)—C(28) | 125.3(16) |
| C(16)—C(17)—C(18) | 122.6(18) | C(26)—C(27)—H(27) | 117.3 |
| C(16)—C(17)—H(17) | 118.7 | C(28)—C(27)—H(27) | 117.3 |
| C(18)—C(17)—H(17) | 118.7 | C(27)—C(28)—C(23) | 113.7(16) |
| C(13)—C(18)—C(17) | 118.1(17) | C(27)—C(28)—H(28) | 123.2 |
| C(13)—C(18)—H(18) | 120.9 | C(23)—C(28)—H(28) | 123.2 |
| C(17)—C(18)—H(18) | 120.9 | C(30)—C(29)—C(9) | 111.6(13) |
| N(2)—C(19)—C(20) | 109.4(13) | C(30)—C(29)—H(29A) | 109.3 |
| N(2)—C(19)—H(19A) | 109.8 | C(9)—C(29)—H(29A) | 109.3 |
| C(20)—C(19)—H(19A) | 109.8 | C(30)—C(29)—H(29B) | 109.3 |
| N(2)—C(19)—H(19B) | 109.8 | C(9)—C(29)—H(29B) | 109.3 |
| C(20)—C(19)—H(19B) | 109.8 | H(29A)—C(29)—H(29B) | 108.0 |
| H(19A)—C(19)—H(19B) | 108.2 | C(29)—C(30)—C(4) | 111.9(13) |
| C(21)—C(20)—C(19) | 107.0(13) | C(29)—C(30)—H(30A) | 109.2 |
| C(21)—C(20)—H(20A) | 110.3 | C(4)—C(30)—H(30A) | 109.2 |
| C(19)—C(20)—H(20A) | 110.3 | C(29)—C(30)—H(30B) | 109.2 |
| C(21)—C(20)—H(20B) | 110.3 | C(4)—C(30)—H(30B) | 109.2 |
| C(19)—C(20)—H(20B) | 110.3 | H(30A)—C(30)—H(30B) | 107.9 |
| H(20A)—C(20)—H(20B) | 108.6 | C(32)—C(31)—C(3) | 122.7(18) |
| C(22)—C(21)—C(24) | 105.8(14) | C(32)—C(31)—H(31) | 118.7 |
| C(22)—C(21)—C(20) | 124.6(15) | C(3)—C(31)—H(31) | 118.7 |
| C(33)—C(32)—C(31) | 122(2) | C(1)—C(33)—H(33) | 123.2 |
| C(33)—C(32)—H(32) | 118.9 | H(1W)—O(2)—H(2W) | 116.5 |
| C(31)—C(32)—H(32) | 118.9 | H(3W)—O(3)—H(4W) | 114.8 |
| C(32)—C(33)—C(1) | 114(2) | H(5W)—O(4)—H(6W) | 120.8 |
| C(32)—C(33)—H(33) | 123.2 | | |

Symmetry transformations used to generate equivalent atoms:

TABLE 40

Hydrogen coordinates (×10^4) and isotropic displacement parameters ($Å^2 \times 10^3$).

| | x | y | z | U(eq) |
|---|---|---|---|---|
| H(3) | 5255 | 2901 | −573 | 34 |
| H(2) | 3885 | 1351 | 586 | 65 |
| H(5A) | 4716 | 1038 | 1616 | 45 |
| H(5B) | 3571 | 1481 | 1678 | 45 |
| H(5C) | 4327 | 1259 | 2232 | 45 |
| H(6A) | 6667 | 1399 | 2388 | 55 |
| H(6B) | 7503 | 1822 | 2030 | 55 |
| H(6C) | 7184 | 1268 | 1758 | 55 |
| H(7A) | 4070 | 2463 | 1392 | 35 |
| H(7B) | 3571 | 2015 | 971 | 35 |
| H(8A) | 3539 | 2829 | 519 | 33 |
| H(8B) | 4534 | 2434 | 195 | 33 |
| H(11) | 5347 | 3780 | 2122 | 33 |
| H(12) | 2739 | 4125 | 1880 | 32 |
| H(14) | 5157 | 4046 | 3000 | 45 |
| H(15) | 5159 | 4601 | 3820 | 53 |
| H(16) | 3509 | 5231 | 3929 | 53 |
| H(17) | 1958 | 5381 | 3233 | 48 |
| H(18) | 1829 | 4856 | 2420 | 41 |
| H(19A) | 7460 | 3617 | 1035 | 32 |
| H(19B) | 6569 | 3941 | 1488 | 32 |
| H(20A) | 5428 | 4385 | 769 | 33 |
| H(20B) | 7040 | 4410 | 610 | 33 |
| H(25) | 6291 | 4864 | −470 | 37 |
| H(26) | 6164 | 4955 | −1463 | 40 |
| H(27) | 5870 | 4243 | −2022 | 40 |
| H(28) | 5506 | 3409 | −1659 | 39 |
| H(29A) | 7055 | 2487 | 323 | 33 |
| H(29B) | 7718 | 2939 | 701 | 33 |
| H(30A) | 6767 | 2571 | 1536 | 34 |
| H(30B) | 7727 | 2156 | 1221 | 34 |
| H(31) | 7981 | 1527 | 762 | 50 |
| H(32) | 8344 | 889 | 106 | 58 |
| H(33) | 6513 | 439 | −301 | 69 |
| H(1W) | 316 | 2664 | 1476 | 56 |
| H(2W) | 1381 | 2739 | 1053 | 56 |
| H(3W) | 4928 | 2196 | 2447 | 41 |
| H(4W) | 4046 | 2608 | 2630 | 41 |
| H(5W) | 1576 | 2797 | 2466 | 45 |
| H(6W) | 2564 | 3081 | 2102 | 45 |

TABLE 41

Anisotropic displacement parameters ($Å^2 \times 10^3$). The anisotropic displacement factor exponent takes the form: $-2\pi^2[h^2 a^{*2} U11 + \ldots + 2 h k a^* b^* U12]$

| | U11 | U22 | U33 | U23 | U13 | U12 |
|---|---|---|---|---|---|---|
| F(1) | 79(7) | 124(8) | 106(7) | −52(7) | −5(7) | 4(7) |

Polymorph C

SCXRD (Single Crystal X-Ray Diffraction)

SCXRD analyses of crystalline form C was carried out with a Bruker D8-goniometer with SMART APEX CCD area detector at 130 K (±5 K) using MoKα radiation (wavelength of 0.71073 Å, Incoatec microsource, multilayer optics).

TABLE 42

Crystal data and structure refinement

| | |
|---|---|
| Empirical formula | C35H42FN3O3 |
| Formula weight | 571.72 |
| Temperature | 130(2) K |
| Wavelength | .71073 Å |
| Crystal system | Triclinic |
| Space group | P-1 |

TABLE 42-continued

Crystal data and structure refinement

| | |
|---|---|
| Unit cell dimensions | a = 9.0215(12) Å alpha = 67.547(3) deg. |
| | b = 13.3823(17) Å beta = 81.853(4) deg. |
| | c = 13.7021(19) Å gamma = 83.608(4) deg. |
| Volume | 1510.4(3) Å^3 |
| Z | 2 |
| Density (calculated) | 1.257 Mg/m^3 |
| Absorption coefficient | 0.084 mm^−1 |
| F(000) | 612 |
| Crystal size | 0.14 × 0.13 × 0.07 mm |
| Theta range for data collection | 1.83 to 28.47 deg. |
| Index ranges | −11 <= h <= 12, −17 <= k <= 17, −17 <= l <= 17 |
| Reflections collected | 23406 |
| Independent reflections | 7011 [R(int) = 0.0494] |
| Absorption correction | None |
| Refinement method | Full-matrix least-squares on F^2 |
| Data/restraints/parameters | 7011/0/395 |
| Goodness-of-fit on F^2 | 1.052 |
| Final R indices [I > 2sigma(I)] | R1 = 0.0439, wR2 = 0.0852 |
| R indices (all data) | R1 = 0.0723, wR2 = 0.0898 |
| Largest diff. peak and hole | .277 and −.202 e · Å^−3 |

TABLE 43

Atomic coordinates (× 10^4) and equivalent isotropic displacement parameters ($Å^2 \times 10^3$). U(eq) is defined as one third of the trace of the orthogonalized Uij tensor.

| | x | y | z | U(eq) |
|---|---|---|---|---|
| F(1) | −3098(1) | 14196(1) | −739(1) | 32(1) |
| O(1) | 570(1) | 8487(1) | 4358(1) | 46(1) |
| N(1) | 886(1) | 12561(1) | 2348(1) | 21(1) |
| N(2) | 1344(1) | 9118(1) | 2565(1) | 21(1) |
| N(3) | −2295(1) | 8634(1) | 1894(1) | 23(1) |
| C(1) | −3032(2) | 13654(1) | 330(1) | 22(1) |
| C(2) | −1719(2) | 13081(1) | 654(1) | 21(1) |
| C(3) | −1605(2) | 12513(1) | 1734(1) | 20(1) |
| C(4) | −134(2) | 11872(1) | 2124(1) | 20(1) |
| C(5) | 1443(2) | 13476(1) | 1405(1) | 27(1) |
| C(6) | 236(2) | 12982(1) | 3172(1) | 28(1) |
| C(7) | 761(1) | 11453(1) | 1298(1) | 20(1) |
| C(8) | 27(2) | 10558(1) | 1155(1) | 22(1) |
| C(9) | −176(2) | 9560(1) | 2203(1) | 21(1) |
| C(10) | 1559(2) | 8592(1) | 3624(1) | 27(1) |
| C(11) | 3118(2) | 8152(1) | 3852(1) | 27(1) |
| C(12) | 3357(2) | 7256(1) | 4687(1) | 28(1) |
| C(13) | 4800(2) | 6701(1) | 5015(1) | 26(1) |
| C(14) | 4822(2) | 5706(1) | 5861(1) | 32(1) |
| C(15) | 6161(2) | 5141(1) | 6172(1) | 37(1) |
| C(16) | 7506(2) | 5556(1) | 5641(1) | 39(1) |
| C(17) | 7505(2) | 6548(1) | 4805(1) | 43(1) |
| C(18) | 6168(2) | 7110(1) | 4500(1) | 35(1) |
| C(19) | 2259(2) | 8660(1) | 1837(1) | 24(1) |
| C(20) | 1656(2) | 7592(1) | 1967(1) | 27(1) |
| C(21) | −15(2) | 7764(1) | 1943(1) | 22(1) |
| C(22) | −813(2) | 8659(1) | 2029(1) | 21(1) |
| C(23) | −2463(2) | 7688(1) | 1749(1) | 22(1) |
| C(24) | −1046(2) | 7115(1) | 1787(1) | 20(1) |
| C(25) | −928(2) | 6105(1) | 1688(1) | 23(1) |
| C(26) | −2175(2) | 5710(1) | 1532(1) | 26(1) |
| C(27) | −3567(2) | 6298(1) | 1479(1) | 29(1) |
| C(28) | −3723(2) | 7287(1) | 1589(1) | 27(1) |
| C(29) | −1192(2) | 10002(1) | 2968(1) | 22(1) |
| C(30) | −449(2) | 10877(1) | 3150(1) | 22(1) |
| C(31) | −2863(2) | 12573(1) | 2439(1) | 26(1) |
| C(32) | −4174(2) | 13151(1) | 2082(1) | 28(1) |
| C(33) | −4280(2) | 13703(1) | 1011(1) | 27(1) |
| O(2) | 3399(1) | 1185(1) | 3038(1) | 34(1) |
| C(34) | 3411(2) | 897(2) | 4142(1) | 51(1) |
| O(3) | 5196(1) | 178(1) | 1887(1) | 34(1) |
| C(35) | 5215(2) | 942(1) | 836(1) | 41(1) |

TABLE 44

| Bond lengths [A] and angles [deg]. | | | |
|---|---|---|---|
| F(1)—C(1) | 1.3706(15) | C(11)—H(11) | .9500 |
| O(1)—C(10) | 1.2214(16) | C(12)—C(13) | 1.4643(19) |
| N(1)—C(5) | 1.4708(17) | C(12)—H(12) | .9500 |
| N(1)—C(6) | 1.4711(17) | C(13)—C(18) | 1.389(2) |
| N(1)—C(4) | 1.5082(17) | C(13)—C(14) | 1.392(2) |
| N(2)—C(10) | 1.3809(18) | C(14)—C(15) | 1.382(2) |
| N(2)—C(19) | 1.4747(16) | C(14)—H(14) | .9500 |
| N(2)—C(9) | 1.5044(17) | C(15)—C(16) | 1.379(2) |
| N(3)—C(22) | 1.3813(17) | C(15)—H(15) | .9500 |
| N(3)—C(23) | 1.3815(18) | C(16)—C(17) | 1.384(2) |
| N(3)—H(3N) | .890(15) | C(16)—H(16) | .9500 |
| C(1)—C(2) | 1.3694(18) | C(17)—C(18) | 1.377(2) |
| C(1)—C(33) | 1.3701(19) | C(17)—H(17) | .9500 |
| C(2)—C(3) | 1.3943(18) | C(18)—H(18) | .9500 |
| C(2)—H(2) | .9500 | C(19)—C(20) | 1.5235(19) |
| C(3)—C(31) | 1.3981(18) | C(19)—H(19A) | .9900 |
| C(3)—C(4) | 1.5430(18) | C(19)—H(19B) | .9900 |
| C(4)—C(30) | 1.5397(18) | C(20)—C(21) | 1.5020(18) |
| C(4)—C(7) | 1.5407(18) | C(20)—H(20A) | .9900 |
| C(5)—H(5A) | .9800 | C(20)—H(20B) | .9900 |
| C(5)—H(5B) | .9800 | C(21)—C(22) | 1.3628(18) |
| C(5)—H(5C) | .9800 | C(21)—C(24) | 1.4301(19) |
| C(6)—H(6A) | .9800 | C(23)—C(28) | 1.3873(19) |
| C(6)—H(6B) | .9800 | C(23)—C(24) | 1.4120(18) |
| C(6)—H(6C) | .9800 | C(24)—C(25) | 1.3992(18) |
| C(7)—C(8) | 1.5185(18) | C(25)—C(26) | 1.3714(19) |
| C(7)—H(7A) | .9900 | C(25)—H(25) | .9500 |
| C(7)—H(7B) | .9900 | C(26)—C(27) | 1.4009(19) |
| C(8)—C(9) | 1.5468(18) | C(26)—H(26) | .9500 |
| C(8)—H(8A) | .9900 | C(27)—C(28) | 1.379(2) |
| C(8)—H(8B) | .9900 | C(27)—H(27) | .9500 |
| C(9)—C(22) | 1.5010(19) | C(28)—H(28) | .9500 |
| C(9)—C(29) | 1.5405(18) | C(29)—C(30) | 1.5255(19) |
| C(10)—C(11) | 1.491(2) | C(29)—H(29A) | .9900 |
| C(11)—C(12) | 1.3259(19) | C(29)—H(29B) | .9900 |
| C(30)—H(30A) | .9900 | N(1)—C(4)—C(7) | 106.77(10) |
| C(30)—H(30B) | .9900 | C(30)—C(4)—C(7) | 107.06(11) |
| C(31)—C(32) | 1.3817(19) | N(1)—C(4)—C(3) | 111.63(11) |
| C(31)—H(31) | .9500 | C(30)—C(4)—C(3) | 111.18(11) |
| C(32)—C(33) | 1.379(2) | C(7)—C(4)—C(3) | 112.04(11) |
| C(32)—H(32) | .9500 | N(1)—C(5)—H(5A) | 109.5 |
| C(33)—H(33) | .9500 | N(1)—C(5)—H(5B) | 109.5 |
| O(2)—C(34) | 1.4122(18) | H(5A)—C(5)—H(5B) | 109.5 |
| O(2)—H(2O) | .959(19) | N(1)—C(5)—H(5C) | 109.5 |
| C(34)—H(34A) | .9800 | H(5A)—C(5)—H(5C) | 109.5 |
| C(34)—H(34B) | .9800 | H(5B)—C(5)—H(5C) | 109.5 |
| C(34)—H(34C) | .9800 | N(1)—C(6)—H(6A) | 109.5 |
| O(3)—C(35) | 1.4115(18) | N(1)—C(6)—H(6B) | 109.5 |
| O(3)—H(3O) | .897(17) | H(6A)—C(6)—H(6B) | 109.5 |
| C(35)—H(35A) | .9800 | N(1)—C(6)—H(6C) | 109.5 |
| C(35)—H(35B) | .9800 | H(6A)—C(6)—H(6C) | 109.5 |
| C(35)—H(35C) | .9800 | H(6B)—C(6)—H(6C) | 109.5 |
| | | C(8)—C(7)—C(4) | 113.56(11) |
| C(5)—N(1)—C(6) | 108.13(11) | C(8)—C(7)—H(7A) | 108.9 |
| C(5)—N(1)—C(4) | 114.35(10) | C(4)—C(7)—H(7A) | 108.9 |
| C(6)—N(1)—C(4) | 114.17(10) | C(8)—C(7)—H(7B) | 108.9 |
| C(10)—N(2)—C(19) | 115.06(11) | C(4)—C(7)—H(7B) | 108.9 |
| C(10)—N(2)—C(9) | 122.53(11) | H(7A)—C(7)—H(7B) | 107.7 |
| C(19)—N(2)—C(9) | 111.79(10) | C(7)—C(8)—C(9) | 111.94(11) |
| C(22)—N(3)—C(23) | 108.44(12) | C(7)—C(8)—H(8A) | 109.2 |
| C(22)—N(3)—H(3N) | 124.0(10) | C(9)—C(8)—H(8A) | 109.2 |
| C(23)—N(3)—H(3N) | 127.4(10) | C(7)—C(8)—H(8B) | 109.2 |
| C(2)—C(1)—C(33) | 123.72(14) | C(9)—C(8)—H(8B) | 109.2 |
| C(2)—C(1)—F(1) | 117.76(12) | H(8A)—C(8)—H(8B) | 107.9 |
| C(33)—C(1)—F(1) | 118.52(12) | C(22)—C(9)—N(2) | 105.47(10) |
| C(1)—C(2)—C(3) | 119.65(13) | C(22)—C(9)—C(29) | 114.07(11) |
| C(1)—C(2)—H(2) | 120.2 | N(2)—C(9)—C(29) | 113.37(11) |
| C(3)—C(2)—H(2) | 120.2 | C(22)—C(9)—C(8) | 111.02(11) |
| C(2)—C(3)—C(31) | 117.19(13) | N(2)—C(9)—C(8) | 108.77(10) |
| C(2)—C(3)—C(4) | 120.84(12) | C(29)—C(9)—C(8) | 104.15(10) |
| C(31)—C(3)—C(4) | 121.96(12) | O(1)—C(10)—N(2) | 124.17(14) |
| N(1)—C(4)—C(30) | 107.89(10) | O(1)—C(10)—C(11) | 119.73(13) |
| N(2)—C(10)—C(11) | 116.09(12) | C(22)—C(21)—C(24) | 107.31(12) |
| C(12)—C(11)—C(10) | 120.45(14) | C(22)—C(21)—C(20) | 122.89(12) |
| C(12)—C(11)—H(11) | 119.8 | C(24)—C(21)—C(20) | 129.73(12) |
| C(10)—C(11)—H(11) | 119.8 | C(21)—C(22)—N(3) | 109.76(12) |
| C(11)—C(12)—C(13) | 127.74(14) | C(21)—C(22)—C(9) | 125.41(12) |
| C(11)—C(12)—H(12) | 116.1 | N(3)—C(22)—C(9) | 124.79(12) |

TABLE 44-continued

Bond lengths [Å] and angles [deg].

| | | | | |
|---|---|---|---|---|
| C(13)—C(12)—H(12) | 116.1 | N(3)—C(23)—C(28) | 130.61(13) |
| C(18)—C(13)—C(14) | 117.84(14) | N(3)—C(23)—C(24) | 107.78(12) |
| C(18)—C(13)—C(12) | 122.81(13) | C(28)—C(23)—C(24) | 121.61(13) |
| C(14)—C(13)—C(12) | 119.32(14) | C(25)—C(24)—C(23) | 118.83(13) |
| C(15)—C(14)—C(13) | 121.03(15) | C(25)—C(24)—C(21) | 134.51(13) |
| C(15)—C(14)—H(14) | 119.5 | C(23)—C(24)—C(21) | 106.66(12) |
| C(13)—C(14)—H(14) | 119.5 | C(26)—C(25)—C(24) | 119.45(13) |
| C(16)—C(15)—C(14) | 120.18(15) | C(26)—C(25)—H(25) | 120.3 |
| C(16)—C(15)—H(15) | 119.9 | C(24)—C(25)—H(25) | 120.3 |
| C(14)—C(15)—H(15) | 119.9 | C(25)—C(26)—C(27) | 120.93(14) |
| C(15)—C(16)—C(17) | 119.52(15) | C(25)—C(26)—H(26) | 119.5 |
| C(15)—C(16)—H(16) | 120.2 | C(27)—C(26)—H(26) | 119.5 |
| C(17)—C(16)—H(16) | 120.2 | C(28)—C(27)—C(26) | 120.94(14) |
| C(18)—C(17)—C(16) | 120.07(16) | C(28)—C(27)—H(27) | 119.5 |
| C(18)—C(17)—H(17) | 120.0 | C(26)—C(27)—H(27) | 119.5 |
| C(16)—C(17)—H(17) | 120.0 | C(27)—C(28)—C(23) | 118.22(13) |
| C(17)—C(18)—C(13) | 121.35(15) | C(27)—C(28)—H(28) | 120.9 |
| C(17)—C(18)—H(18) | 119.3 | C(23)—C(28)—H(28) | 120.9 |
| C(13)—C(18)—H(18) | 119.3 | C(30)—C(29)—C(9) | 111.42(11) |
| N(2)—C(19)—C(20) | 109.67(11) | C(30)—C(29)—H(29A) | 109.3 |
| N(2)—C(19)—H(19A) | 109.7 | C(9)—C(29)—H(29A) | 109.3 |
| C(20)—C(19)—H(19A) | 109.7 | C(30)—C(29)—H(29B) | 109.3 |
| N(2)—C(19)—H(19B) | 109.7 | C(9)—C(29)—H(29B) | 109.3 |
| C(20)—C(19)—H(19B) | 109.7 | H(29A)—C(29)—H(29B) | 108.0 |
| H(19A)—C(19)—H(19B) | 108.2 | C(29)—C(30)—C(4) | 112.79(11) |
| C(21)—C(20)—C(19) | 108.06(11) | C(29)—C(30)—H(30A) | 109.0 |
| C(21)—C(20)—H(20A) | 110.1 | C(4)—C(30)—H(30A) | 109.0 |
| C(19)—C(20)—H(20A) | 110.1 | C(29)—C(30)—H(30B) | 109.0 |
| C(21)—C(20)—H(20B) | 110.1 | C(4)—C(30)—H(30B) | 109.0 |
| C(19)—C(20)—H(20B) | 110.1 | H(30A)—C(30)—H(30B) | 107.8 |
| H(20A)—C(20)—H(20B) | 108.4 | C(32)—C(31)—C(3) | 121.53(14) |
| C(32)—C(31)—H(31) | 119.2 | H(34A)—C(34)—H(34B) | 109.5 |
| C(3)—C(31)—H(31) | 119.2 | O(2)—C(34)—H(34C) | 109.5 |
| C(33)—C(32)—C(31) | 120.88(13) | H(34A)—C(34)—H(34C) | 109.5 |
| C(33)—C(32)—H(32) | 119.6 | H(34B)—C(34)—H(34C) | 109.5 |
| C(31)—C(32)—H(32) | 119.6 | C(35)—O(3)—H(3O) | 105.6(11) |
| C(1)—C(33)—C(32) | 117.02(13) | O(3)—C(35)—H(35A) | 109.5 |
| C(1)—C(33)—H(33) | 121.5 | O(3)—C(35)—H(35B) | 109.5 |
| C(32)—C(33)—H(33) | 121.5 | H(35A)—C(35)—H(35B) | 109.5 |
| C(34)—O(2)—H(2O) | 110.1(11) | O(3)—C(35)—H(35C) | 109.5 |
| O(2)—C(34)—H(34A) | 109.5 | H(35A)—C(35)—H(35C) | 109.5 |
| O(2)—C(34)—H(34B) | 109.5 | H(35B)—C(35)—H(35C) | 109.5 |

Symmetry transformations used to generate equivalent atoms:

TABLE 45

Hydrogen coordinates (×10^4) and isotropic displacement parameters (Å^2 × 10^3).

| | x | y | z | U(eq) |
|---|---|---|---|---|
| H(3N) | −3011(17) | 9131(12) | 1945(11) | 38(5) |
| H(2) | −889 | 13070 | 146 | 25 |
| H(5A) | 591 | 13955 | 1090 | 41 |
| H(5B) | 2009 | 13201 | 885 | 41 |
| H(5C) | 2097 | 13880 | 1614 | 41 |
| H(6A) | 1002 | 13341 | 3337 | 42 |
| H(6B) | −120 | 12382 | 3815 | 42 |
| H(6C) | −607 | 13504 | 2915 | 42 |
| H(7A) | 882 | 12066 | 605 | 24 |
| H(7B) | 1774 | 11180 | 1518 | 24 |
| H(8A) | 653 | 10335 | 609 | 26 |
| H(8B) | −966 | 10838 | 899 | 26 |
| H(11) | 3947 | 8517 | 3396 | 32 |
| H(12) | 2489 | 6935 | 5124 | 34 |
| H(14) | 3901 | 5411 | 6229 | 38 |
| H(15) | 6154 | 4465 | 6753 | 45 |
| H(16) | 8427 | 5162 | 5847 | 47 |
| H(17) | 8428 | 6843 | 4441 | 52 |
| H(18) | 6181 | 7791 | 3925 | 42 |
| H(19A) | 3316 | 8537 | 1996 | 28 |
| H(19B) | 2227 | 9176 | 1095 | 28 |
| H(20A) | 2119 | 7358 | 1383 | 33 |
| H(20B) | 1898 | 7023 | 2649 | 33 |
| H(25) | 9 | 5698 | 1730 | 28 |
| H(26) | −2095 | 5027 | 1459 | 31 |
| H(27) | −4415 | 6011 | 1364 | 35 |
| H(28) | −4668 | 7683 | 1556 | 33 |
| H(29A) | −2153 | 10307 | 2671 | 27 |
| H(29B) | −1414 | 9401 | 3657 | 27 |
| H(30A) | 509 | 10567 | 3452 | 26 |
| H(30B) | −1108 | 11111 | 3676 | 26 |
| H(31) | −2814 | 12208 | 3181 | 31 |
| H(32) | −5015 | 13168 | 2580 | 34 |
| H(33) | −5178 | 14100 | 758 | 33 |
| H(2O) | 2570(2) | 1694(16) | 2792(15) | 79(7) |
| H(34A) | 4130 | 1321 | 4266 | 77 |
| H(34B) | 3705 | 123 | 4469 | 77 |
| H(34C) | 2407 | 1046 | 4456 | 77 |
| H(3O) | 4624(19) | 497(14) | 2292(14) | 57(6) |
| H(35A) | 4195 | 1084 | 625 | 62 |
| H(35B) | 5872 | 655 | 358 | 62 |
| H(35C) | 5591 | 1618 | 796 | 62 |

TABLE 46

Anisotropic displacement parameters ($Å^2 \times 10^3$).
The anisotropic displacement factor exponent takes the form:
$-2\pi^2 [h^2 a^{*2} U11 + \ldots + 2 h k a^* b^* U12]$

|  | U11 | U22 | U33 | U23 | U13 | U12 |
|---|---|---|---|---|---|---|
| F(1) | 32(1) | 29(1) | 31(1) | −8(1) | −9(1) | 6(1) |
| O(1) | 48(1) | 47(1) | 24(1) | 0(1) | 5(1) | 19(1) |
| N(1) | 23(1) | 20(1) | 22(1) | −8(1) | −1(1) | −2(1) |
| N(2) | 22(1) | 20(1) | 21(1) | −9(1) | −1(1) | 1(1) |
| N(3) | 20(1) | 20(1) | 31(1) | −12(1) | −3(1) | 4(1) |
| C(1) | 26(1) | 16(1) | 26(1) | −7(1) | −6(1) | −2(1) |
| C(2) | 21(1) | 18(1) | 25(1) | −10(1) | 0(1) | −1(1) |
| C(3) | 20(1) | 15(1) | 26(1) | −10(1) | −1(1) | −2(1) |
| C(4) | 20(1) | 20(1) | 20(1) | −8(1) | −2(1) | 0(1) |
| C(5) | 28(1) | 24(1) | 29(1) | −9(1) | −1(1) | −7(1) |
| C(6) | 33(1) | 27(1) | 26(1) | −13(1) | −4(1) | −2(1) |
| C(7) | 19(1) | 19(1) | 19(1) | −5(1) | −2(1) | 2(1) |
| C(8) | 22(1) | 22(1) | 20(1) | −9(1) | −2(1) | 3(1) |
| C(9) | 19(1) | 20(1) | 22(1) | −9(1) | −1(1) | 1(1) |
| C(10) | 35(1) | 18(1) | 24(1) | −5(1) | −2(1) | 3(1) |
| C(11) | 33(1) | 24(1) | 22(1) | −7(1) | −4(1) | −1(1) |
| C(12) | 33(1) | 27(1) | 23(1) | −9(1) | −1(1) | 1(1) |
| C(13) | 33(1) | 26(1) | 21(1) | −11(1) | −6(1) | 2(1) |
| C(14) | 34(1) | 29(1) | 28(1) | −8(1) | −3(1) | 3(1) |
| C(15) | 45(1) | 30(1) | 32(1) | −6(1) | −10(1) | 5(1) |
| C(16) | 36(1) | 44(1) | 40(1) | −17(1) | −17(1) | 9(1) |
| C(17) | 35(1) | 52(1) | 39(1) | −10(1) | −7(1) | −6(1) |
| C(18) | 39(1) | 34(1) | 27(1) | −3(1) | −10(1) | −2(1) |
| C(19) | 19(1) | 28(1) | 25(1) | −13(1) | 0(1) | 3(1) |
| C(20) | 25(1) | 26(1) | 35(1) | −17(1) | −4(1) | 5(1) |
| C(21) | 22(1) | 20(1) | 23(1) | −9(1) | −1(1) | 1(1) |
| C(22) | 21(1) | 20(1) | 21(1) | −7(1) | 0(1) | 2(1) |
| C(23) | 25(1) | 20(1) | 20(1) | −8(1) | −1(1) | 0(1) |
| C(24) | 21(1) | 20(1) | 19(1) | −7(1) | −2(1) | 1(1) |
| C(25) | 23(1) | 19(1) | 25(1) | −7(1) | −1(1) | 1(1) |
| C(26) | 32(1) | 20(1) | 26(1) | −9(1) | −2(1) | −2(1) |
| C(27) | 26(1) | 32(1) | 33(1) | −14(1) | −2(1) | −6(1) |
| C(28) | 21(1) | 29(1) | 32(1) | −12(1) | −3(1) | 2(1) |
| C(29) | 22(1) | 20(1) | 23(1) | −8(1) | 1(1) | 0(1) |
| C(30) | 24(1) | 20(1) | 21(1) | −8(1) | 0(1) | 2(1) |
| C(31) | 26(1) | 23(1) | 27(1) | −10(1) | 1(1) | −1(1) |
| C(32) | 21(1) | 26(1) | 38(1) | −15(1) | 6(1) | −2(1) |
| C(33) | 18(1) | 22(1) | 43(1) | −14(1) | −5(1) | 2(1) |
| O(2) | 32(1) | 40(1) | 31(1) | −14(1) | −8(1) | 8(1) |
| C(34) | 61(1) | 56(1) | 40(1) | −19(1) | −24(1) | 16(1) |
| O(3) | 32(1) | 29(1) | 36(1) | −11(1) | 0(1) | 8(1) |
| C(35) | 40(1) | 37(1) | 41(1) | −12(1) | 5(1) | 1(1) |

Analysis—FT Raman Spectroscopy

FT Raman spectra were recorded on a Bruker RFS100/S Raman spectrometer (Nd-YAG 100 mW laser, excitation 1064 nm, Ge detector, 64 scans, 25-3500 $cm^{-1}$, resolution 2 $cm^{-1}$).

Raman peak tables were generated using the ACD/SpecManager (Product Version12.5) software from ACD/Labs using the following parameters for the Auto Peak Picking:

| Noise Factor: | 0.2 (for crystalline forms A and B) |
|---|---|
|  | 0.5 (for crystalline form D) |
| Minimum Peak Level: | 0% of max Intensity |
| Peaks: | positive |
| FWHH Options: | calculate automatically |
| Area Baseline: | zero |

For the intensity classification, the absolute intensity was used and the most intense peak was scaled to 100%. The classification is as follow: very strong (vs): I>90%; strong (s): 90%≥I>60%; medium (m): 60%≥I>30%; weak (w): 30%≥I>10%; and very weak (vw): 10%≥I.

TABLE 47

Figure 2A:
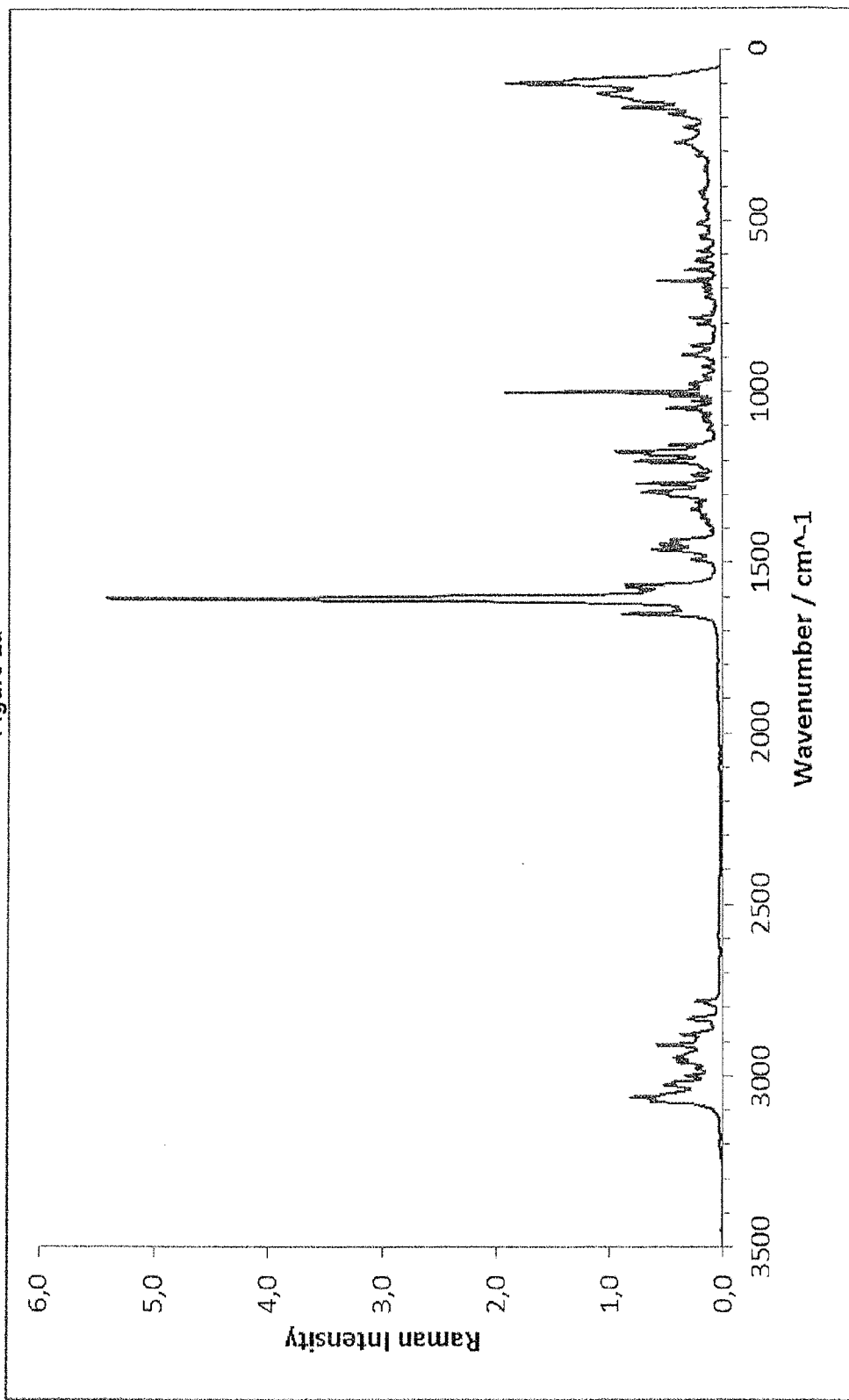
FIGS. 2a, 2b and 2d show the Raman spectra of crystalline forms A, B, and D.

RAMAN peak-list of crystalline form A; spectrum shown in FIG. 2a

| No. | $cm^{-1}$ | Intensity |
|---|---|---|
| 1 | 98 | M |
| 2 | 128 | W |
| 3 | 170 | W |
| 4 | 189 | VW |
| 5 | 227 | VW |
| 6 | 272 | VW |
| 7 | 310 | VW |
| 8 | 355 | VW |
| 9 | 417 | VW |
| 10 | 461 | VW |
| 11 | 485 | VW |
| 12 | 509 | VW |
| 13 | 543 | VW |
| 14 | 589 | VW |
| 15 | 611 | VW |
| 16 | 620 | VW |
| 17 | 644 | VW |
| 18 | 676 | W |
| 19 | 697 | VW |
| 20 | 725 | VW |
| 21 | 746 | VW |
| 22 | 783 | VW |
| 23 | 801 | VW |
| 24 | 831 | VW |
| 25 | 865 | VW |
| 26 | 893 | VW |
| 27 | 927 | VW |
| 28 | 955 | VW |
| 29 | 978 | VW |
| 30 | 1001 | M |
| 31 | 1012 | VW |
| 32 | 1028 | VW |
| 33 | 1048 | VW |
| 34 | 1074 | VW |
| 35 | 1111 | VW |
| 36 | 1155 | VW |
| 37 | 1175 | W |
| 38 | 1183 | W |
| 39 | 1204 | W |
| 40 | 1244 | VW |
| 41 | 1268 | W |
| 42 | 1294 | W |
| 43 | 1343 | VW |
| 44 | 1368 | VW |
| 45 | 1385 | VW |
| 46 | 1407 | VW |
| 47 | 1447 | W |
| 48 | 1462 | W |
| 49 | 1493 | VW |
| 50 | 1568 | W |
| 51 | 1574 | W |
| 52 | 1584 | W |
| 53 | 1606 | VS |
| 54 | 1650 | W |
| 55 | 2782 | VW |
| 56 | 2834 | VW |
| 57 | 2878 | VW |
| 58 | 2910 | W |
| 59 | 2946 | VW |
| 60 | 2960 | VW |
| 61 | 2980 | VW |
| 62 | 2999 | VW |
| 63 | 3026 | VW |
| 64 | 3062 | W |
| 65 | 3075 | W |
| 66 | 3449 | VW |

TABLE 48

Figure 2B:
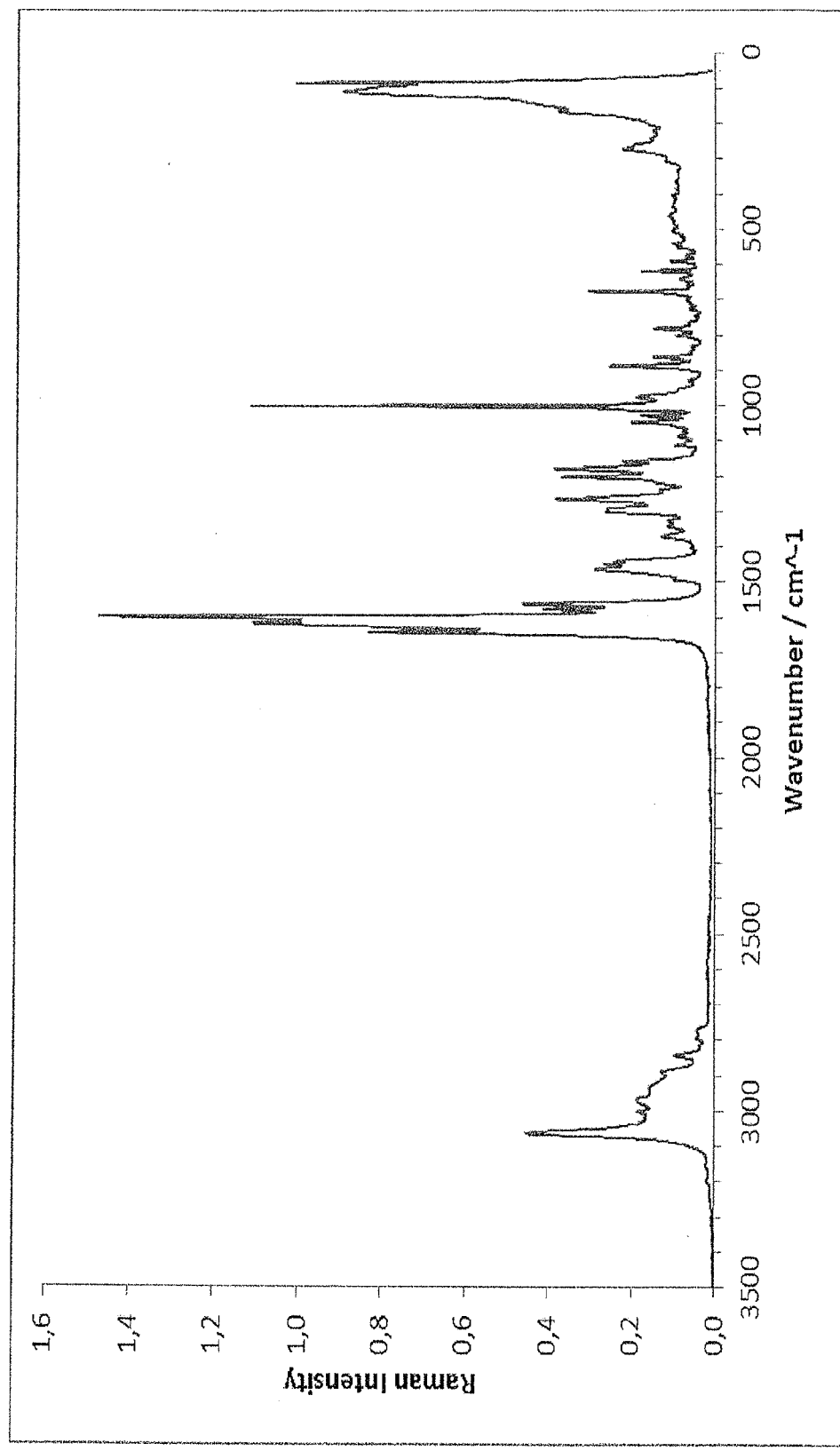

RAMAN peak-list of crystalline form B; spectrum shown in FIG. 2b

| No | cm$^{-1}$ | Intensity |
|---|---|---|
| 1 | 84 | S |
| 2 | 109 | S |
| 3 | 166 | W |
| 4 | 220 | W |
| 5 | 272 | W |
| 6 | 333 | VW |
| 7 | 365 | VW |
| 8 | 387 | VW |
| 9 | 405 | VW |
| 10 | 435 | VW |
| 11 | 463 | VW |
| 12 | 505 | VW |
| 13 | 541 | VW |
| 14 | 590 | VW |
| 15 | 619 | W |
| 16 | 643 | VW |
| 17 | 676 | W |
| 18 | 725 | VW |
| 19 | 745 | VW |
| 20 | 781 | W |
| 21 | 802 | VW |
| 22 | 834 | VW |
| 23 | 862 | W |
| 24 | 888 | W |
| 25 | 929 | VW |
| 26 | 976 | W |
| 27 | 1001 | S |
| 28 | 1010 | W |
| 29 | 1029 | W |
| 30 | 1047 | W |
| 31 | 1087 | VW |
| 32 | 1112 | VW |
| 33 | 1158 | W |
| 34 | 1180 | W |
| 35 | 1203 | W |
| 36 | 1266 | W |
| 37 | 1300 | W |
| 38 | 1326 | VW |
| 39 | 1341 | VW |
| 40 | 1373 | VW |
| 41 | 1405 | VW |
| 42 | 1441 | W |
| 43 | 1449 | W |
| 44 | 1465 | W |
| 45 | 1563 | M |
| 46 | 1578 | W |
| 47 | 1601 | VS |
| 48 | 1618 | S |
| 49 | 1643 | M |
| 50 | 1861 | VW |
| 51 | 2136 | VW |
| 52 | 2172 | VW |
| 53 | 2328 | VW |
| 54 | 2489 | VW |
| 55 | 2519 | VW |
| 56 | 2558 | VW |
| 57 | 2772 | VW |
| 58 | 2794 | VW |
| 59 | 2843 | VW |
| 60 | 2890 | VW |
| 61 | 2935 | W |
| 62 | 2967 | W |
| 63 | 3001 | W |
| 64 | 3063 | M |
| 65 | 3153 | VW |
| 66 | 3197 | VW |
| 67 | 3243 | VW |
| 68 | 3323 | VW |
| 69 | 3459 | VW |

TABLE XY3

Figure 2D:
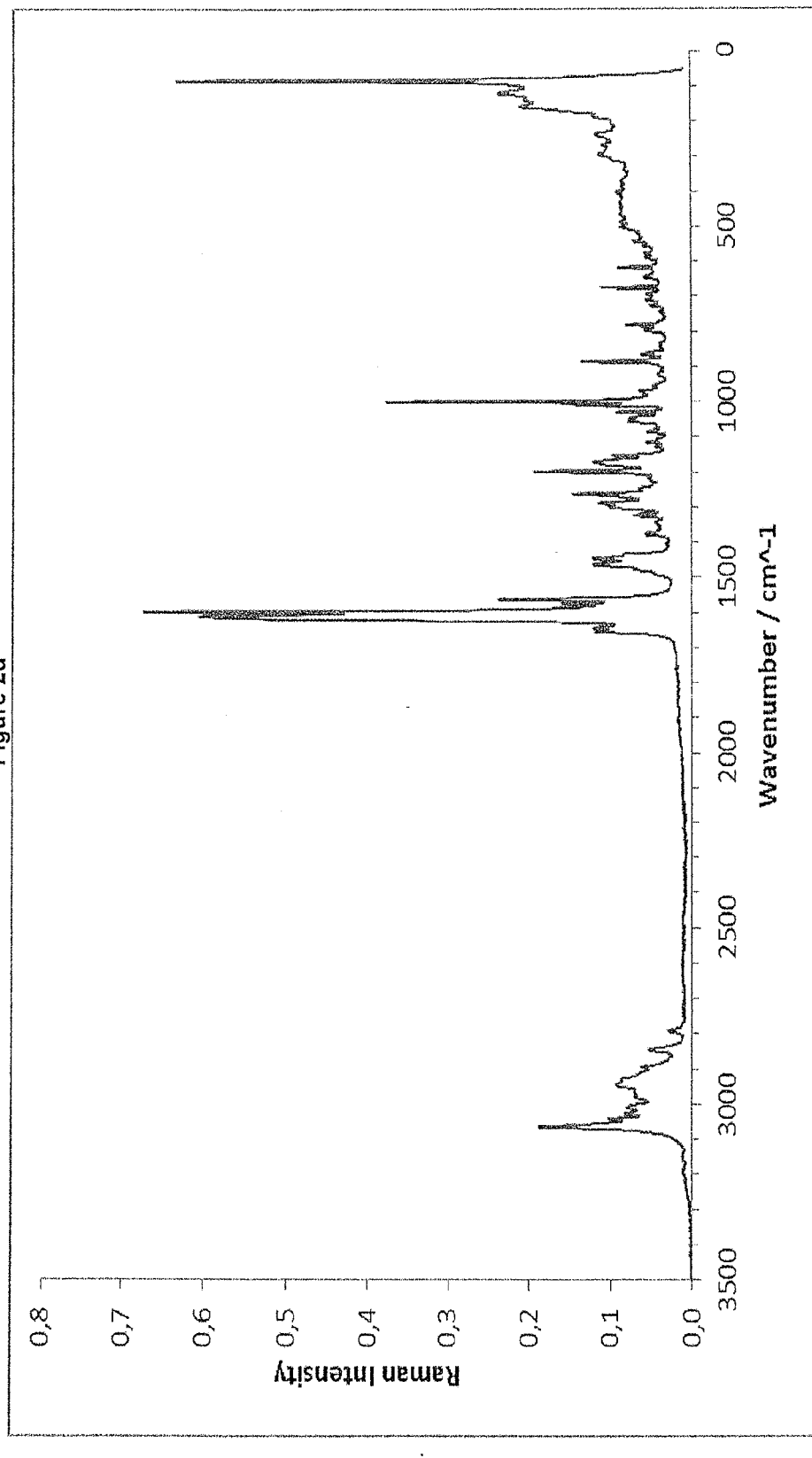

RAMAN peak-list of crystalline form D: shown in FIG. 2d.

| No | cm$^{-1}$ | Intensity |
|---|---|---|
| 1 | 84 | VS |
| 2 | 121 | M |
| 3 | 158 | M |
| 4 | 237 | W |
| 5 | 268 | W |
| 6 | 294 | W |
| 7 | 335 | W |
| 8 | 372 | W |
| 9 | 402 | W |
| 10 | 434 | W |
| 11 | 466 | W |
| 12 | 489 | W |
| 13 | 503 | W |
| 14 | 542 | W |
| 15 | 579 | VW |
| 16 | 618 | W |
| 17 | 646 | VW |
| 18 | 675 | W |
| 19 | 696 | VW |
| 20 | 711 | VW |
| 21 | 727 | VW |
| 22 | 782 | W |
| 23 | 799 | VW |
| 24 | 834 | VW |
| 25 | 867 | VW |
| 26 | 886 | W |
| 27 | 921 | VW |
| 28 | 970 | VW |
| 29 | 1000 | M |
| 30 | 1011 | W |
| 31 | 1030 | W |
| 32 | 1056 | W |
| 33 | 1085 | VW |
| 34 | 1115 | VW |
| 35 | 1154 | W |
| 36 | 1171 | W |
| 37 | 1199 | W |
| 38 | 1263 | W |
| 39 | 1289 | W |
| 40 | 1325 | W |
| 41 | 1343 | VW |
| 42 | 1377 | VW |
| 43 | 1406 | VW |
| 44 | 1447 | W |
| 45 | 1464 | W |
| 46 | 1563 | M |
| 47 | 1576 | W |
| 48 | 1599 | VS |
| 49 | 1612 | S |
| 50 | 1644 | W |
| 51 | 2792 | VW |
| 52 | 2846 | VW |
| 53 | 2895 | VW |
| 54 | 2946 | W |
| 55 | 2980 | W |
| 56 | 3010 | W |
| 57 | 3065 | W |
| 58 | 3152 | VW |
| 59 | 3196 | VW |

Analysis—DSC

Differential Scanning Calorimetry (DSC): device reference Mettler Toledo DSC821 or Mettler Toledo DSC823. Unless otherwise specified, the samples were weighed in a pierced aluminium crucible. The measurement took place in a nitrogen flow in a temperature range from −50° C. up to 350° C. with a heating rate of 10° C./min. The temperatures specified in relation to DSC analyses are, unless otherwise specified, the temperatures of the peak onset.

In the following table, "ΔH" means "specific heat", "$T_{onset}$" means the "onset temperature", and "$T_{peak}$" means the "peak temperature" of a thermal event.

The values for ΔH, $T_{onset}$ and $T_{peak}$ for each polymorph listed below are given as ranges derived from the measurement of different samples exhibiting essentially identical x-ray powder diffractograms. If a sample exhibited more than one thermal event ΔH, $T_{onset}$ and $T_{peak}$ are listed for each event.

TABLE 50

DSC data

| | $T_{onset}$ [° C.] | $T_{peak}$ [° C.] | ΔH [J/g] |
|---|---|---|---|
| Crystalline Form A | 227-247 | 235-255 | >80 |
| Crystalline Form B | 40-108 | 80-110 | 50-264 |
| | 133-140 | 142-148 | −23-27 |
| | 194-224 | 204-231 | −96−−3 |
| | 230-250 | 230-255 | 80-110 |
| Crystalline Form C | 50-145 | 60-150 | 5-200 |
| | 145-150 | 150-165 | 0-2 |
| | 165-170 | 170-175 | 0-2 |
| | 170-210 | 175-220 | −85−−50 |
| | 220-245 | 230-255 | 75-95 |
| Crystalline Form D | 30-55 | 55-95 | 10-85 |
| | 135-160 | 150-170 | 30-90 |
| | 160-175 | 160-180 | 2-7 |
| | 190-215 | 205-225 | −85−−3 |
| | 225-245 | 230-250 | 5-95 |
| Crystalline Form E | 34-41 | 51-64 | 3-7 |
| | 120-122 | 125-127 | 1-20 |
| | 134-140 | 143-146 | 2-31 |
| | 153-154 | 168-169 | 2-6 |
| | 182-197 | 196-210 | −74−−48 |
| | 223-230 | 230-250 | 65-90 |
| Crystalline Form F | (n.d.) | (n.d.) | (n.d) |
| Crystalline Form G | 35-143 | 67-149 | 34-269 |
| | 187-201 | 204-220 | −112−−62 |
| | 220-244 | 229-248 | 65-90 |
| Crystalline Form H | 135-145 | 145-160 | 40-80 |
| | 150-170 | 150-190 | −60−−20 |
| | 230-250 | 230-255 | 80-110 |
| Crystalline Form I | (n.d.) | (n.d.) | (n.d) |
| Crystalline Form J | 46.7 | 61.2 | 10 |
| (one sample measured) | 123.0 | 130.3 | 11 |
| | 186.0 | 196.8 | −84 |
| | 222.7 | 232.7 | 86 |
| Crystalline Form K | (n.d.) | (n.d.) | (n.d) |
| Crystalline Form L | 100-120 | 115-125 | 4-50 |
| | 130-140 | 140-150 | 70-120 |
| | 150-160 | 155-175 | 4−−50 |
| | 180-195 | 190-210 | −80−−20 |
| | 220-240 | 225-250 | 40-80 |
| Crystalline Form Q | 100-115 | 115-140 | 2-50 |
| | 130-140 | 130-140 | 2-50 |
| | 144-157 | 155-165 | 2-25 |
| | 175-190 | 185-205 | −90−−40 |
| | 210-225 | 220-250 | 20-105 | n.d. = not determined

The above data shows for crystalline A that it has a relatively high melting point and that no transformations into other crystalline forms of compound (1) take place up to its melting point. Both of these properties are very favorable for the use of this crystalline form in the formulation of solid dosage forms.

Analysis—TG

Thermogravimetry analytical experiments were recorded with a Mettler Toledo TGA/DSC1 (open aluminium oxide crucible nitrogen atmosphere, heating rate 10° C./min, 25 up to 350° C.). Results of the measurements are discussed below.

Analysis—DVS

Crystalline forms were characterized by dynamic vapor sorption (DVS) using a Porotec DVS 1000 or a SMS DVS Intrinsic water vapor sorption analyzer. For the DVS analysis, a step width of 10% r.h. was applied allowing the samples to equilibrate and reach weight constancy (±0.002%) for at least 10 min on each step. All measurements were performed according to the following program: 50% r.h.→90% r.h., 90%→0% r.h., 0%→90% r.h., 90%→50% r.h. A cycle with increasing humidity is also known as a sorption cycle, a cycle with decreasing humidity is also known as a desorption cycle. The details of the respective DVS measurements are shown below in table 51 and discussed further below.

The hygroscopicity of the respective crystalline forms determined via the DVS measurements was classified according to the ranges for mass increase defined in the European Pharmacopoeia: very hygroscopic (vh): increase of the mass ≥15%; hygroscopic (h): increase of the mass is less than 15% and equal or greater than 2%; slightly hygroscopic (sh): increase of the mass is less than 2% and equal or greater than 0.2%; not hygroscopic (nh): increase of the mass is less than 0.2%; deliquescent (d): sufficient water is absorbed to form a liquid.

TABLE 51

DVS measurements

| Measurement no. | Crystalline Form | T [° C.] | Initial weight [mg] |
|---|---|---|---|
| 1 | A | 24.9 | 16.7255 |
| 2 | B | 24.9 | 9.832 |
| 3 | C | 25.4 | 21.2031 |
| 4 | D | 24.9 | 7.2134 |
| 5 | E | 24.9 | 3.8075 |

Crystalline Form A:

TGA analysis performed with samples of crystalline form A revealed that these samples do not contain any significant quantities (i.e. weight loss in TGA is less or equal than 2.0%, preferably less or equal than 1.0%, even more preferably less or equal than 0.5%, most preferably less than 0.2%) of residual solvents. This is in line with the assumption that crystalline form A is an ansolvate form.

Figure 3A:
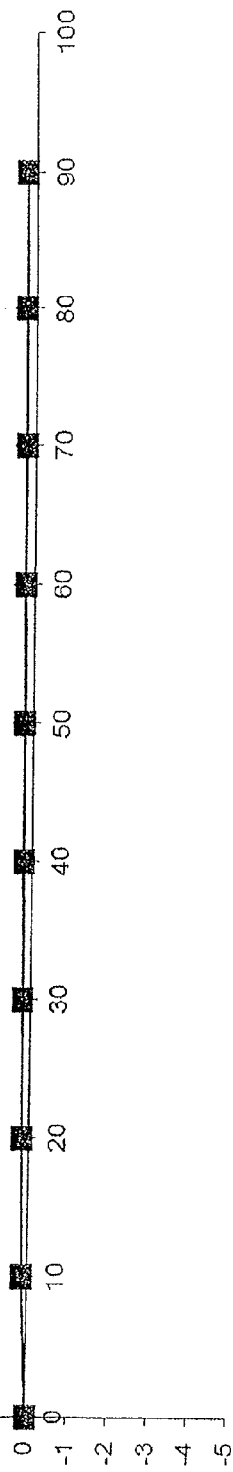
FIGS. 3a, b, c, d, and e show plots of DVS experiments for crystalline forms A, B, C, D, and E.

A sample of crystalline form A was analyzed via DVS. Crystalline form A showed no essential change, especially increase, in mass with increasing/decreasing relative humidity (−0.2 to 0.1%). Furthermore crystalline form A does not show a hysteresis bigger than 0.5%, preferably bigger than 0.1% (see FIG. 3a).

DVS measurements therefor revealed that crystalline form A is not hygroscopic or just slightly hygroscopic.

Crystalline Form B:

TGA analyses performed with samples of crystalline form B revealed that these samples showed a weight loss between about 5-10% of water agreeing with a sesqui-, di- or trihydrate form. In the majority of measurements the amount of water contained therein agreed with crystalline form B representing a trihydrate form.

But the existence of crystalline form B being a hydrate with other variable or discrete states of moisture content (e.g. dihydrate) cannot be fully excluded, since dynamic vapor sorption (DVS) experiments show a significant hysteresis (i.e. >0.5%, compare data in FIG. 3b) between 10% to 40% relative humidity and a maximum weight gain, caused by moisture uptake, of about 7.4% to 10.6% in a range between 20% and 90% relative humidity.

Figure 3C:
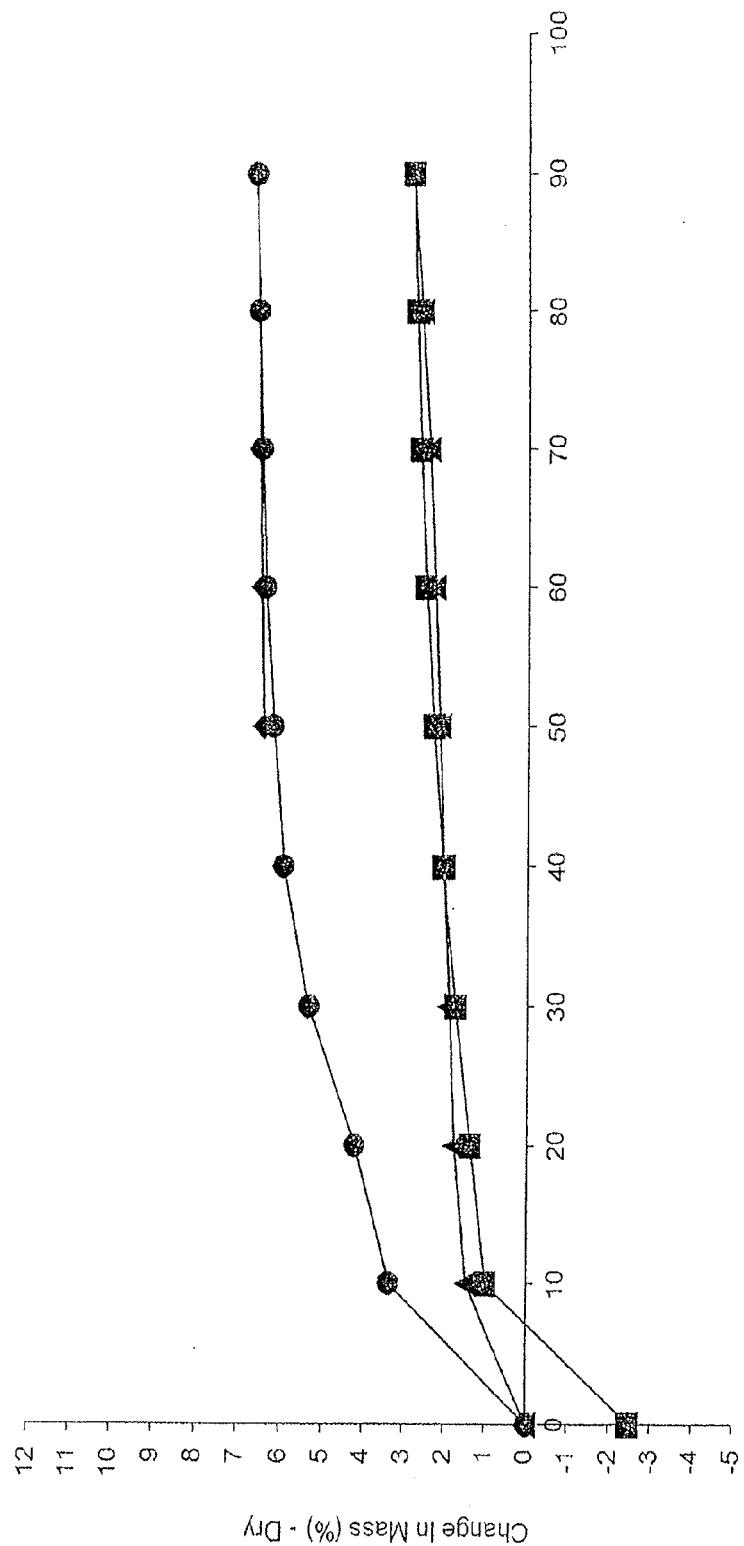

Crystalline Form C:

TGA analyses performed with samples of crystalline form C revealed that these samples exhibited a weight loss up to 9-10% which is in accordance with the presence of two molecules of methanol per molecule of the title compound (see FIG. 3c). Crystalline form C is therefore considered to be a dimethanol solvate.

Dynamic vapor sorption (DVS) experiments shows two levels of maximum weight gain, indicating that initial amounts of solvent (e.g. methanol) may be exchanged by water.

When Polymorph C is exposed to increasing moisture content (sorption cycle from 50% to 90% relative humidity) no major change in mass is observed. Upon decreasing moisture in its environment a weight loss of about 6.6% can be observed (desorption cycle from 90 to 0% r.h.). This weight loss is not fully compensated in a subsequent sorption cycle, weight gain at 90% is only about 2.8%. Furthermore, the next desorption cycle indicates that even more solvent is exchanged. Crystalline form C can rather easily loose or exchange solvent to form other crystalline forms (e.g. to yield crystalline form K or crystalline form J), therefore crystalline form C may also exist in crystalline states with varying solvent content.

It cannot be excluded that crystalline form C has transformed to another crystalline form (e.g. crystalline form K or crystalline form J) under conditions of the DVS experiments.

But the assumption that crystalline form C exists as a dimethanol solvate form is proven by x-ray single crystal structure analysis.

Crystalline Form D:

TGA analyses performed with samples of crystalline form D obtained from solutions in different solvents, revealed residual solvent contents of between 0.1-4.7%. Seen in conjunction with the results from the other analytical methods described herein, crystalline form D is considered to be an ansolvate form with varying amounts of residual solvent.

Figure 3D:
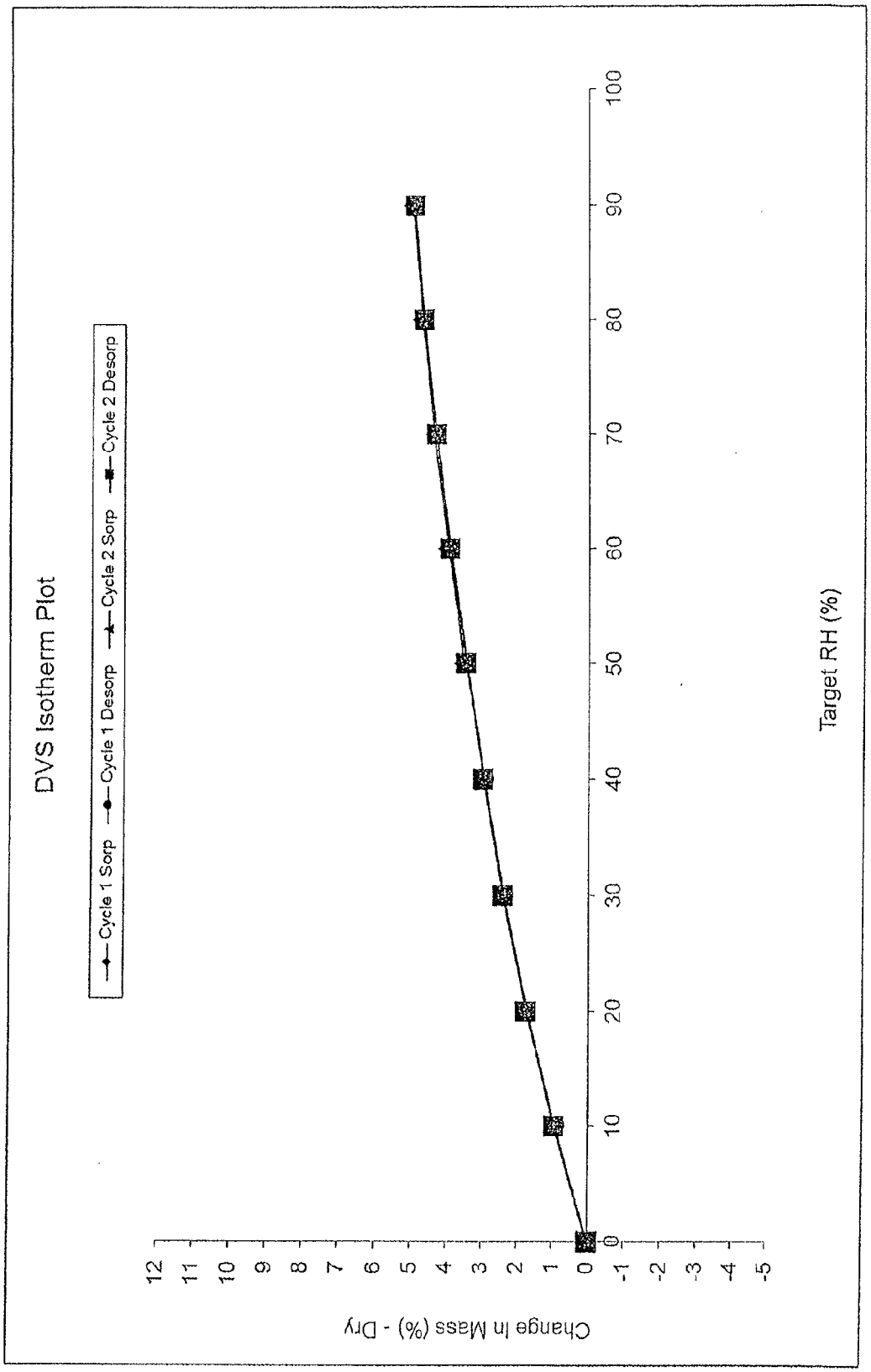

Based on the DVS experiments the existence of crystalline form D with variable solvate or non-stoichiometric content cannot be fully excluded. Sorption and desorption behavior, which shows no significant hysteresis (see FIG. 3d) is indicative of a channel-type crystal structure or another structure type that easily allows moisture exchange. The DVS experiments of crystalline form D showed a maximum weight gain of about 2.0 to 8.1% at 90% relative humidity.

It cannot be excluded that crystalline form D has transformed to another crystalline form (e.g. crystalline form G) under conditions of the DVS experiments.

Crystalline Form E:

In TGA analysis performed with samples of crystalline form E, these showed a weight loss in a range from 0.1 to 5.3%. Crystalline form E is considered to be an ansolvate form with varying amounts of residual solvent.

Figure 3E:
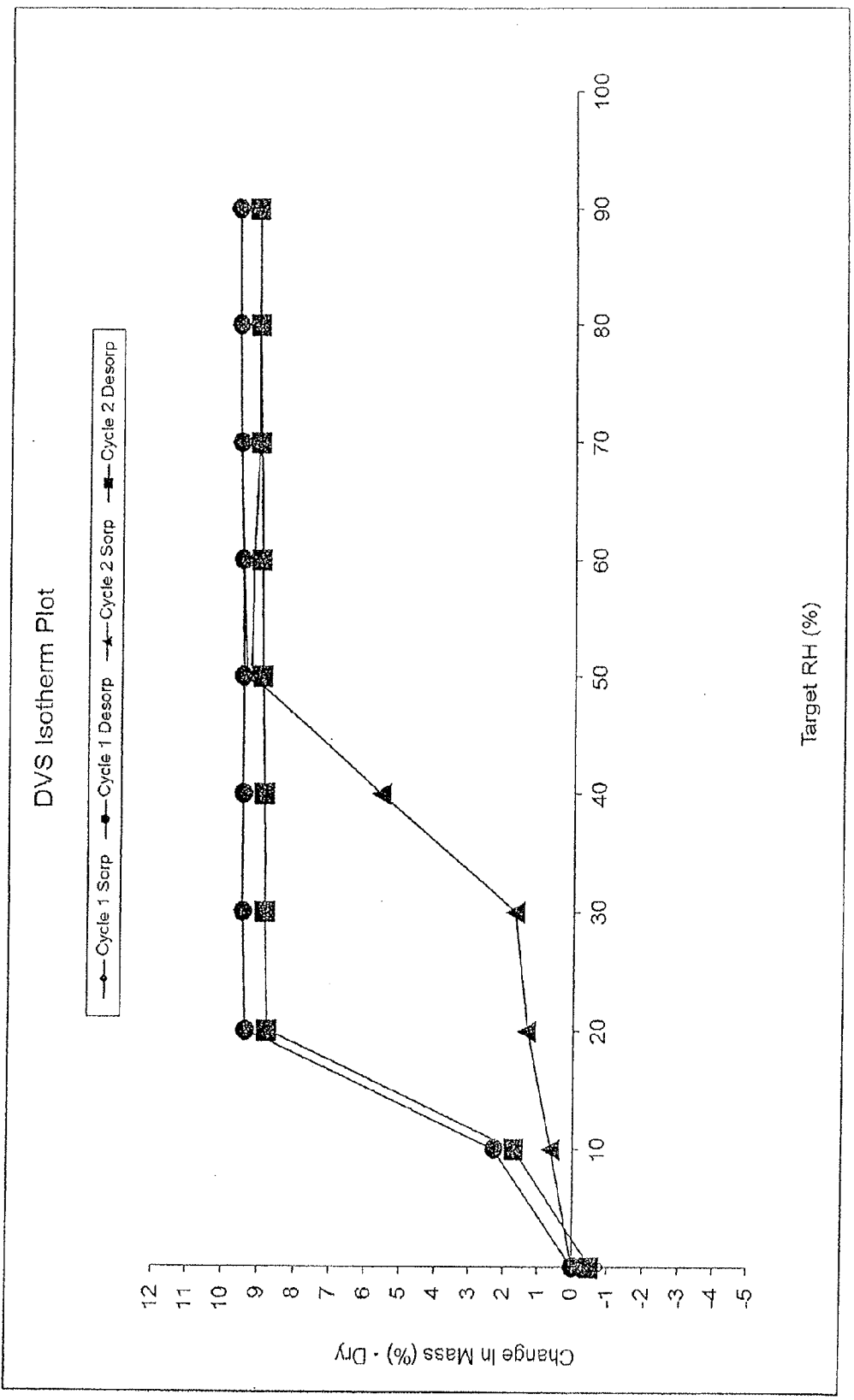

The existence of crystalline form E being a variable or discrete solvate (e.g. sesqui hydrate) cannot be fully excluded, since dynamic vapor sorption (DVS) experiments show a significant hysteresis between 10% and 40% relative humidity and a maximum weight gain, caused by moisture uptake, of about 4.6 to 5.8% in a range between 20% and 90% relative humidity (see FIG. 3e).

It cannot be excluded that crystalline form E has transformed to another crystalline form (e.g. crystalline form B) under conditions of the DVS experiments.

TGA analysis performed with samples of crystalline form G revealed a two-step mass loss of 2 to 7% which is, in conjunction with the data from the other analytic methods and/or knowledge about the synthesis conditions, indicative of crystalline form G being an ethanol solvate form, preferably a hemi- or mono ethanolate, or a hygroscopic form.

The existence of crystalline form G existing in another variable or discrete solvated state cannot be excluded. Crystalline form G may contain alcohol (e.g. ethanol) or water as residual solvent.

Crystalline Form H:

TGA analysis performed with a sample of crystalline form H revealed varying amount of residual solvent in the range of 2 to 8 wt-%, which in conjunction with the data from the other analytic methods suggests that polymorph H can be a non-stoichiometric or stoichiometric solvate. It cannot be excluded that crystalline form is an ansolvate.

Crystalline Form J:

TGA analysis performed with a sample of crystalline form J revealed residual solvent between 2.8% and 3.6%, which is, in conjunction with the data from the other analytic methods and/or knowledge about the synthesis conditions, indicative of crystalline form J being a solvate or hygroscopic form.

The existence of crystalline form J existing as variable or discrete solvated state cannot be excluded. Crystalline form J may contain alcohol (e.g. methanol) or water as residual solvent.

Crystalline for K:

According TGA analysis performed with a sample of crystalline form K this sample contained residual solvent in an amount between 2.1% and 4.0%, which is, in conjunction with the data from other analytic methods and/or knowledge about the synthesis conditions, indicative of crystalline form K being solvate or hygroscopic form.

The existence of crystalline form K existing as variable or discrete solvated state cannot be excluded. Crystalline form K may contain alcohol (e.g. methanol) or water as residual solvent.

Crystalline Form L:

TGA analysis performed with samples of crystalline form L revealed between 2 to 13% residual solvent (16.7% according to TGA), which is, in conjunction with data from other analytic methods and/or knowledge about the synthesis conditions, indicative of crystalline form J being solvate, preferably a variable or discrete toluene solvate.

The invention claimed is:

1. Crystalline form A of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine, which has X-ray powder diffraction peaks (CuKα radiation) at 8.7±0.2 (2Θ), 11.9±0.2 (2Θ), 17.4±0.2 (2Θ), and 27.1±0.2 (2Θ).

2. Crystalline form A according to claim 1, which has one or more Raman peaks selected from the group consisting of 1606±2 cm$^{-1}$, 1175±2 cm$^{-1}$, 1568±2 cm$^{-1}$, 1574±2 cm$^{-1}$ and 1650±2 cm$^{-1}$.

3. Crystalline form A according to claim 1, which in DSC analysis exhibits an endothermal event with an onset temperature in the range of 227° C. to 247° C. and/or a peak temperature in the range of 235° C. to 255° C.

4. Crystalline form A according to claim 1, which has X-ray powder diffraction peaks (CuKα radiation) of 8.7±0.2 (2Θ), 11.9±0.2 (2Θ), 17.4±0.2 (2Θ), 18.3±0.2 (2Θ), and 27.1±0.2 (2Θ).

5. Crystalline form A according to claim 1, which has at least one additional X-ray powder diffraction peak (CuKα radiation) selected from 7.7±0.2 (2Θ), 10.0±0.2 (2Θ), 15.3±0.2 (2Θ), 15.8±0.2 (2Θ), 21.9±0.2 (2Θ), and 22.2±0.2 (2Θ).

6. Crystalline form A according to claim 1, which has at least one additional X-ray powder diffraction peak selected from the group consisting of 10.0±0.2 (2Θ), 16.7±0.2 (2Θ), and 26.2±0.2 (2Θ).

7. Crystalline form A according to claim 1, which has one additional X-ray powder diffraction peak at about 17.8±0.2 (2Θ).

8. Crystalline form A according to claim 1, which has additional X-ray powder diffraction peaks at 10.0±0.2 (2Θ), 16.7±0.2 (2Θ), and 26.2±0.2 (2Θ).

9. Crystalline form A according to claim 8, which has at least one additional X-ray powder diffraction peak selected from about 15.3±0.2 (2Θ), and about 21.9±0.2 (2Θ).

10. Crystalline form A according to claim 1, which has additional X-ray powder diffraction peaks at about 18.3±0.2 (2Θ), 15.3±0.2 (2Θ), about 21.9±0.2 (2Θ), and about 16.7±0.2 (2Θ).

11. A pharmaceutical composition comprising at least one Crystalline form A according to claim 1.

12. A process for preparing Crystalline form A of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine according to claim 1, comprising the steps of
- (a-1') suspending cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine for at least 0.3 h in a solvent at a temperature in the range of 20° C. and the boiling point of the solvent, wherein the solvent is selected from the group consisting of isopropanol and a mixture of isopropanol and water, wherein the mixture may comprise up to 75 vol-% water;
- (b-1) separating by filtering off the solid obtained in step (a-1'), and
- (c-1) drying the solid obtained in step (b-1') at a temperature in the range of 0° to 75° C.

13. The process according to claim 12, wherein the solid obtained in step (b-1') is dried at a temperature in the range of 20 to 55° C.

14. The process according to claim 12, wherein the solid obtained in step (b-1') is dried at 50° C.

15. Crystalline form A according to claim 2, which in DSC analysis exhibits an endothermal event with an onset temperature in the range of 227° C. to 247° C., and/or a peak temperature in the range of 235° C. to 255° C.

16. Crystalline form A according to claim 2, which in DSC analysis exhibits an endothermal event with an onset temperature in the range of 240° C. to 245° C. and/or a peak temperature in the range of 245° C. to 250° C.

17. Crystalline form A according to claim 15, which in DSC analysis exhibits an endothermal event with an onset temperature in the range of 240° C. to 245° C. and/or a peak temperature in the range of 245° C. to 250° C.

18. A process for preparing Crystalline form A of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine according to claim 2, comprising the steps of
- (a-1') suspending cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine for at least 0.3 h in a solvent at a temperature in the range of 20° C. and the boiling point of the solvent, wherein the solvent is selected from the group consisting of isopropanol and a mixture of isopropanol and water, wherein the mixture may comprise up to 75 vol-% water;
- (b-1) separating by filtering off the solid obtained in step (a-1'), and
- (c-1) drying the solid obtained in step (b-1') at a temperature in the range of 0° to 75° C.

19. The process according to claim 18, wherein the solid obtained in step (b-1') is dried at a temperature in the range of 20 to 55° C.

20. The process according to claim 18, wherein the solid obtained in step (b-1') is dried at 50° C.

21. A process for preparing Crystalline form A of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine according to claim 3, comprising the steps of
- (a-1') suspending cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine for at least 0.3 h in a solvent at a temperature in the range of 20° C. and the boiling point of the solvent, wherein the solvent is selected from the group consisting of isopropanol and a mixture of isopropanol and water, wherein the mixture may comprise up to 75 vol-% water;
- (b-1) separating by filtering off the solid obtained in step (a-1'), and
- (c-1) drying the solid obtained in step (b-1') at a temperature in the range of 0° to 75° C., preferably at a temperature in the range of 20 to 55° C., more preferably at 50° C.

22. The process according to claim 21, wherein the solid obtained in step (b-1') is dried at a temperature in the range of 20 to 55° C.

23. The process according to claim 21, wherein the solid obtained in step (b-1') is dried at 50° C.

24. A process for preparing Crystalline form A of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine according to claim 4, comprising the steps of
- (a-1') suspending cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine for at least 0.3 h in a solvent at a temperature in the range of 20° C. and the boiling point of the solvent, wherein the solvent is selected from the group consisting of isopropanol and a mixture of isopropanol and water, wherein the mixture may comprise up to 75 vol-% water;
- (b-1) separating by filtering off the solid obtained in step (a-1'), and
- (c-1) drying the solid obtained in step (b-1') at a temperature in the range of 0° to 75° C.

25. The process according to claim 24, wherein the solid obtained in step (b-1') is dried at a temperature in the range of 20 to 55° C.

26. The process according to claim 24, wherein the solid obtained in step (b-1') is dried at 50° C.

27. A process for preparing Crystalline form A of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine according to claim 5, comprising the steps of
- (a-1') suspending cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine for at least 0.3 h in a solvent at a temperature in the range of 20° C. and the boiling point of the solvent, wherein the solvent is selected from the group consisting of isopropanol and a mixture of isopropanol and water, wherein the mixture may comprise up to 75 vol-% water;
- (b-1) separating by filtering off the solid obtained in step (a-1'), and
- (c-1) drying the solid obtained in step (b-1') at a temperature in the range of 0° to 75° C.

28. The process according to claim 27, wherein the solid obtained in step (b-1') is dried at a temperature in the range of 20 to 55° C.

29. The process according to claim 27, wherein the solid obtained in step (b-1') is dried at 50° C.

30. A process for preparing Crystalline form A of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine according to claim 6, comprising the steps of
- (a-1') suspending cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine for at least 0.3 h in a solvent at a temperature in the range of 20° C. and the boiling point of the solvent, wherein the solvent is selected from the group consisting of isopropanol and a mixture of isopropanol and water, wherein the mixture may comprise up to 75 vol-% water;
- (b-1) separating by filtering off the solid obtained in step (a-1'), and
- (c-1) drying the solid obtained in step (b-1') at a temperature in the range of 0° to 75° C.

31. The process according to claim 30, wherein the solid obtained in step (b-1') is dried at a temperature in the range of 20 to 55° C.

32. The process according to claim 30, wherein the solid obtained in step (b-1') is dried at 50° C.

33. A process for preparing Crystalline form A of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine according to claim 7, comprising the steps of
- (a-1') suspending cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine for at least 0.3 h in a solvent at a temperature in the range of 20° C. and the boiling point of the solvent, wherein the solvent is selected from the group consisting of isopropanol and a mixture of isopropanol and water, wherein the mixture may comprise up to 75 vol-% water;
- (b-1) separating by preferably filtering off the solid obtained in step (a-1'), and
- (c-1) drying the solid obtained in step (b-1') at a temperature in the range of 0° to 75° C.

34. The process according to claim 33, wherein the solid obtained in step (b-1') is dried at a temperature in the range of 20 to 55° C.

35. The process according to claim 33, wherein the solid obtained in step (b-1') is dried at 50° C.

36. A process for preparing Crystalline form A of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine according to claim 8, comprising the steps of
- (a-1') suspending cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine for at least 0.3 h in a solvent at a temperature in the range of 20° C. and the boiling point of the solvent, wherein the solvent is selected from the group consisting of isopropanol and a mixture of isopropanol and water, wherein the mixture may comprise up to 75 vol-% water;
- (b-1) separating by filtering off the solid obtained in step (a-1'), and
- (c-1) drying the solid obtained in step (b-1') at a temperature in the range of 0° to 75° C.

37. The process according to claim 36, wherein the solid obtained in step (b-1') is dried at a temperature in the range of 20 to 55° C.

38. The process according to claim 36, wherein the solid obtained in step (b-1') is dried at 50° C.

39. A process for preparing Crystalline form A of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine according to claim 9, comprising the steps of
- (a-1') suspending cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine for at least 0.3 h in a solvent at a temperature in the range of 20° C. and the boiling point of the solvent, wherein the solvent is selected from the group consisting of isopropanol and a mixture of isopropanol and water, wherein the mixture may comprise up to 75 vol-% water;
- (b-1) separating by filtering off the solid obtained in step (a-1'), and
- (c-1) drying the solid obtained in step (b-1') at a temperature in the range of 0° to 75° C.

40. The process according to claim 39, wherein the solid obtained in step (b-1') is dried at a temperature in the range of 20 to 55° C.

41. The process according to claim 39, wherein the solid obtained in step (b-1') is dried at 50° C.

42. A process for preparing Crystalline form A of cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine according to claim 10, comprising the steps of
- (a-1') suspending cis-(E)-4-(3-Fluorophenyl)-2',3',4',9'-tetrahydro-N,N-dimethyl-2'-(1-oxo-3-phenyl-2-propenyl)-spiro[cyclohexane-1,1'[1H]-pyrido[3,4-b]indol]-4-amine for at least 0.3 h in a solvent at a temperature in the range of 20° C. and the boiling point of the solvent, wherein the solvent is selected from the group consisting of isopropanol and a mixture of isopropanol and water, wherein the mixture may comprise up to 75 vol-% water;
- (b-1) separating by preferably filtering off the solid obtained in step (a-1'), and
- (c-1) drying the solid obtained in step (b-1') at a temperature in the range of 0° to 75° C.

43. The process according to claim 42, wherein the solid obtained in step (b-1') is dried at a temperature in the range of 20 to 55° C.

44. The process according to claim 42, wherein the solid obtained in step (b-1') is dried at 50° C.

* * * * *